US008029992B2

(12) United States Patent
Rapko et al.

(10) Patent No.: US 8,029,992 B2
(45) Date of Patent: Oct. 4, 2011

(54) METHODS OF EVALUATING CELLS AND CELL CULTURES

(75) Inventors: Stephen M. Rapko, Franklin, MA (US); Stephen J. Duguay, Salem, MA (US)

(73) Assignee: Genzyme Corporation, Cambridge, MA (US)

(*) Notice: Subject to any disclaimer, the term of this patent is extended or adjusted under 35 U.S.C. 154(b) by 559 days.

(21) Appl. No.: 12/098,033

(22) Filed: Apr. 4, 2008

(65) Prior Publication Data

US 2008/0248481 A1    Oct. 9, 2008

Related U.S. Application Data

(60) Provisional application No. 60/910,574, filed on Apr. 6, 2007.

(51) Int. Cl.
*C12Q 1/68* (2006.01)
*C12Q 1/02* (2006.01)
*C12P 19/34* (2006.01)
*G01N 33/53* (2006.01)

(52) U.S. Cl. .............. 435/6; 435/29; 435/91.2; 435/7.1

(58) Field of Classification Search ........................ None
See application file for complete search history.

(56) References Cited

U.S. PATENT DOCUMENTS

| | | | |
|---|---|---|---|
| 6,150,163 | A | 11/2000 | McPherson et al. |
| 7,169,610 | B2 | 1/2007 | Brown |
| 2003/0087259 | A1 * | 5/2003 | Clancy et al. ............ 435/6 |
| 2007/0292949 | A1 | 12/2007 | Duguay |

FOREIGN PATENT DOCUMENTS

| | | |
|---|---|---|
| WO | WO 2006/094836 A2 | 9/2006 |
| WO | WO 2007/149328 | 12/2007 |

OTHER PUBLICATIONS

Pusztai and Hess. Clinical trial design for microarray predictive marker discovery and assessment. Annals of Oncology, vol. 15, pp. 1731-1737, 2004.*
Golub et al. Molecular classification of cancer: Class discovery and class prediction by gene expression monitoring. Science, vol. 286, pp. 531-537, Oct. 1999.*
Tan et al. Classification analysis of the transcriptosome of nonlesional cultured dermal fibroblasts from systemic sclerosis patients with early disease. Arthitis & Rhematism, vol. 52, No. 3, pp. 865-876, Mar. 2005.*
Entrez Gene entry for MFAP5 microfibrillar associated protein 5 [*Homo sapiens*], Gene ID: 8076, updated on Nov. 1, 2010, printed as pp. 1-5 on Nov. 9, 2010.*
Entrez Gene entry for HAPLN1 hyaluronan and proteoglycan link protein 1 [*Homo sapiens*], Gene ID: 1404, updated on Nov. 1, 2010, printed as pp. 1-6 on Nov. 9, 2010.*
Rapko et al. Identification of the chondrocyte lineage using microfibril-associated glycoprotein-2, a novel marker that distinguishes chondrocytes from synovial cells. Tissue Engineering. Part C, Methods, vol. 16, No. 6, pp. 1367-1375, Dec. 2010.*
Appendix A of Real-Time PCR Systems: Applied Biosystems 7900HT Fast Real-Time PCR System and 7300/7500 Real-Time PCR Systems, *Chemistry Guide, Applied Biosystems*, 2005, Part No. 4348358 Rev. E, pp. A1-A4.
Applied Biosystems, "Amplification Efficiency of TaqMan® Gene Expression Assays", *Application Note TaqMan® Gene Expression Assays*, Publication 127AP05-03 (2006), printed as pp. 1-6.
Applied Biosystems, TaqMan® Gene Expression Assays, Assay ID Hs00157103_m1, retrieved online at https://products.appliedbiosystems.com on Oct. 30, 2006, printed as pp. 1-3.
Applied Biosystems, TaqMan® Gene Expression Assays, Assay ID Hs00185803_m1, retrieved online at https://products.appliedbiosystems.com on Oct. 30, 2006, printed as pp. 1-3.
Basad, et al. Treatment of Chondral Defects by Matrix-Guided Autologous Chondrocyte Implantation (MACI), in *Cartilage Surgery and Future Perspectives* 50-56 (2003).
Benya, et al., "Dedifferentiated Chondrocytes Rexpress the Differentiated Collagen Phenotype When Cultured in Agarose Gels", *Cell*, 30:215-224 (1982).
Binette, et al., "Expression of a Stable Articular Cartilage Phenotype without Evidence of Hypertrophy by Adult Human Articular Chondrocytes In Vitro", *Jour. of Orthopaed Research.*, 16:207-216 (1998).
Brittberg et al., "Treatment of Deep Cartilage Defects in the Knee with Autologous Chondrocyte Transplantation", *N.E. J. of Medicine*, 331:889-895 (1994).
Brittberg, M., "Autologous Chondrocyte Transplantation", *Clin. Orthopaedics and Related Research*, 367S:S147-155 (1999).
Buckwalter, et al., "The Effect of Link Protein on Proteoglycan Aggregate Structure", *Jour. of Biological Chem.*, 259(9):5361-5363 (1984).
Cherubino, et al., "Autologous chondrocyte implantation using a bilayer collagen membrane: A preliminary report", *Jour. of Orthopaedic Surgery*, 11(1):10-15 (2003).
Galbraith, et al., "Global analysis of cell type-specific gene expression", *Comparative and Functional Genomics*, 4:208-215 (2003).

(Continued)

*Primary Examiner* — Jennifer Dunston
(74) *Attorney, Agent, or Firm* — Finnegan, Henderson, Farabow, Garrett & Dunner, LLP

(57) ABSTRACT

Methods of evaluating the composition of a cell culture (e.g., to distinguish chondrocytes from fibroblasts) and methods for evaluating the phenotype of an individual cell (e.g., as a chondrocyte) are disclosed. The methods may be used, for example, for assessing chondrocyte cultures used for treatment of cartilage defects. In some embodiments, the invention involves identifying cell culture composition or the identity of a cell based on expression level of a fibroblast marker. In other embodiments, the invention involves comparing expression levels of at least one chondrocyte marker and at least one fibroblast marker in a cell culture sample or in an individual cell. In illustrative embodiments, the chondrocyte marker is hyaluronan and proteoglycan link protein 1 (HAPLN1), and the fibroblast marker is microfibrillar associated protein 5 (MFAP5).

34 Claims, 18 Drawing Sheets

OTHER PUBLICATIONS

GenBank Accession No. NM_000095, "*Homo sapiens* cartilage oliomeric matrix protein (COMP), mRNA", Dec. 2003.

GenBank Accession No. NM_000346, "*Homo sapiens* SRY (Sex determining region Y)-box 9 (campomelic dysplasia, autosomal sex-reversal) (SOX9), mRNA", Jul. 2005.

GenBank Accession No. NM_000900, "*Homo sapiens* matrix Gla protein (MGP), mRNA", Feb. 2006.

GenBank Accession No. NM_001011705, "*Homo sapiens* leukocyte cell derived chemotaxin 1 (LECT1), transcript variant 2, mRNA", Aug. 2006.

GenBank Accession No. NM_001135, "*Homo sapiens* aggrecan 1, transcript variant 1, mRNA", Oct. 2004.

GenBank Accession No. NM_001844, "*Homo sapiens* collagen, type II, alpha I (COL2A1), transcript variant 1, mRNA", Apr. 2003.

GenBank Accession No. NM_001851, "*Homo sapiens* collagen, type IX, alpha 1 (COL9A1), transcript variant 1, mRNA", Oct. 2006.

GenBank Accession No. NM_001854, "*Homo sapiens* collagen, type XI, alpha 1 (COL11A1), transcript variant A, mRNA", Sep. 2006.

GenBank Accession No. NM_001884, "*Homo sapiens* hyaluronan and proteoglycan link protein 1 (HAPLN1)", Oct. 2005.

GenBank Accession No. NM_003880, "*Homo sapiens* WNT1 inducible signaling pathway protein 3 (WISP3), transcript variant 1, mRNA", Aug. 2006.

GenBank Accession No. NM_005711,"*Homo sapiens* EGF-like repeats and discoidin I-like domains 3 (EDIL3), mRNA", Oct. 2005.

GenBank Accession No. NM_006272, "*Homo sapiens* S100 calcium binding protein, beta (neural) (S100B), mRN", Aug. 2005.

GenBank Accession No. NM_006393, "*Homo sapiens* nebulette (NEBL), transcript variant 1 mRNA", Apr. 2008.

GenBank Accession No. NM_007015, "*Homo sapiens* leukocyte cell derived chemotaxin 1 (LECT1), transcript variant 1, mRNA", Apr. 2005.

GenBank Accession No. NM_013227, "*Homo sapiens* aggrecan 1 (AGC1), transcript variant 2, mRNA", Oct. 2004.

GenBank Accession No. NM_018058, "*Homo sapiens* cartilage acidic protein 1 (CRTAC1), mRNA", Sep. 2005.

GenBank Accession No. NM_033150, "*Homo sapiens* collagen, type II, alpha 1 (COL2A1), transcript variant 2, mRNA", Apr. 2003.

GenBank Accession No. NM_078485, "*Homo sapiens* collagen, type IX, alpha 1 (COL9A1), transcript variant 2, mRNA", Oct. 2006.

GenBank Accession No. NM_080629, "*Homo sapiens* collagen, type XI, alpha 1 (COL11A1), transcript variant B, mRNA", Sep. 2006.

GenBank Accession No. NM_080630, "*Homo sapiens* collagen, type XI, alpha 1 (COL11A1), transcript variant C, mRNA", Sep. 2006.

GenBank Accession No. NM-003480, "*Homo sapiens* microfibrillar associated protein (MFAP5), mRNA", Sep. 2005.

Gibson, et al., "Further Characterization of Proteins Associated with Elastic Fiber Microfibrils Including the Molecular Cloning of MAGP-2 (MP25)", *Jour. of Biol. Chem.*, 271:1096-1103 (1996).

Gibson, et al., "Microfibril-associated Glycoprotein-2 (MAGP-2) Is Specifically Associated with Fibrillin-containing Microfibrils but Exhibits More Restricted Patterns of Tissue Localization and Developmental Expression Than Its Structural Relative MAGP-1", *Jour. of Histochem. & Cytochem.*, 46(8):871-885 (1998).

Haudenschild, et al., "Differential Expression of Multiple Genes During Articular Chondrocyte Redifferentiation", *The Anatomical Record*, 263:91-98 (2001).

Imabayashi, et al., "Redifferentiation of dedifferentiated chondrocytes and chondrogenesis of human bone marrow stromal cells via chondrosphere formation with expression profiling by large-scale cDNA analysis", *Experimental Cell Research*, 288:35-50 (2003).

Lemaire, et al., "Increased Expression of Type I Collagen Induced by Microfibril-Associated Glycoprotein 2", *Arthritis & Rheumatism*, 52:1812-1823 (2005).

Lemaire, et al., "Mutant Fibrillin 1 From tight Skin Mice Increases Extracellular Matrix Incorporation of Microfibril-Associated Glycoprotein 2 and type I Collagen", *Arthritis & Rheumatism*, 50(3):915-926 (2004).

Leung, et al., "Fundametnals of cDNA microarray data analysis", *TRENDS in Genetics*, 19(11):649-659 (2003).

Linsenmeyer et al., "Monoclonal Antibodies to Connective Tissue Macromolecules: Type II Collagen", *Biochem. Biophys. Res. Com.*, 92(2):440-6 (1980).

Marlovits, et al., "Early postoperative adherence of matrix-induced autologous chondrocyte implantation for the treatment of full-thickness cartilage defects of the femoral condyle", *Knee Surg. Sports Traumatol Arthrosc.*, 12:451-457 (2005).

Rapko, et al., "DNA Methylation Analysis as Novel Tool for Quality Control in Regenerative Medicine", *Tissue Engineering*, 13(9):2271-2280 (2007).

Reno et al., "Rapid Isolation of Total RNA from Small Samples of Hypocellular, Dense Connective Tissues", *Biotechniques*, 22(6):1082-1086 (1997).

International Search Report issued in PCT/US2008/059275, mailed on Aug. 5, 2008.

Written Opinion issued in PCT/US2008/059275, mailed on Aug. 5, 2008.

Kolettas, E. et al. "Expression of cartilage-specific molecules is retained on long-term culture of human articular chondrocytes" *J. Cell Science* 108:1991-1999 (1995).

Marlovits, S. et al. "Differential Gene-Expression of Human Articular Chondrocytes and Human Fibroblasts in Two- and Three-dimensional Cell Culture" *FASEB J.* 15(4):A34 (Mar. 7, 2001).

Rapko, S. et al. "Identification of dedifferentiated chondrocytes using gene expression—the dsc array" *Osteoarthritis and Cartilage* 15(Suppl. B): poster P195, p. B137 (Sep. 2007).

Stokes, D.G. et al. "Assessment of the Gene Expression Profile of Differentiated and Dedifferentiated Human Fetal Chondrocytes by Microarray Analysis" *Arthritis & Rheumatism* 46(2):404-419 (Feb. 2002).

\* cited by examiner

SEQUENCE LISTING

<160> NUMBER OF SEQ ID NOS: 27

<210> SEQ ID NO 1
<211> LENGTH: 2900
<212> TYPE: DNA
<213> ORGANISM: Homo sapiens

<400> SEQUENCE: 1

```
attccagcct cattgtaaca cacattctac gcctagcctg gctttcttgc tctccctcat      60
ctcattgttt cagcggaggc caaatctgaa gtcctttcca gggagtggct ctgttcatct     120
tattcgccag ccaaagtagg aacagcgtaa gaggagagag acacattcag cagccaaagg     180
actcggtgga aagagcagaa caccatagac aatatgtcgc tcttgggacc caaggtgctg     240
ctgtttcttg ctgcattcat catcacctct gactggatac ccctgggggt caatagtcaa     300
cgaggagacg atgtgactca agcgactcca gaaacattca cagaagatcc taatctggtg     360
aatgatcccg ctacagatga aacagttttg gctgttttgg ctgatattgc accttccaca     420
gatgacttgg cctccctcag tgaaaaaaat accactgcag agtgctggga tgagaaattt     480
acctgcacaa ggctctactc tgtgcatcgg ccggttaaac aatgcattca tcagttatgc     540
ttcaccagtt tacgacgtat gtacatcgtc aacaaggaga tctgctctcg tcttgtctgt     600
aaggaacacg aagctatgaa agatgagctt tgccgtcaga tggctggtct gccccctagg     660
agactccgtc gctccaatta cttccgactt cctccctgtg aaaatgtgga tttgcagaga     720
cccaatggtc tgtgatcatt gaaaaagagg aaagaagaaa aaatgtatgg gtgagaggaa     780
ggaggatctc cttcttctcc aaccattgac agctaaccct tagacagtat ttcttaaacc     840 aatcctttg caatgtccag cttttacccc tactctctac tttttcaccc aaactgataa     900
catttatctc attttctagc acttaaaata caaagtctat attattgcat aattttgctg     960
cttctcaata tcatagacac agtgaataga tgatgactat atggcttata tacaaacatt    1020
ctatgtacaa tttcaaggga gactaaactt taggctaata atctttacta ttgaatctgt    1080
ctgatataga tcttagggtt gaagaagcta tctttgtcta tttgggctaa ccatagaatt    1140
tcatttattt tcctcacaat attttcctag accaactccc catcattcac gtgttcctct    1200
ttactcttac tttaactatt ttgctggctt gcccgaaaat ttgcctggca agtcttcctt    1260
ataagacaca tcatggtaag tttttgtagtc ctgtaagatt ctgcaacaca gtcaagaatt    1320
atacaatcct actagcaata tataaggacc caaaatgtct tctgctaagc tcagaggctg    1380
gggctaaagc atgaggacta tgccagctat agaacttgga ctcataattc gctatccaat    1440
ttttcatgca gttgtctagt cgggaagtaa ggttggaaac taagtctcat ttactgattc    1500
```

```
gtttatgggt agtaccggga tgaacccacc accacaaagc aaattagaca acttaatgtg   1560
aaatcatacc attggttgac gtttccttga gttgctactt cgttcatctt cacaacttaa   1620
caagtgcacg gtcgaattat tgtgcaagtg gcttttggat atcctgattg gggcctaaga   1680
agggcattca gacttgaatt ttaataggca gacagaaagt ttgcctaata gttaatacga   1740
aagagtgaaa gaaacacaat attcagacaa cccacattct tatcctggct ctagcagtaa   1800
ccacgtagcc ttggataagc cattttcctt cattaggtcc tggtttaatt tcctcatctt   1860
taaaatgaga aggttaaatt tatcttagta ctgctgggcg cagtggctca tgcctgtaat   1920
ctgagcactt tgggaagctg aggcgggtgg atcacttgag gtcagaaatt tgagacgagc   1980
ctggccaaca tggtgaaacc ccatctctac taaaaataca aaaattagct gggcgtggtg   2040
gcacgtgcct gtaatcccag ctactcggga ggctgaggca ggagaatcaa ttgaacctgg   2100
gaggcagagg ttgcagtgag ccgagatggc gccattgcac tccagcctgg gtgacaaaag   2160
caaaagtcca tcttaagaaa tatatatata tattatatat attcttagtt ctaagatttc   2220
ctttaattct atgattctct ggatttaaat gcattattca tatttcttga agcttagata   2280
cagtctaatt catagcaacc atatctgctt tatcctaggt gagggtagca gtccacaatg   2340
gaatagaaga aaatcccatt ataacaaatg acaaattata tatcatgaat ccttctgtct   2400
gactaactca ataactttct ataaaagcca atggaattca aataggagct aggagacaac   2460
aagttatata tgacagtgga ggttgtattc ctttatatt gctgagaaaa ctagttaaat   2520
gatcagattc ttgctgttaa gaaacaattt cgtttaatgg gatctgtaca actgattta   2580 aaaaaatgct acaaaaagcc ccaaagcata taatctctac tccttacagt ctctagaatt   2640
aaatgtactc atttagacaa catattaaat gcatatttta gccactttag agaaacctca   2700
taggcacaga gtttccaaga ttaattttaa gaatatcttc acgaacttga ccctcctact   2760
ccacattgca acatttccat cagacagcat ttcaattcca gtattatgta tattgcaaat   2820
taaacatttt aaaatatttt tttccaattt atttctcaaa ataaaatgtc ttttgttctg   2880
gtaaaaaaaa aaaaaaaaa                                                2900
```

<210> SEQ ID NO 2
<211> LENGTH: 1759
<212> TYPE: DNA
<213> ORGANISM: Homo sapiens

<400> SEQUENCE: 2

```
gtgaggagaa agagcgctac gttcacttga tctccagctt ccaacttaag cagaacttga     60
gagcatccga actcctggat ttcaggacaa gtgaagaaga ttctttgggc tataaagatg    120
aagagtctac ttcttctggt gctgatttca atctgctggg ctgatcatct ttcagacaac    180
tatactctgg atcatgacag agctattcac atccaagcag aaaatggccc ccatctactt    240
gtggaagcag agcaagccaa ggtgttttca cacagaggtg gcaatgttac actgccatgt    300 aaatttatc gagaccctac agcatttggc tcaggaatcc ataaaatccg aattaagtgg    360
accaagctaa cttcggatta cctcaaggaa gtggatgttt tgtttccat gggataccac    420 aaaaaaacct atggaggcta ccagggtaga gtgtttctga agggaggcag tgatagtgat    480
gcttctctgg tcatcacaga cctcactctg gaagattatg ggagatataa gtgtgaggtg    540
attgaaggat tagaagatga tactgttgtg gtagcactgg acttacaagg tgtggtattc    600
ccttactttc cacgactggg cgctacaat tcaatttttc acgaggcgca gcaggcgtgt    660
ctggaccagg atgctgtgat cgcctccttc gaccagctgt acgacgcctg gcggggcggg    720
```

```
ctggactggt gcaatgccgg ctggctcagt gatggctctg tgcaatatcc catcacaaag      780
cccagagagc cctgtggggg ccagaacaca gtgcccggag tcaggaacta cggattttgg      840
gataaagata aaagcagata tgatgttttc tgttttacat ccaatttcaa tggccgtttt      900
tactatctga tccaccccac caaactgacc tatgatgaag cggtgcaagc ttgtctcaat      960
gatggtgctc agattgcaaa agtgggccag atatttgctg cctggaaaat tctcggatat     1020
gaccgctgtg atgcgggctg gttggcggat ggcagcgtcc gctacccat  ctctaggcca     1080 agaaggcgct gcagtcctac tgaggctgca gtgcgcttcg tgggtttccc agataaaaag     1140
cataagctgt atggtgtcta ctgcttcaga gcatacaact gaatgtgccc ttagagcgca     1200
tcagttttaa agtcattaag aacatgtgaa aggtgttttt tttttccaat atgaactcat     1260
gcaagttacc aaaactgtga taacccttt ttacttactg taaagagtca ttttcataag     1320
atcaattcat tgatttgttt tttgtaaagc tatcattcaa tatatattat aaattaatat     1380
aaatttaagg gaagctctat gtaaggagac ttagagccaa actgtttaag ctgtatcatc     1440
ccaacaaagt atcctttcat gaacggggca tgcaatagct taagaattgc taggattaaa     1500
ttaaggaaag taaagctact cagagcaaca ggttccacaa gcacaaactt tacacatttg     1560
tacaattttg aaatgcacta caataaacaa attagagcaa cacatttgaa atacaggctt     1620
ctttacataa actgagaggt tatacaaaac tcagtttcac aagggaacaa tctataccct     1680
tctaaaagtt aatatttcaa gtctctaata ggcagaatat tttactcttt aaaatcctgc     1740
ctttctgacc aaaaaaaaa                                                  1759

<210> SEQ ID NO 3
<211> LENGTH: 661
<212> TYPE: DNA
<213> ORGANISM: Homo sapiens

<400> SEQUENCE: 3
tggttcttat aaaaacctca cagccttcca ctaacatccc gtaggagcct ctctccctac       60
tgctgctaca caagaccctg agactgacct gcaggacgaa accatgaaga gcctgatcct      120
tcttgccatc ctggccgcct tagcggtagt aactttgtgt tatgaatcac atgaaagcat      180
ggaatcttat gaacttaatc ccttcattaa caggagaaat gcaaatacct tcatatcccc      240
tcagcagaga tggagagcta aagtccaaga gaggatccga gaacgctcta agcctgtcca      300
cgagctcaat agggaagcct gtgatgacta cagactttgc gaacgctacg ccatggttta      360
tggatacaat gctgcctata atcgctactt caggaagcgc cgagggacca aatgagactg      420
agggaagaaa aaaatctct ttttttctgg aggctggcac ctgatttgt atccccctgt       480 agcagcatta ctgaaataca taggcttata tacaatgctt cttcctgta tattctcttg      540 tctggctgca ccccttttc ccgcccccag attgataagt aatgaaagtg cactgcagtg      600
agggtcaaag gagagtcaac atatgtgatt gttccataat aaacttctgg tgtgatactt      660
t                                                                      661

<210> SEQ ID NO 4
<211> LENGTH: 2974
<212> TYPE: DNA
<213> ORGANISM: Homo sapiens

<400> SEQUENCE: 4
agaagccccg cagccgccgc gcggagaaca gcgacagccg agcgcccggt ccgcctgtct       60
gccggtgggt ctgcctgccc gcgcagcaga cccggggcgg ccgcgggagc ccgcgccccg      120
```

```
cccgccgcgc ctctgccggg acccacccgc agcggagggc tgagcccgcc ggcggctccc      180
cggagctcac ccacctccgc gcgccggagc gcaggcaaaa ggggaggaaa ggctcctctc      240
tttagtcacc actctcgccc tctccaagaa tttgtttaac aaagcgctga ggaaagagaa      300
cgtcttcttg aattctttag taggggcgga gtctgctgct gccctgcgct gccacctcgg      360
ctacactgcc ctccgcgacg accctgacc agccggggtc acgtccggga gacgggatca      420
tgaagcgctc ggtagccgtc tggctcttgg tcgggctcag cctcggtgtc cccagttcg      480 gcaaaggtga tatttgtgat cccaatccat gtgaaaatgg aggtatctgt tgccaggat      540 tggctgatgg ttccttttcc tgtgagtgtc cagatggctt cacagacccc aactgttcta      600
gtgttgtgga ggttgcatca gatgaagaag aaccaacttc agcaggtccc tgcactccta      660
atccatgcca atggagga acctgtgaaa taagtgaagc ataccgaggg gatacattca      720
taggctatgt ttgtaaatgt ccccgaggat ttaatgggat tcactgtcag cacaacataa      780
atgaatgcga agttgagcct tgcaaaaatg gtggaatatg tacagatctt gttgctaact      840
attcctgtga gtgcccaggc gaatttatgg aagaaattg tcaatacaaa tgctcaggcc      900
cactgggaat tgaaggtgga attatatcaa accagcaaat cacagcttcc tctactcacc      960
gagctctttt tggactccaa aaatggtatc cctactatgc acgtcttaat aagaaggggc     1020
ttataaatgc gtggacagct gcagaaaatg acagatggcc gtggattcag ataaaatttgc     1080 aaaggaaaat gagagttact ggtgtgatta cccaaggagc caagaggatt ggaagcccag     1140
agtatataaa atcctacaaa attgcctaca gtaatgatgg aaagacttgg gcaatgtaca     1200
aagtgaaagg caccaatgaa gacatggtgt tcgtggaaa cattgataac aacactccat     1260
atgctaactc tttcacaccc cccataaaag ctcagtatgt aagactctat ccccaagttt     1320
gtcgaagaca ttgcactttg cgaatggaac ttcttggctg tgaactgtcg ggttgttctg     1380
agcctctggg tatgaaatca ggacatatac aagactatca gatcactgcc tccagcatct     1440
tcagaacgct caacatggac atgttcactt gggaaccaag gaaagctcgg ctggacaagc     1500
aaggcaaagt gaatgcctgg acctctggcc acaatgacca gtcacaatgg ttacaggtgg     1560
atcttcttgt tccaaccaaa gtgactggca tcattacaca aggagctaaa gattttggtc     1620
atgtacagtt tgttggctcc tacaaactgg cttacagcaa tgatggagaa cactggactg     1680
tataccagga tgaaaagcaa agaaaagata aggttttcca gggaaatttt gacaatgaca     1740
ctcacagaaa aaatgtcatc gacccctccca tctatgcacg acacataaga atccttcctt     1800
ggtcctggta cggaggatc acattgcggt cagagctgct gggctgcaca gaggaggaat     1860
gaggggaggc tacatttcac aaccctcttc cctatttccc taaaagtatc tccatggaat     1920
gaactgtgca aaatctgtag gaaactgaat ggtttttttt tttttttcat gaaaagtgc     1980 tcaaattatg gtaggcaact aacggtgttt ttaagggggt ctaagcctgc cttttcaatg     2040
atttaatttg atttatttt atccgtcaaa tctcttaagt aacaacacat taagtgtgaa     2100
ttacttttct ctcattgttt cctgaattat tcgcattggt agaaatatat tagggaaaga     2160
aagtagcctt cttttatag caagagtaaa aaagtctcaa agtcatcaaa taagagcaag     2220
agttgataga gcttttacaa tcaatactca cctaattctg ataaaaggaa tactgcaatg     2280
ttagcaataa gttttttct tctgtaatga ctctacgtta tcctgtttcc ctgtgcctac     2340
caaacactgt caatgtttat tacaaaattt taaagaagaa tatgtaacat gcagtactga     2400
tattataatt tcatttac tttcattatt tctaataaga gattatgtga cttcttttc     2460 ttttagttct attctacatt cttaatattg tatattacct gaataattca attttttct     2520
```

| | |
|---|---|
| aattgaattt cctattagtt gactaaaaga agtgtcatgt ttactcatat atgtagaaca | 2580 |
| tgactgccta tcagtagatt gatctgtatt taatattcgt taattaaatc tgcagtttta | 2640 |
| tttttgaagg aagccataac tatttaattt ccaataatt gcttcataaa gaatcccata | 2700 |
| ctctcagttt gcacaaaaga acaaaaaata tatatgtctc tttaaattta aatcttcatt | 2760 |
| tagatggtaa ttacatatcc ttatatttac tttaaaaaat cggcttattt gtttatttta | 2820 |
| taaaaattt agcaaagaaa tattaatata gtgctgcata gtttggccaa gcatactcat | 2880 |
| catttctttg ttcagctcca catttcctgt gaaactaaca tcttattgag atttgaaact | 2940 |
| ggtggtagtt tcccaggaag gcacaggtgg agtt | 2974 |

<210> SEQ ID NO 5
<211> LENGTH: 1307
<212> TYPE: DNA
<213> ORGANISM: Homo sapiens

<400> SEQUENCE: 5

| | |
|---|---|
| cctgagtccc gggaggaaag tgctcgccca ttcctgacct gtgacacgct cactgcgaag | 60 |
| gcaggttatt agaagagtcc catgaaaggt ggctccacgg tcccagcgac atgcaggggc | 120 |
| tcctcttctc cactcttctg cttgctggcc tggcacagtt ctgctgcagg gtacagggca | 180 |
| ctggaccatt agatacaaca cctgaaggaa ggcctggaga agtgtcagat gcacctcagc | 240 |
| gtaaacagtt ttgtcactgg ccctgcaaat gccctcagca gaagcccgt tgccctcctg | 300 |
| gagtgagcct ggtgagagat ggctgtggat gctgtaaaat ctgtgccaag caaccagggg | 360 |
| aaatctgcaa tgaagctgac ctctgtgacc cacacaaagg gctgtattgt gactactcag | 420 |
| tagacaggcc taggtacgag actggagtgt gtgcatacct tgtagctgtt gggtgcgagt | 480 |
| tcaaccaggt acattatcat aatggccaag tgtttcagcc caacccttg ttcagctgcc | 540 |
| tctgtgtgag tggggccatt ggatgcacac ctctgttcat accaaagctg ctggcagtc | 600 |
| actgctctgg agctaaaggt ggaaagaagt ctgatcagtc aaactgtagc ctggaaccat | 660 |
| tactacagca gctttcaaca agctacaaaa caatgccagc ttatagaaat ctcccactta | 720 |
| tttggaaaaa aaaatgtctt gtgcaagcaa caaaatggac tccctgctcc agaacatgtg | 780 |
| ggatgggaat atctaacagg gtgaccaatg aaaacagcaa ctgtgaaatg agaaaagaga | 840 |
| aaagactgtg ttacattcag ccttgcgaca gcaatatatt aaagacaata aagattccca | 900 |
| aaggaaaaac atgccaacct actttccaac tctccaaagc tgaaaaattt gtcttttctg | 960 |
| gatgctcaag tactcagagt tacaaaccca cttttgtgg aatatgcttg ataagagat | 1020 |
| gctgtatccc taataagtct aaaatgatta ctattcaatt tgattgccca aatgaggggt | 1080 |
| catttaaatg gaagatgctg tggattacat cttgtgtgtg tcagagaaac tgcagagaac | 1140 |
| ctggagatat attttctgag ctcaagattc tgtaaaacca agcaaatggg ggaaaagtta | 1200 |
| gtcaatcctg tcatataata aaaaaattag tgagtaaaaa aaaaaaaaaa aaaaaaaaa | 1260 |
| aaaaaaaaaa aaaaaaaaa aaaaagaaa aaaaaaaaa aaaaaa | 1307 |

<210> SEQ ID NO 6
<211> LENGTH: 7137
<212> TYPE: DNA
<213> ORGANISM: Homo sapiens

<400> SEQUENCE: 6

| | |
|---|---|
| cggccaggtg tgtgggactg aagttcttgg agaagggagt ccaactcttc aaggtgaact | 60 |
| atgaccactt tactctgggt tttcgtgact ctgagggtca tcactgcagc tgtcactgta | 120 |

```
gaaacttcag accatgacaa ctcgctgagt gtcagcatcc cccaaccgtc cccgctgagg    180
gtcctcctgg ggacctccct caccatcccc tgctatttca tcgaccccat gcaccctgtg    240
accaccgccc cttctaccgc cccactggcc ccaagaatca agtggagccg tgtgtccaag    300
gagaaggagg tagtgctgct ggtggccact gaagggcgcg tgcgggtcaa cagtgcctat    360
caggacaagg tctcactgcc caactacccg gccatcccca gtgacgccac cttggaagtc    420
cagagcctgc gctccaatga ctctggggtc taccgctgcg aggtgatgca tggcatcgag    480
gacagcgagg ccaccctgga agtcgtggtg aaaggcatcg tgttccatta cagagccatc    540
tctacacgct acaccctcga ctttgacagg gcgcagcggg cctgcctgca gaacagtgcc    600
atcattgcca cgcctgagca gctgcaggcc gcctacgaag acggcttcca ccagtgtgac    660
gccggctggc tggctgacca gactgtcaga tacccccatcc acactccccg ggaaggctgc    720
tatggagaca aggatgagtt cctggtgtg aggacgtatg gcatccgaga caccaacgag    780
acctatgatg tgtactgctt cgccgaggag atggagggtg aggtctttta tgcaacatct    840
ccagagaagt tcaccttcca ggaagcagcc aatgagtgcc ggcggctggg tgcccggctg    900
gccaccacgg gccacgtcta cctggcctgg caggctggca tggacatgtg cagcgccggc    960
tggctggccg accgcagcgt gcgctacccc atctccaagg cccggcccaa ctgcggtggc   1020
aacctcctgg gcgtgaggac cgtctacgtg catgccaacc agacgggcta ccccgacccc   1080
tcatcccgct acgacgccat ctgctacaca ggtgaagact ttgtggacat cccagaaaac   1140
ttctttggag tgggggtga ggaggacatc accgtccaga cagtgacctg gcctgacatg   1200
gagctgccac tgcctcgaaa catcactgag ggtgaagccc gaggcagcgt gatccttacc   1260
gtaaagccca tcttcgaggt ctcccccagt ccccctggaac ccgaggagcc cttcacgttt   1320
gcccctgaaa taggggccac tgccttcgct gaggttgaga atgagactgg agaggccacc   1380
aggccctggg gctttcccac acctggcctg ggccctgcca cggcattcac cagtgaggac   1440
ctcgtcgtgc aggtgaccgc tgtccctggg cagccgcatt tgccagggg ggtcgtcttc   1500
cactaccgcc cggagcccac ccgctactcg ctgacctttg aggaggcaca gcaggcctgc   1560
cctggcacgg gggcggtcat tgcctcgccg gagcagctcc aggccgccta cgaagcaggc   1620
tatgagcagt gtgacgccgg ctggctgcgg gaccagaccg tcagataccc cattgtgagc   1680
ccacggaccc catgcgtggg tgacaaggac agcagcccag gggtcaggac ctatggcgtg   1740
cgcccatcaa cagagaccta cgatgtctac tgctttgtag acagacttga gggggaggtg   1800
ttcttcgcca cacgccttga gcagttcacc ttccaggaag cactggagtt ctgtgaatct   1860
cacaatgcca ctgccaccac gggccagctc tacgccgcct ggagccgcgg cctggacaag   1920
tgctatgccg gctggctggc cgacggcagc tccgctacc ccatcgtcac cccaaggcct   1980
gcctgcggtg gggacaagcc aggcgtgaga acggtctacc tctaccctaa ccagacgggc   2040
ctcccagacc cactgtcccg gcaccatgcc ttctgcttcc gaggcatttc agcggttcct   2100
tctccaggag aagaagaggg tggcacaccc acatcaccct ctggtgtgga ggagtggatc   2160
gtgacccaag tggttcctgg tgtggctgct gtccccgtag aagaggagac aactgctgta   2220
ccctcagggg agactactgc catcctagag ttcaccaccg agccagaaaa ccagacagaa   2280
tgggaaccag cctatacccc agtgggcaca tccccgctgc cagggatcct tcctacttgg   2340
cctcctactg gcgccgaaac agaggaaagt acagaaggcc cttctgcaac tgaagtgccc   2400
tctgcctcag aggaaccatc cccctcgagg gtgccattcc cctcagagga gccatccccc   2460
tcagaggaac cattcccctc agtgaggcca ttcccctcag tggagctgtt ccctcagag   2520
```

```
gagccattcc cctccaagga gccatccccc tcagaggaac catcagcctc agaagagccg    2580
tatacacctt cacccccccga gcccagctgg actgagctgc ccagtctctgg ggaggaatct   2640
ggggcccctg atgtcagtgg tgacttcaca ggcagtggag atgtttcagg acaccttgac    2700
ttcagtgggc agctgtcagg ggacagggca agtggactgc cctctggaga cctggactcc    2760
agtggtctta cttccacagt gggctcaggc ctgactgtgg aaagtggact accctcaggg    2820
gatgaagaga gaattgagtg gcccagcact cctacgttg tgaactgcc ctctggagct      2880
gagatcctag agggctctgc ctctggagtt ggggatctca gtggacttcc ttctggagaa    2940
gttctagaga cctctgcctc tggagtagga ccctcagtg gcttccttc tggagaagtt      3000
ctagagacca ctgcccctgg agtagaggac atcagcgggc ttccttctgg agaagttcta    3060
gagaccactg cccctggagt agaggacatc agcgggcttc cttctggaga agttctagag    3120
accactgccc ctggagtaga ggacatcagc gggcttcctt ctggagaagt tctagagacc    3180
actgcccctg gagtagagga catcagcggg cttccttctg gagaagttct agagaccact    3240
gcccctggag tagaggacat cagcgggctt ccttctggag aagttctaga gaccgctgcc    3300
cctggagtag aggacatcag cgggcttcct tctggagaag ttctagagac cgctgccccct   3360
ggagtagagg acatcagcgg gcttccttct ggagaagttc tagagaccgc tgcccctgga    3420
gtagaggaca tcagcgggct tccttctgga gaagttctag agaccgctgc ccctggagta    3480
gaggacatca gcgggcttcc ttctggagaa gttctagaga ccgctgcccc tggagtagag    3540
gacatcagcg gcttccttc tggagaagtt ctagagaccg ctgcccctgg agtagaggac     3600
atcagcgggc ttccttctgg agaagttcta gagaccgctg cccctggagt agaggacatc    3660
agcgggcttc cttctggaga agttctagag actgctgccc ctggagtaga ggacatcagc    3720
gggcttcctt ctggagaagt tctagagact gctgcccctg gagtagagga catcagcggg    3780
cttccttctg gagaagttct agagactgct gcccctggag tagaggacat cagcgggctt    3840
ccttctggag aagttctaga gactgctgcc cctggagtag aggacatcag cgggcttcct    3900
tctggagaag ttctagagac tactgccccct ggagtagagg atcagcgg gcttccttct    3960
ggagaagttc tagagactac tgcccctgga gtagatgaga tcagtgggct tccttctgga    4020
gaagttctag agactactgc cctggagta gaggagatca gcgggcttcc ttctggagaa     4080
gttctagaga cttctacctc tgcggtaggg gacctcagtg gacttccttc tggaggagaa    4140
gttctagaga tttctgtctc tggagtagag gacatcagtg gcttccttc tggagaggtt     4200
gtagagactt ctgcctctgg aatagaggat gtcagtgaac ttccttcagg agaaggtcta    4260
gagacctctg cttctggagt agaggacctc agcaggctcc cttctggaga agaagttcta    4320
gagatttctg cctctggatt tggggacctc agtggagttc cttctggagg agaaggtcta    4380
gagacctctg cttctgaagt agggactgac ctcagtgggc ttccttctgg aagggagggt    4440
ctagagactt cagcttctgg agctgaggac ctcagtgggt tgccttctgg aaaagaagac    4500
ttggtgggt cagcttctgg agacttggac ttgggcaaac tgccttctgg aactctagga     4560
agtgggcaag ctccagaaac aagtggtctt ccctctggat ttagtggtga gtattctggg    4620
gtggaccttg gaagtggccc accctctggc ctgcctgact ttagtggact tccatctgga    4680
ttcccaactt tttccctagt ggattctaca ttggtgaag tggtcacagc ctccactgca     4740
agtgaactgg aagggagggg aaccattggc atcagtggtg caggagaaat atctggactg    4800
ccctccagtg agctggacat tagtgggaga gctagtggac tcccttcagg aactgaactc    4860
agtggccaag catctgggtc tcctgatgtc agtggggaaa tacctggact ctttggtgtc    4920
```

```
agtggacagc catcagggtt tcctgacact agtggggaaa catctggagt gactgagctt    4980
agcgggctgt cctctggaca accaggtgtt agtggagaag catctggagt tctttatggc    5040
actagtcaac cctttggcat aactgatctg agtggagaaa catctggggt ccctgatctc    5100
agtgggcagc cttcagggtt accagggttc agtggggcaa catcaggagt ccctgacctg    5160
gtttctggta ccacgagtgg cagcggtgaa tcttctggga ttacatttgt ggacaccagt    5220
ttggttgaag tggcccctac tacatttaaa gaagaagaag cttagggtc tgtgaactc      5280 agtggcctcc cttccggaga ggcagatctg tcaggcaaat ctgggatggt ggatgtcagt    5340
ggacagtttt ctggaacagt cgattccagt gggtttacat cccagactcc ggaattcagt    5400
ggcctaccaa gtggcatagc tgaggtcagt ggagaatcct ccagagctga gattgggagc    5460
agcctgccct cggagcata ttatggcagt ggaactccat ctagtttccc cacggtctct     5520
cttgtagaca gaactttggt ggaatctgta acccaggctc caacagccca gaggcagga    5580 gaagggcctt ctggcatttt agaactcagt ggtgctcatt ctggagcacc agacatgtct    5640
ggggagcatt ctggatttct ggacctaagt gggctgcagt ccgggctgat agagcccagc    5700
ggagagccac caggtactcc atattttagt ggggattttg ccagcaccac caatgtaagt    5760
ggagaatcct ctgtagccat gggcaccagt ggagaggcct caggacttcc agaagttact    5820
ttaatcactt ctgagttcgt ggagggtgtt actgaaccaa ctatttctca ggaactaggc    5880
caaaggcccc ctgtgacaca cacaccccag cttttttgagt ccagtggaaa agtctccaca   5940
gctggggaca ttagtggagc tacccccagtg ctccctgggt ctggagtaga agtatcatca   6000
gtcccagaat ctagcagtga gacgtccgcc tatcctgaag ctgggttcgg ggcatctgcc    6060
gcccctgagg ccagcagaga agattctggg tcccctgatc tgagtgaaac cacctctgca   6120
ttccacgaag ctaaccttga gagatcctct ggcctaggag tgagcggcag cactttgaca   6180
tttcaagaag cgcaggcgtc cgctgcccca gaagtgagtg gagaatccac caccaccagt    6240
gatgtgggga cagaggcacc aggcttgcct tcagccactc ccacggcttc tggagacagg    6300
actgaaatca gcggagacct gtctggtcac acctcgcagc tgggcgttgt catcagcacc    6360
agcatcccag agtctgagtg gacccagcag acccagcgcc ctgcagagac gcatctagaa    6420
attgagtcct caagcctcct gtactcagga gaagagactc acacagtcga aacagccacc    6480
tccccaacag atgcttccat cccagcttct ccggaatgga acgtgaatc agaatcaact     6540 gctgcagacc aggaggtatg tgaggagggc tggaacaagt accagggcca ctgttaccgc    6600
cacttcccgg accgcgagac ctgggtggat gctgagcgcc ggtgtcggga gcagcagtca    6660
cacctgagca gcatcgtcac ccccgaggag caggagtttg tcaacaacaa tgcccaagac    6720
taccagtgga tcgcctgaa cgacaggacc atcgaagggg acttccgctg gtcagatgga    6780 cacccccatgc aatttgagaa ctggcgcccc aaccagcctg acaacttttt tgccgctgga    6840
gaggactgtg tggtgatgat ctggcacgag aagggcgagt ggaatgatgt tccctgcaat   6900
taccacctcc ccttcacgtg taaaaagggc acagccacca cctacaaacg cagactacag   6960
aagcggagct cacggcaccc tcggaggagc cgccccagca cagcccactg agaagagctt   7020
ccaggacgca cccaggacgc tgagcccagg agcctgccag gctgacgtgc atcccaccca   7080
gacggtgtcc tcttcttgtc gcttttttgtc atataaggaa tcccattaaa aaaaaaa      7137
```

<210> SEQ ID NO 7
<211> LENGTH: 2471
<212> TYPE: DNA
<213> ORGANISM: Homo sapiens

<400> SEQUENCE: 7

```
agaaagcgag cagccaccca gctccccgcc accgccatgg tccccgacac cgcctgcgtt    60
cttctgctca ccctggctgc cctcggcgcg tccggacagg gccagagccc gttgggctca   120
gacctgggcc cgcagatgct tcgggaactg caggaaacca acgcggcgct gcaggacgtg   180
cgggagctgc tgcggcagca ggtcagggag atcacgttcc tgaaaaacac ggtgatggag   240
tgtgacgcgt gcgggatgca gcagtcagta cgcaccggcc tacccagcgt gcggcccctg   300
ctccactgcg cgcccggctt ctgcttcccc ggcgtggcct gcatccagac ggagagcggc   360
gcgcgctgcg gcccctgccc cgcgggcttc acgggcaacg gctcgcactg caccgacgtc   420
aacgagtgca acgcccaccc ctgcttcccc cgagtccgct gtatcaacac cagcccgggg   480
ttccgctgcg aggcttgccc gccggggtac agcggcccca cccaccaggg cgtggggctg   540
gctttcgcca aggccaacaa gcaggtttgc acggacatca acgagtgtga gaccgggcaa   600
cataactgcg tccccaactc cgtgtgcatc aacacccggg gctccttcca gtgcggcccg   660
tgccagcccg gcttcgtggg cgaccaggcg tccggctgcc agcggcgcgc acagcgcttc   720
tgccccgacg gctcgcccag cgagtgccac gagcatgcag actgcgtcct agagcgcgat   780
ggctcgcggt cgtgcgtgtg tgccgttggc tgggccggca cgggatcct ctgtggtcgc   840
gacactgacc tagacggctt cccggacgag aagctgcgct gcccgagcg ccagtgccgt   900
aaggacaact gcgtgactgt gcccaactca gggcaggagg atgtggaccg cgatggcatc   960
ggagacgcct gcgatccgga tgccgacggg gacggggtcc ccaatgaaaa ggacaactgc  1020
ccgctggtgc ggaacccaga ccagcgcaac acggacgagg acaagtgggg cgatgcgtgc  1080
gacaactgcc ggtcccagaa gaacgacgac caaaaggaca cagaccagga cggccggggc  1140
gatgcgtgcg acgacgacat cgacggcgac cggatccgca accaggccga caactgccct  1200
agggtaccca actcagacca gaaggacagt gatggcgatg gtataggga tgcctgtgac  1260
aactgtcccc agaagagcaa cccggatcag gcggatgtgg accacgactt tgtgggagat  1320
gcttgtgaca gcgatcaaga ccaggatgga gacggacatc aggactctcg ggacaactgt  1380
cccacggtgc ctaacagtgc ccaggaggac tcagaccacg atggccaggg tgatgcctgc  1440
gacgacgacg acgacaatga cggagtccct gacagtcggg acaactgccg cctggtgcct  1500
aaccccggcc aggaggacgc ggacagggac ggcgtgggcg acgtgtgcca ggacgacttt  1560
gatgcagaca aggtggtaga caagatcgac gtgtgtccgg agaacgctga agtcacgctc  1620
accgacttca gggccttcca gacagtcgtg ctggacccgg agggtgacgc gcagattgac  1680
cccaactggg tggtgctcaa ccagggaagg gagatcgtgc agacaatgaa cagcgaccca  1740
ggcctggctg tgggttacac tgccttcaat ggcgtggact tcgagggcac gttccatgtg  1800
aacacggtca cggatgacga ctatgcgggc ttcatctttg gctaccagga cagctccagc  1860
ttctacgtgg tcatgtggaa gcagatggag caaacgtatt ggcaggcgaa ccccttccgt  1920
gctgtggccg agcctggcat ccaactcaag gctgtgaagt cttccacagg ccccggggaa  1980
cagctgcgga acgctctgtg gcatacagga gacacagagt cccaggtgcg gctgctgtgg  2040
aaggacccgc gaaacgtggg ttggaaggac aagaagtcct atcgttggtt cctgcagcac  2100
cggccccaag tgggctacat cagggtgcga ttctatgagg ccctgagct ggtggccgac  2160
agcaacgtgg tcttggacac aaccatgcgg ggtggccgcc tgggggtctt ctgcttctcc  2220
caggagaaca tcatctgggc caacctgcgt taccgctgca atgacaccat cccagaggac  2280
tatgagaccc atcagctgcg gcaagcctag ggaccagggt gaggaccgc cggatgacag  2340
```

```
ccaccctcac cgcggctgga tgggggctct gcacccagcc ccaaggggtg gccgtcctga   2400
gggggaagtg agaagggctc agagaggaca aaataaagtg tgtgtgcagg gaaaaaaaaa   2460
aaaaaaaaaa a                                                       2471
```

<210> SEQ ID NO 8
<211> LENGTH: 5087
<212> TYPE: DNA
<213> ORGANISM: Homo sapiens

<400> SEQUENCE: 8

```
aacgggcgcc gcggcgggga gaagacgcag agcgctgctg ggctgccggg tctcccgctt     60 cccectcctg ctccaagggc ctcctgcatg agggcgcggt agagaccegg accegegecg    120 tgctcctgcc gtttcgctgc gctccgcccg ggccggctc agccaggccc cgcggtgagc     180
catgattcgc ctcggggctc cccagacgct ggtgctgctg acgctgctcg tcgccgctgt    240
ccttcggtgt cagggccagg atgtccagga ggctggcagc tgtgtgcagg atgggcagag    300
gtataatgat aaggatgtgt ggaagccgga gccctgccgg atctgtgtct gtgacactgg    360
gactgtcctc tgcgacgaca taatctgtga agacgtgaaa gactgcctca gccctgagat    420
ccccttcgga gagtgctgcc ccatctgccc aactgacctc ccactgccca gtgggcaacc    480
aggaccaaag ggacagaaag gagaacctgg agacatcaag gatattgtag acccaaagg    540 acctcctggg cctcagggac ctgcagggga acaaggaccc agagggatc gtggtgacaa    600 aggtgaaaaa ggtgccccctg gacctcgtgg cagagatgga gaacctggga ccctggaaa    660 tcctggcccc cctggtcctc ccggcccccc tggtcccccct ggtcttggtg gaaactttgc    720
tgcccagatg gctggaggat ttgatgaaaa ggctggtggc gcccagttgg gagtaatgca    780
aggaccaatg ggccccatgg gacctcgagg acctccaggc cctgcaggtg ctcctgggcc    840
tcaaggattt caaggcaatc ctggtgaacc tggtgaacct ggtgtctctg gtcccatggg    900 tcccgtggt cctcctggtc ccctggaaa gcctggtgat gatggtgaag ctggaaaacc    960
tggaaaagct ggtgaaaggg gtccgcctg tcctcaggt gctcgtggtt cccaggaac    1020 cccaggcctt cctggtgtca aggtcacag aggttatcca ggcctggacg tgctaaggg    1080 agaggcgggt gctcctggtg tgaagggtga gagtggttcc ccgggtgaga acggatctcc    1140
gggcccaatg ggtcctcgtg gcctgcctgg tgaaagagga cggactggcc ctgctggcgc    1200
tgcgggtgcc cgaggcaacg atggtcagcc aggccccgca gggcctccgg gtcctgtcgg    1260
tcctgctggt ggtcctggct tccctggtgc cctggagcc aagggtgaag ccggccccac    1320
tggtgcccgt ggtcctgaag gtgctcaagg tcctcgcggt gaacctggta ctcctgggtc    1380
ccctgggcct gctggtgcct ccggtaaccc tggaacagat ggaattcctg gagccaaagg    1440
atctgctggt gctcctggca ttgctggtgc tcctggcttc cctgggccac ggggccctcc    1500 tggcccctcaa ggtgcaactg gtcctctggg cccgaaaggt cagacggtg aacctggtat    1560 tgctggcttc aaaggtgaac aaggccccaa gggagaacct ggccctgctg cccccaggg    1620 agccccctgga cccgctggtg aagaggcaa gagaggtgcc cgtggagagc tggtggcgt    1680 tgggcccatc ggtccccctg gagaaagagg tgctcccggc aaccgcggtt cccaggtca    1740 agatggtctg gcaggtccca agggagcccc tggagagcga gggcccagtg tcttgctgg    1800 ccccaaggga gccaacggtg accctggccg tcctggagaa cctggccttc ctggagcccg    1860
gggtctcact ggccgccctg gtgatgctgg tcctcaaggc aaagttggcc cttctggagc    1920
ccctggtgaa gatggtcgtc ctggacctcc aggtcctcag ggggctcgtg ggcagcctgg    1980
```

```
tgtcatgggt ttccctggcc ccaaaggtgc aacggtgag cctggcaaag ctggtgagaa    2040
gggactgcct ggtgctcctg gtctgagggg tcttcctggc aaagatggtg agacaggtgc    2100
tgcaggaccc cctggccctg ctggacctgc tggtgaacga ggcgagcagg gtgctcctgg    2160
gccatctggg ttccagggac ttcctggccc tcctggtccc ccaggtgaag gtggaaaacc    2220
aggtgaccag ggtgttcccg gtgaagctgg agccctggc ctcgtgggtc caggggtga     2280 acgaggtttc ccaggtgaac gtggctctcc cggtgcccag ggcctccagg gtccccgtgg    2340
cctccccggc actcctggca ctgatggtcc caaaggtgca tctggcccag caggcccccc    2400
tggggctcag ggccctccag gtcttcaggg aatgcctggc gagaggggag cagctggtat    2460
cgctgggccc aaaggcgaca ggggtgacgt tggtgagaaa ggccctgagg gagcccctgg    2520
aaaggatggt ggacgaggcc tgacaggtcc cattggcccc cctggcccag ctggtgctaa    2580
tggcgagaag ggagaagttg acctcctgg tcctgcagga agtgctggtg ctcgtggcgc    2640
tccgggtgaa cgtggagaga ctgggccccc cggaccagcg ggatttgctg ggcctcctgg    2700
tgctgatggc cagcctgggg ccaagggtga gcaaggagag gccggccaga aaggcgatgc    2760
tggtgcccct ggtcctcagg gcccctctgg agcacctggg cctcagggtc ctactggagt    2820
gactggtcct aaaggagccc gaggtgccca aggccccccg ggagccactg gattccctgg    2880
agctgctggc cgcgttggac ccccaggctc aatggcaac cctggacccc ctggtccccc    2940
tggtccttct ggaaaagatg gtcccaaagg tgctcgagga cagcggcc cccctggccg    3000 agctggtgaa cccggcctcc aaggtcctgc tggacccct ggcgagaagg gagagcctgg    3060
agatgacggt ccctctggtg ccgaaggtcc accaggtccc cagggtctgg ctggtcagag    3120
aggcatcgtc ggtctgcctg gcaacgtgg tgagagagga ttccctggct tgcctggccc    3180
gtcgggtgag cccggcaagc aggtgctcc tggagcatct ggagacagag gtcctcctgg    3240
ccccgtgggt cctcctggcc tgacgggtcc tgcaggtgaa cctggacgag agggaagccc    3300
cggtgctgat ggcccccctg gcagagatgg cgctgctgga gtcaagggtg atcgtggtga    3360
gactggtgct gtgggagctc ctggagcccc tgggccccct ggctcccctg gcccgctgg    3420 tccaactggc aagcaaggag acagaggaga agctggtgca caaggcccca tgggaccctc    3480
aggaccagct ggagcccggg gaatccaggg tcctcaaggc cccagaggtg acaaaggaga    3540
ggctggagag cctggcgaga gaggcctgaa gggacaccgt ggcttcactg gtctgcaggg    3600
tctgcccggc cctcctggtc cttctggaga ccaaggtgct tctggtcctg ctggtccttc    3660
tggccctaga ggtcctcctg gccccgtcgg tccctctggc aaagatggtg ctaatggaat    3720
ccctggcccc attgggcctc ctggtccccg tggacgatca ggcgaaaccg ccctgctgg    3780 tcctcctgga atcctggac ccctggtcc tccaggtccc cctggccctg gcatcgacat    3840
gtccgccttt gctggcttag gcccgagaga aagggcccc gacccctgc agtacatgcg    3900 ggccgaccag gcagccggtg gcctgagaca gcatgacgcc gaggtggatg ccacactcaa    3960
gtccctcaac aaccagattg agagcatccg cagccccgag ggctcccgca agaaccctgc    4020
tcgcacctgc agagacctga aactctgcca ccctgagtgg aagagtggag actactggat    4080
tgaccccaac caaggctgca ccttggacgc catgaaggtt ttctgcaaca tggagactgg    4140
cgagacttgc gtctacccca atccagcaaa cgttcccaag aagaactggt ggagcagcaa    4200
gagcaaggag aagaaacaca tctggtttgg agaaaccatc aatggtggct ccatttcag    4260 ctatggagat gacaatctgg ctcccaacac tgccaacgtc cagatgacct tcctacgcct    4320
gctgtccacg gaaggctccc agaacatcac ctaccactgc aagaacagca ttgcctatct    4380
```

```
ggacgaagca gctggcaacc tcaagaaggc cctgctcatc cagggctcca atgacgtgga    4440
gatccgggca gagggcaata gcaggttcac gtacactgcc ctgaaggatg gctgcacgaa    4500
acataccggt aagtggggca agactgttat cgagtaccgg tcacagaaga cctcacgcct    4560
ccccatcatt gacattgcac ccatggacat aggagggccc gagcaggaat cggtgtgga    4620 catagggccg gtctgcttct tgtaaaaacc tgaacccaga acaacacaa tccgttgcaa    4680 acccaaagga cccaagtact ttccaatctc agtcactcta ggactctgca ctgaatggct    4740
gacctgacct gatgtccatt catcccaccc tctcacagtt cggacttttc tccctctct    4800 ttctaagaga cctgaactgg gcagactgca aataaaatc tcggtgttct atttatttat    4860
tgtcttcctg taagaccttc gggtcaaggc agaggcagga aactaactgg tgtgagtcaa    4920 atgcccctg agtgactgcc cccagcccag gccagaagac ctcccttcag gtgccgggcg    4980
caggaactgt gtgtgtccta cacaatggtg ctattctgtg tcaaacacct ctgtattttt    5040
taaaacatca attgatatta aaaatgaaaa gattattgga aagtaca              5087

<210> SEQ ID NO 9
<211> LENGTH: 3704
<212> TYPE: DNA
<213> ORGANISM: Homo sapiens

<400> SEQUENCE: 9
ccctcaccgg gggcaggagg gaccaaggct gggcccagaa cacatagtcc tagggtaaca      60
gtgaaggggt cgtgagggga cagtgactcc cttccaaccc cttcttcata gggactgttg     120
gcaaacaaag aaaatcaact gggaaaatga agacctgctg gaaaattcca gttttcttct     180
ttgtgtgcag tttcctggaa ccctgggcat ctgcagctgt caagcgtcgc cccagattcc     240
ctgtcaattc caattctaat ggtggaaatg aactctgtcc aaagatcagg attggccaag     300
atgacttacc agggtttgat ctgatctctc agttccaggt agataaagca gcatctagaa     360
gagctatcca gagagtagtg ggatcagcta cattgcaggt ggcttacaag ttgggaaata     420
atgtagactt caggattcca actaggaatt tatatcccag tggactgcct gaagaatact     480
ccttcttgac gacgtttcga atgactggaa gcactctcaa aaagaactgg aacatttggc     540
agattcagga ttcctctggg aaggagcaag ttggcataaa gattaatggc caaacacaat     600
ctgttgtatt ttcatacaag ggactggatg gaagtctcca aacagcagcc ttttcgaatt     660
tgtcctcctt gtttgattcc agtggcata agatcatgat tggcgtggag aggagtagtg     720
ctactctttt tgttgactgc aacaggattg aatctttacc tataaagcca agaggcccaa     780
ttgacattga tggctttgct gtgctgggaa aacttgcaga taatcctcaa gtttctgttc     840
catttgaact tcaatggatg ctgatccatt gtgacccct gcggcccagg agaaaactt     900 gccatgagct gccagccaga taacgccca gccagaccac cgacgagaga ggtcccccgg     960
gtgagcaggg tcctcccggg cctccggcc cccctggagt tccaggcatc gatggcatcg    1020
acggtgaccg aggtcctaag ggccccccgg gccccccggg tcctgcaggt gaaccgggaa    1080
agccaggagc tccaggcaag cctggcacac ctggcgctga tggattaaca ggacctgatg    1140
gatcccctgg ctccattggg tcaaagggac aaaaaggaga acctggtgtg cctggatcgc    1200
gtggatttcc aggccgtggt attcctggac cccctggtcc tctgggaca gcaggactcc    1260 ctggagagct tggccgtgta ggacctgttg gtgaccctgg agaagagga ccacctggcc    1320 cccctggccc ccaggaccc agaggaacaa ttggctttca tgatggagat ccattgtgtc    1380
ccaatgcctg tccaccaggt cgctcaggat atccaggcct accaggcatg aggggtcata    1440
```

```
aaggggctaa aggagaaatt ggtgaaccag aagacaagg acacaagggt gaagaaggtg    1500
accagggaga actcggagaa gttggagctc aaggacctcc aggagcccag ggtttgcgag    1560
gcatcaccgg catagttggg acaaaggggg aaaaggtgc tcgggcttaa gatggtgaac    1620
ctgggcctca gggtcttcct ggtgcacctg gtgatcaagg acagcgagga cctccaggag    1680
aagcaggtcc caaggagat agaggggctg aaggtgctag aggaattcct ggtctccctg    1740
ggcccaaagg agacacgggt ttgccaggtg tggatggccg tgatgggatc cctggaatgc    1800
ctggaacaaa gggtgaacca ggaaaacctg ggcctcctgg tgatgcagga ttgcaggggt    1860
taccaggtgt acctggaatt cctggtgcaa agggtgttgc tggtgaaaag ggtagcacag    1920
gtgctccagg gaagcctggt cagatgggaa attcaggcaa accgggccaa caggggcctc    1980
caggagaggg gggaccccga ggaccccagg ggcttcctgg cagtagagga gaattaggac    2040
cagtgggatc cccaggccta ccaggtaaac tgggttctct gggtagccct ggcctccctg    2100
gcttgcctgg gccccctgga cttcctggaa tgaaaggtga caggggtgta gtcggtgaac    2160
cgggtccaaa gggtgaacag ggtgcctctg gtgaagaagg tgaagcagga gaaagggggg    2220
aacttggaga tataggatta cctggcccaa agggatctgc aggtaatcct ggggaacctg    2280
gcttgagagg gcctgaggga agtcgggggc ttcctggagt ggaaggacca agaggaccac    2340
ctggaccccg gggtgtgcag ggagaacagg gtgccaccgg cctgcctggt gtccagggcc    2400
ctccgggtag agcaccgaca gatcagcaca ttaagcaggt ttgcatgaga gtcatacaag    2460
aacattttgc tgagatggct gccagtctta agcgtccaga ctcaggtgcc actgggcttc    2520
ctggaaggcc tggccctcct ggtcccccccg gccctcctgg agagaatggt ttcccaggcc    2580
agatgggaat tcgtgccctt ccgggcatta aggggccccc tggtgctctt ggtttgaggg    2640
gacctaaagg tgacttggga gaaaaggggg agcgtggccc tccaggaaga ggtcccaacg    2700
gtttgcctgg agctataggt ctcccaggtg acccaggccc tgccagctat ggcagaaatg    2760
gccgagacgg tgagcgaggc cccccagggg tgcaggaat tcctggagtg cctggacccc    2820
cgggacctcc tgggcttccc ggtttctgtg agccagcctc ctgcaccatg caggctggtc    2880
agcgagcatt taacaaaggg cctgacccct gaaaggctta ctgctgcatg gctgtctgca    2940
tgaaccacgc ctggtgaagg agcctgggtg agaaacacca tccaaagctg gggcaaagat    3000
gattaccttc agcatgatta caatgtatta ccttcagtat gattacagaa gtcctacttg    3060
acaatcacat atagaagaac ggtgctattc agtaagttct ctttccttc ccttggaggg    3120 aagacagcag agtcatcagt taaaaaaaaa aaagaaaac caaacacctc ccttgaataa    3180
atttatactc ctgttcccag gatcttgagc tttagtgtgc tataccctatg tgtcttatcg    3240 tgggccactg tgccaataaa caaaaacaac tgttttggttt acctcagttg cagtagttat    3300
tttcatttag aagttgttct cagattattg tttcagttat atagaggatt actagactag    3360
ttatgaagaa accccactac attcaatgga attggtgctt aaaatctcat cgatgtgctg    3420
tctctggagt gataagaaag ggctacatct cccgaaatga tttctttacg tcatgtattg    3480
gtttccttct tcaccttgaa cttttgttga actgtatgta ctttaccccca aacctgttaa    3540 tattttgagc gcttctatgt gaaagcaaag aaataatttt aatactctgg cattcataaa    3600
ttttattgat gagattattt attttaaagg tttgaggtaa catctctggt tgtaccaaag    3660
aagaaataaa tatggtttct taatctcttg catgttttct tata               3704
```

<210> SEQ ID NO 10
<211> LENGTH: 7291
<212> TYPE: DNA

<213> ORGANISM: Homo sapiens

<400> SEQUENCE: 10

```
acacagtact ctcagcttgt tggtggaagc ccctcatctg ccttcattct gaaggcaggg      60
cccggcagag gaaggatcag agggtcgcgg ccggagggtc ccggccggtg gggccaactc     120
agagggagag gaaagggcta gagacacgaa gaacgcaaac catcaaattt agaagaaaaa     180
gcccttttgac ttttccccc tctccctccc caatggctgt gtagcaaaca tccctggcga     240
taccttggaa aggacgaagt tggtctgcag tcgcaatttc gtgggttgag ttcacagttg     300
tgagtgcggg gctcggagat ggagccgtgg tcctctaggt ggaaaacgaa acggtggctc     360
tgggatttca ccgtaacaac cctcgcattg accttcctct tccaagctag agaggtcaga     420
ggagctgctc cagttgatgt actaaaagca ctagattttc acaattctcc agagggaata     480
tcaaaaacaa cgggattttg cacaaacaga aagaattcta aaggctcaga tactgcttac     540
agagtttcaa agcaagcaca actcagtgcc ccaacaaaac agttatttcc aggtggaact     600
ttcccagaag acttttcaat actatttaca gtaaaaccaa aaaaaggaat tcagtctttc     660
cttttatcta tatataatga gcatggtatt cagcaaattg gtgttgaggt tgggagatca     720
cctgtttttc tgtttgaaga ccacactgga aaacctgccc cagaagacta tcccctcttc     780
agaactgtta acatcgctga cgggaagtgg catcgggtag caatcagcgt ggagaagaaa     840
actgtgacaa tgattgttga ttgtaagaag aaaaccacga aaccacttga tagaagtgag     900
agagcaattg ttgataccaa tggaatcacg gttttggaa caaggatttt ggatgaagaa     960
gttttttgagg gggacattca gcagtttttg atcacaggtg atcccaaggc agcatatgac    1020
tactgtgagc attatagtcc agactgtgac tcttcagcac ccaaggctgc tcaagctcag    1080
gaacctcaga tagatgagta tgcaccagag gatataatcg aatatgacta tgagtatggg    1140
gaagcagagt ataaagaggc tgaaagtgta acagagggac ccactgtaac tgaggagaca    1200
atagcacaga cggaggcaaa catcgttgat gattttcaag aatacaacta tggaacaatg    1260
gaaagttacc agacagaagc tcctaggcat gtttctggga caaatgagcc aaatccagtt    1320
gaagaaatat ttactgaaga atatctaacg ggagaggatt atgattccca gaggaaaaat    1380
tctgaggata cactatatga aaacaaagaa atagacggca gggattctga tcttctggta    1440
gatgagaatt taggcgaata tgatttttat gaatataaag aatatgaaga taaaccaaca    1500
agccccccta atgaagaatt tggtccaggt gtaccagcag aaactgatat tacagaaaca    1560
agcataaatg gccatggtgc atatggagag aaaggacaga aaggagaacc agcagtggtt    1620
gagcctggta tgcttgtcga aggaccacca ggaccagcag gacctgcagg tattatgggt    1680
cctccaggtc tacaaggccc cactggaccc cctggtgacc ctggcgatag ggccccccca    1740
ggacgtcctg gcttaccagg ggctgatggt ctacctggtc ctcctggtac tatgttgatg    1800
ttaccgttcc gttatggtgg tgatggttcc aaaggaccaa ccatctctgc tcaggaagct    1860
caggctcaag ctattcttca gcaggctcgg attgctctga gaggcccacc tggcccaatg    1920
ggtctaactg gaagaccagg tcctgtgggg ggcctggtt catctgggc caaaggtgag    1980
agtggtgatc caggtcctca gggccctcga ggcgtccagg tccccctgg tccaacggga    2040
aaacctggaa aaggggtcg tccaggtgca gatggaggaa gaggaatgcc aggagaacct    2100
ggggcaaagg gagatcgagg gtttgatgga cttccgggtc tgccaggtga caaaggtcac    2160
aggggtgaac gaggtcctca aggtcctcca ggtcctcctg gtgatgatgg aatgaggggga    2220
gaagatggag aaattggacc aagaggtctt ccaggtgaag ctggcccacg aggtttgctg    2280
```

```
ggtccaaggg gaactccagg agctccaggg cagcctggta tggcaggtgt agatggcccc    2340
ccaggaccaa aagggaacat gggtccccaa ggggagcctg ggcctccagg tcaacaaggg    2400
aatccaggac ctcagggtct tcctggtcca caaggtccaa ttggtcctcc tggtgaaaaa    2460
ggaccacaag gaaaaccagg acttgctgga cttcctggtg ctgatgggcc tcctggtcat    2520
cctgggaaag aaggccagtc tggagaaaag ggggctctgg gtcccctggt tccacaaggt    2580
cctattggat acccgggccc ccggggagta aaggagcag atggtgtcag aggtctcaag    2640
ggatctaaag gtgaaaaggg tgaagatggt tttccaggat tcaaaggtga catgggtcta    2700
aaaggtgaca gaggagaagt tggtcaaatt ggcccaagag gggaagatgg ccctgaagga    2760
cccaaaggtc gagcaggccc aactggagac ccaggtcctt caggtcaagc aggagaaaag    2820
ggaaaacttg gagttccagg attaccagga tatccaggaa gacaaggtcc aaagggttcc    2880
actggattcc ctgggtttcc aggtgccaat ggagagaaag gtgcacgggg agtagctggc    2940
aaaccaggcc ctcggggtca gcgtggtcca acgggtcctc gaggttcaag aggtgcaaga    3000
ggtcccactg ggaaacctgg gccaaggggc acttcaggtg gcgatggccc tcctggccct    3060
ccaggtgaaa gaggtcctca aggacctcag ggtccagttg gattccctgg accaaaaggc    3120
cctcctggac cacctgggaa ggatgggctg ccaggacacc ctgggcaacg tggggagact    3180
ggatttcaag caagaccgg ccctcctggg ccaggggag tggttggacc acagggacca    3240
accggtgaga ctggtccaat aggggaacgt gggcatcctg gccctcctgg ccctcctggt    3300
gagcaaggtc ttcctggtgc tgcaggaaaa gaaggtgcaa aggtgatcc aggtcctcaa    3360 ggtatctcag ggaaagatgg accagcagga ttacgtggtt tcccagggga aagaggtctt    3420
cctggagctc agggtgcacc tggactgaaa ggaggggaag gtccccaggg cccaccaggt    3480
ccagttggct caccaggaga acgtgggtca gcaggtacag ctggcccaat tggtttacca    3540
gggcgcccgg gacctcaggg tcctcctggt ccagctggag agaaaggtgc tcctggagaa    3600
aaaggtcccc aagggcctgc agggagagat ggagttcaag gtcctgttgg tctcccaggg    3660
ccagctggtc ctgccggctc ccctggggaa gacggagaca agggtgaaat tggtgagccg    3720
ggacaaaaag gcagcaaggg tgacaaggga gaaaatggcc ctccggtcc cccaggtctt    3780 caaggaccag ttggtgcccc tggaattgct ggaggtgatg gtgaaccagg tcctagagga    3840
cagcagggga tgtttgggca aaaaggtgat gagggtgcca gaggcttccc tggacctcct    3900
ggtccaatag gtcttcaggg tctgccaggc ccacctggtg aaaaaggtga aaatggggat    3960
gttggtccca tggggccacc tggtcctcca ggcccaagag gccctcaagg tcccaatgga    4020
gctgatggac cacaaggacc cccagggtct gttggttcag ttggtggtgt tggagaaaag    4080
ggtgaacctg gagaagcagg gaacccaggg cctcctgggg aagcaggtgt aggcggtccc    4140
aaaggagaaa gaggagagaa agggggaagct ggtccacctg gagctgctgg aacctccagt    4200 gccaagggc caccaggtga tgatggccct aagggtaacc cggtcctgt tggttttcct    4260 ggagatcctg gtcctcctgg ggaacctggc cctgcaggtc aagatggtgt tggtggtgac    4320
aagggtgaag atggagatcc tggtcaaccg ggtcctcctg gcccatctgg tgaggctggc    4380
ccaccaggtc ctcctggaaa acgaggtcct cctggagctg caggtgcaga gggaagacaa    4440
ggtgaaaaag gtgctaaggg ggaagcaggt gcagaaggtc ctcctggaaa accggcccaa    4500
gtcggtcctc agggacctgc aggaaagcct ggtccagaag gtcttcgggg catccctggt    4560
cctgtgggag aacaaggtct ccctggagct gcaggcaag atggaccacc tggtcctatg    4620
ggacctcctg gcttacctgg tctcaaaggt gaccctggct ccaagggtga aaagggacat    4680
```

-continued

```
cctggtttaa ttggcctgat tggtcctcca ggagaacaag gggaaaaagg tgaccgaggg    4740
ctccctggaa ctcaaggatc tccaggagca aaggggatgg gggaattcc tggtcctgct     4800
ggtcccttag gtccacctgg tcctccaggt ttaccaggtc tcaaggccc aagggtaac      4860
aaaggctcta ctggacccgc tggccagaaa ggtgacagtg gtcttccagg gcctcctggg    4920
tctccaggtc cacctggtga agtcattcag ccttttaccaa tcttgtcctc caaaaaaacg   4980
agaagacata ctgaaggcat gcaagcagat gcagatgata atattcttga ttactcggat    5040
ggaatggaag aaatatttgg ttccctcaat tccctgaaac aagacattga gcatatgaaa    5100
tttccaatgg gtactcagac caatccagcc cgaacttgta aagacctgca actcagccat    5160
cctgacttcc cagatggtga atattggatt gatcctaacc aaggttgctc aggagattcc    5220
ttcaaagttt actgtaattt cacatctggt ggtgagactt gcatttatcc agacaaaaaa   5280
tctgagggag taagaatttc atcatggcca aaggagaaac caggaagttg gtttagtgaa    5340
tttaagaggg gaaaactgct ttcatactta gatgttgaag gaaattccat caatatggtg    5400
caaatgacat tcctgaaact tctgactgcc tctgctcggc aaaatttcac ctaccactgt    5460
catcagtcag cagcctggta tgatgtgtca tcaggaagtt atgacaaagc acttcgcttc    5520
ctgggatcaa atgatgagga gatgtcctat gacaataatc cttttatcaa aacactgtat    5580
gatggttgtg cgtccagaaa aggctatgaa aagactgtca ttgaaatcaa tacaccaaaa    5640
attgatcaag tacctattgt tgatgtcatg atcaatgact ttggtgatca gaatcagaag    5700
ttcggatttg aagttggtcc tgtttgtttt cttggctaag attaagacaa agaacatatc    5760
aaatcaacag aaaatatacc ttggtgccac caacccattt tgtgccacat gcaagttttg    5820
aataaggatg gtatagaaaa caacgctgca tatacaggta ccatttagga ataccgatg     5880
cctttgtggg ggcagaatca catggcaaaa gctttgaaaa tcataaagat ataagttggt    5940
gtggctaaga tggaaacagg gctgattctt gattcccaat tctcaactct ccttttccta    6000
tttgaatttc tttggtgctg tagaaaacaa aaaagaaaa atatatattc ataaaaaata    6060
tggtgctcat tctcatccat ccaggatgta ctaaaacagt gtgttaata aattgtaatt    6120
attttgtgta cagttctata ctgttatctg tgtccatttc caaaacttgc acgtgtccct    6180
gaattccatc tgactctaat tttatgagaa ttgcagaact ctgatggcaa taaatatatg    6240
tattatgaaa aaataaagtt gtaatttctg atgactctaa gtcccttttct ttggttaata   6300
ataaaatgcc tttgtatata ttgatgttga agagttcaat tatttgatgt cgccaacaaa    6360
attctcagag gcaaaaatc tggaagactt ttggaagcac actctgatca actcttctct    6420
gccgacagtc attttgctga atttcagcca aaaatattat gcattttgat gctttattca    6480
aggctatacc tcaaactttt tcttctcaga atccaggatt tcacaggata cttgtatata    6540
tggaaaacaa gcaagtttat attttttggac agggaaatgt gtgtaagaaa gtatattaac   6600
aaatcaatgc ctccgtcaag caaacaatca tatgtatact ttttttctac gttatctcat    6660
ctccttgttt tcagtgtgct tcaataatgc aggttaatat taagatgga aattaagcaa    6720
ttatttatga atttgtgcaa tgttagattt tcttatcaat caagttcttg aatttgattc    6780
taagttgcat attataacag tctcgaaaat tattttactt gcccaacaaa tattactttt    6840
ttcctttcaa gataatttta taatcatttt gacctaccta attgctaaat gaataacata    6900
tggtggactg ttattaagag tattttgtttt aagtcattca ggaaaatcta aactttttt    6960
tccactaagg tatttacttt aaggtagctt gaaatagcaa tacaatttaa aaattaaaaa    7020
ctgaattttg tatctatttt aagtaatata tgtaagactt gaaaataaat gttttatttc    7080
```

```
ttatataaag tgttaaatta attgatacca gatttcactg gaacagtttc aactgataat      7140
ttatgacaaa agaacatacc tgtaatattg aaattaaaaa gtgaaatttg tcataaagaa      7200
tttcttttat ttttgaaatc gagtttgtaa atgtccttt  aagaagggag atatgaatcc      7260
aataaataaa ctcaagtctt ggctacctgg a                                    7291

<210> SEQ ID NO 11
<211> LENGTH: 1538
<212> TYPE: DNA
<213> ORGANISM: Homo sapiens

<400> SEQUENCE: 11
ccgtgcaccg tgtgtgcgcg cggcgttgaa atgccctgca cgtcgggca  gcgggacaga       60 tcccagggtg cccagggagt ctccaagtgc ctcactcctc ccgccgcaaa catgacagag      120
aactccgaca aagttcccat tgccctggtg ggacctgatg acgtggaatt ctgcagcccc      180
ccggcgtacg ctacgctgac ggtgaagccc tccagcccg  cgcggctgct caaggtggga      240
gccgtggtcc tcatttcggg agctgtgctg ctgctctttg gggccatcgg ggccttctac      300
ttctggaagg ggagcgacag tcacatttac aatgtccatt acaccatgag tatcaatggg      360
aaattacaag atgggtcaat ggaaatagac gctgggaaca acttggagac ctttaaaatg      420
ggaagtggag ctgaagaagc aattgcagtt aatgatttcc agaatggcat acaggaatt      480 cgttttgctg gaggagagaa gtgctacatt aaagcgcaag tgaaggctcg tattcctgag      540
gtgggcgccg tgaccaaaca gagcatctcc tccaaactgg aaggcaagat catgccagtc      600
aaatatgaag aaaattctct tatctgggtg gctgtagatc agcctgtgaa ggacaacagc      660
ttcttgagtt ctaaggtgtt agaactctgc ggtgaccttc ctatttttctg gcttaaacca      720 acctatccaa agaaatcca  gagggaaaga agagaagtgg taagaaaaat tgttccaact      780
accacaaaaa gaccacacag tggaccacgg agcaacccag gcgctggaag actgaataat      840
gaaaccagac ccagtgttca agaggactca caagccttca atcctgataa tccttatcat      900
cagcaggaag gggaaagcat gacattcgac cctagactgg atcacgaagg aatctgttgt      960
atagaatgta ggcggagcta cacccactgc cagaagatct gtgaacccct ggggggctat     1020
tacccatggc cttataatta tcaaggctgc cgttcggcct gcagagtcat catgccatgt     1080
agctggtggg tggcccgtat cttgggcatg gtgtgaaatc acttcatata tcatgtgctg     1140
taaaataaga actagctgaa gagacaacca agaagcatt  aaggcaggtt gatgctgatg     1200
ggaccataaa atattttac  actcaacctg agcggttatt cttgacactc ttaacagaat     1260
tttttcaatt gttttccaga actttagtat atgcaaatgt actgaaaggg tagttcaagt     1320
ctaaaatgcc ataaccccctt tattatttgt tattttttat ttgcattgct ttgccataag     1380
tcttcccttg cttgtatctt ccaaagctat tttgaaataa acatgaaaat ttacagtttg     1440
ccaaaaaaaa aaaaaaaaa  aaaaaaaaa  aaaaaaaaa  aaaaaaaaa  aaaaaaaaa      1500 aaaaaaaaa  aaaaaaaaa  aaaaaaaaa  aaaaaaa                              1538

<210> SEQ ID NO 12
<211> LENGTH: 1135
<212> TYPE: DNA
<213> ORGANISM: Homo sapiens

<400> SEQUENCE: 12
gggcagaggg aataagaggc tgcctctgcc caccagtcct gccgcccagg acccgcagca       60
gagacgacgc ctgcagcaag gagaccagga aggggtgaga caaggaagag gatgtctgag      120
```

```
ctggagaagg ccatggtggc cctcatcgac gttttccacc aatattctgg aagggaggga      180
gacaagcaca agctgaagaa atccgaactg aaggagctca tcaacaatga gctttcccat      240
ttcttagagg aaatcaaaga gcaggaggtt gtggacaaag tcatggaaac actggacaat      300
gatggagacg gcgaatgtga cttccaggaa ttcatggcct tgttgccat ggttactact       360 gcctgccacg agttctttga acatgagtga gattagaaag cagccaaacc tttcctgtaa      420
cagagacggt catgcaagaa agcagacagc aagggcttgc agcctagtag gagctgagct      480
ttccagccgt gttgtagcta attaggaagc ttgatttgct ttgtgattga aaaattgaaa      540 acctcttttcc aaaggctgtt ttaacggcct gcatcattct ttctgctata ttaggcctgt     600
gtgtaagctg actggcccca gggactcttg ttaacagtaa cttaggagtc aggtctcagt      660
gataaagcgt gcaccgtgca gcccgccatg gccgtgtaga ccctaacccg gagggaaccc     720
tgactacaga aattaccccg ggcaccctt aaaacttcca ctacctttaa aaacaaagc        780 cttatccagc attatttgaa aacactgctg ttctttaaat gcgttcctca tccatgcaga     840
taacagctgg ttggccggtg tggccctgca agggcgtggt ggcttcggcc tgcttcccgg    900
gatgcgcctg atcaccaggt gaacgctcag cgctggcagc gctcctggaa aaagcaactc   960
catcagaact cgcaatccga gccagctctg ggggctccag cgtggcctcc gtgacccatg   1020
cgattcaagt cgcggctgca ggatccttgc ctccaacgtg cctccagcac atgcggcttc  1080
cgagggcact accgggggct ctgagccacc gcgagggcct gcgttcaata aaaag         1135

<210> SEQ ID NO 13
<211> LENGTH: 2889
<212> TYPE: DNA
<213> ORGANISM: Homo sapiens

<400> SEQUENCE: 13
ctggctgccg gctgctgcca ccgcaatccc ggctcctaaa tcagcgcggg gaggcgctcc      60
ctccccacgc ccggctctcc gggctctcgg ggccgcgatt ggccgcgccg cgccccccca     120
ccccgggccc ccggctccag ctgccgcgcg attggctgcg ggcctccgcc agcctttaca     180
taagaccggg cgcgctcgag tggagttgta taaagcgagc gcgcggcgtc ggggcgggag     240
gctcgaggcc agcccgggac cggggctggg agcaagcagg cggcggcgcc ggcggcagag     300
gcggcagcga gcgcccgctt ccacgccccc taggcggcgg ggccgagagc gggaggatgg     360
ctccgagcgc tgaccccggc atgtccagga tgttaccgtt cctgctgctg ctctggtttc     420
tgcccatcac tgagggtcc cagcgggctg aacccatgtt cactgcagtc accaactcag     480
ttctgcctcc tgactatgac agtaatccca cccagctcaa ctatggtgtg cagttactg      540 atgtggacca tgatgggga tttgagatcg tcgtggcggg gtacaatgga cccaacctgg     600
ttctgaagta tgaccgggcc cagaagcggc tggtgaacat cgcggtcgat gagcgcagct     660
caccctacta cgcgctgcgg gaccggcagg ggaacgccat cggggtcaca gcctgcgaca     720
tcgacgggga cggccgggag gagatctact tcctcaacac caataatgcc ttctcggggg    780
tggccacgta caccgacaag ttgttcaagt tccgcaataa ccgtgggaa gacatcctga    840 gcgatgaggt caacgtggcc cgtggtgtgg ccagcctctt gccggacgc tctgtggcct    900 gtgtggacag aaagggctct ggacgctact ctatctacat tgccaattac gcctacggta   960
atgtgggccc tgatgccctc attgaaatgg accctgaggc cagtgacctc tcccggggca  1020
ttctggcgct cagagatgtg gctgctgagg ctggggtcag caaatataca ggggccgag   1080 gcgtcagcgt gggcccatc ctcagcagca gtgcctcgga tatcttctgc gacaatgaga  1140
```

```
atgggcctaa cttccttttc cacaaccggg gcgatggcac ctttgtggac gctgcggcca    1200
gtgctggtgt ggacgacccc caccagcatg ggcgaggtgt cgccctggct gacttcaacc    1260
gtgatggcaa gtggacatc gtctatggca actggaatgg cccccaccgc ctctatctgc     1320
aaatgagcac ccatgggaag gtccgcttcc gggacatcgc ctcacccaag ttctccatgc    1380
cctcccctgt ccgcacggtc atcaccgccg actttgacaa tgaccaggag ctggagatct    1440
tcttcaacaa cattgcctac cgcagctcct cagccaaccg cctcttccgc gtcatccgta    1500
gagagcacgg agacccctc atcgaggagc tcaatcccgg cgacgccttg gagcctgagg     1560
gccggggcac aggggtgtg gtgaccgact cgacggaga cgggatgctg acctcatct       1620
tgtcccatgg agagtccatg gctcagccgc tgtccgtctt ccggggcaat cagggcttca    1680
acaacaactg gctgcgagtg gtgccacgca cccggtttgg ggcctttgcc aggggagcta    1740
aggtcgtgct ctacaccaag aagagtgggg cccacctgag gatcatcgac ggggctcag     1800
gctacctgtg tgagatggag cccgtggcac actttggcct ggggaaggat gaagccagca    1860
gtgtggaggt gacgtggcca gatggcaaga tggtgagccg gaacgtggcc agcggggaga    1920
tgaactcagt gctggagatc ctctacccc gggatgagga cacacttcag gacccagccc     1980
cactggagtg tggccaagga ttctcccagc aggaaaatgg ccattgcatg gacaccaatg    2040
aatgcatcca gttcccattc gtgtgccctc gagacaagcc cgtatgtgtc aacacctatg    2100
gaagctacag gtgccggacc aacaagaagt gcagtcgggg ctacgagccc aacgaggatg    2160
gcacagcctg cgtggggact ctcggccagt caccgggccc ccgccccacc accccaccg     2220
ctgctgctgc cactgccgct gctgctgccg ctgctggagc tgccactgct gcaccggtcc    2280
tcgtagatgg agatctcaat ctggggtcgg tggttaagga gagctgcgag cccagctgct    2340
gagcagggt gggacatgaa ccagcggatg gagtccagca ggggagtggg aaagtgggct    2400
tgtgctgctg cctagacagt agggatgtaa aggcctggga gctagaccct ccccaagccc    2460
atccatgcac attacttagc taacaattag ggagactcgt aaggccaggc cctgtgctgg    2520
gcacatagct gtgatcacag cagacagggt cgctgccctg atggcgctta cattccagtg    2580
ggtctaatga ccatatctta ggacacagat gtgcccaggg aggtggtgtc actgcacagg    2640
aagtatgagg actttagtgt cctgagttca aatcctgatt caggaactca caaagctatg    2700
tgaccttaca ccagtcactt aacttgttag ccatccatta tcgcatctgc aaaatgggga    2760
ttaagaatag aatcttgggg ttagtgtgga gattagatta aatgtatgta agacacttgg    2820
cacaaaacct ggcacatagt aaaggctcaa taaaaacaag tgcctctcac tgggctttgt    2880
caacacgtg                                                           2889
```

<210> SEQ ID NO 14
<211> LENGTH: 3935
<212> TYPE: DNA
<213> ORGANISM: Homo sapiens

<400> SEQUENCE: 14

```
ggagagccga aagcggagct cgaaactgac tggaaacttc agtggcgcgg agactcgcca      60
gtttcaaccc cggaaacttt tctttgcagg aggagaagag aaggggtgca agcgccccca    120
cttttgctct ttttcctccc ctcctcctcc tctccaattc gcctcccccc acttggagcg    180
ggcagctgtg aactggccac cccgcgcctt cctaagtgct cgccgcggta gccggccgac    240
gcgccagctt cccgggagc gcttgctcc gcatccgggc agccgagggg agaggagccc      300
gcgcctcgag tccccgagcc gccgcggctt ctcgcctttc ccggccacca gccccctgcc    360
```

| | |
|---|---|
| ccgggcccgc gtatgaatct cctggacccc ttcatgaaga tgaccgacga gcaggagaag | 420 |
| ggcctgtccg gcgcccccag ccccaccatg tccgaggact ccgcgggctc gccctgcccg | 480 |
| tcgggctccg gctcggacac cgagaacacg cggccccagg agaacacgtt ccccaagggc | 540 |
| gagcccgatc tgaagaagga gagcgaggag gacaagttcc ccgtgtgcat ccgcgaggcg | 600 |
| gtcagccagg tgctcaaagg ctacgactgg acgctggtgc ccatgccggt gcgcgtcaac | 660 |
| ggctccagca gaacaagcc gcacgtcaag cggcccatga acgccttcat ggtgtgggcg | 720 |
| caggcggcgc gcaggaagct cgcggaccag tacccgcact gcacaacgc cgagctcagc | 780 |
| aagacgctgg gcaagctctg gagacttctg aacgagagcg agaagcggcc cttcgtggag | 840 |
| gaggcggagc ggctgcgcgt gcagcacaag aaggaccacc cggattacaa gtaccagccg | 900 |
| cggcggagga agtcggtgaa gaacgggcag gcggaggcag aggaggccac ggagcagacg | 960 |
| cacatctccc ccaacgccat cttcaaggcg ctgcaggccg actcgccaca ctcctcctcc | 1020 |
| ggcatgagcg aggtgcactc ccccggcgag cactcggggc aatcccaggg cccaccgacc | 1080 |
| ccacccacca ccccaaaac cgacgtgcag ccgggcaagg ctgacctgaa gcgagagggg | 1140 |
| cgccccttgc cagaggggg cagacagccc cctatcgact ccgcgacgt ggacatcggc | 1200 |
| gagctgagca gcgacgtcat ctccaacatc gagaccttcg atgtcaacga gtttgaccag | 1260 |
| tacctgccgc ccaacggcca cccggggggtg ccggccacgc acggccaggt cacctacacg | 1320 |
| ggcagctacg gcatcagcag caccgcggcc accccggcga gcgcgggcca cgtgtggatg | 1380 |
| tccaagcagc aggcgccgcc gccacccccg cagcagcccc cacaggcccc gccggccccg | 1440 |
| caggcgcccc cgcagccgca ggcggcgccc ccacagcagc cggcggcacc cccgcagcag | 1500 |
| ccacaggcgc acacgctgac cacgctgagc agcgagccgg gccagtccca gcgaacgcac | 1560 |
| atcaagacgg agcagctgag ccccagccac tacagcgagc agcagcagca ctcgccccaa | 1620 |
| cagatcgcct acagcccctt caacctccca cactacagcc cctcctaccc gcccatcacc | 1680 |
| cgctcacagt acgactacac cgaccaccag aactccagct cctactacag ccacgcggca | 1740 |
| ggccagggca ccggcctcta ctccaccttc acctacatga accccgctca gcgccccatg | 1800 |
| tacacccca tcgccgacac ctctggggtc ccttccatcc cgcagaccca cagccccag | 1860 |
| cactgggaac aacccgtcta cacacagctc actcgacctt gaggaggcct cccacgaagg | 1920 |
| gcgaagatgg ccgagatgat cctaaaaata accgaagaaa gagaggacca accagaattc | 1980 |
| cctttggaca tttgtgttt tttgtttttt tatttgttt tgtttttct tcttcttctt | 2040 |
| cttccttaaa gacatttaag ctaaaggcaa ctcgtaccca aatttccaag acacaaacat | 2100 |
| gacctatcca agcgcattac ccacttgtgg ccaatcagtg gccaggccaa ccttggctaa | 2160 |
| atggagcagc gaaatcaacg agaaactgga ctttttaaac cctcttcaga gcaagcgtgg | 2220 |
| aggatgatgg agaatcgtgt gatcagtgtg ctaaatctct ctgcctgttt ggactttgta | 2280 |
| attatttttt tagcagtaat taagaaaaa agtcctctgt gaggaatatt ctctatttta | 2340 |
| aatatttta gtatgtactg tgtatgattc attaccattt tgagggatt tatacatatt | 2400 |
| tttagataaa attaaatgct cttatttttc caacagctaa actactctta gttgaacagt | 2460 |
| gtgccctagc ttttcttgca accagagtat ttttgtacag atttgctttc tcttacaaaa | 2520 |
| agaaaaaaaa aatcctgttg tattaacatt taaaaacaga atttgtgttat gtgatcagtt | 2580 |
| ttgggggtta actttgctta attcctcagg ctttgcgatt taaggaggag ctgccttaaa | 2640 |
| aaaaaataaa ggcctatttt tgcaattatg ggagtaaaca atagtctaga gaagcatttg | 2700 |
| gtaagcttta tcatatatat atttttttaaa gaagagaaaa acaccttgag ccttaaaacg | 2760 |

```
gtgctgctgg gaaacatttg cactcttttα gtgcatttcc tcctgccttt gcttgttcac    2820
tgcagtctta agaagaggt aaaggcaag caaaggagat gaaatctgtt ctgggaatgt      2880
ttcagcagcc aataagtgcc cgagcacact gcccccggtt gcctgcctgg ccccatgtg    2940 gaaggcagat gcctgctcgc tctgtcacct gtgcctctca gaacaccagc agttaacctt   3000
caagacattc cacttgctaa aattatttat tttgtaagga gaggttttaa ttaaaacaaa   3060
aaaaaattct tttttttttt tttttccaat tttaccttct ttaaaatagg ttgttggagc   3120
tttcctcaaa gggtatggtc atctgttgtt aaattatgtt cttaactgta accagttttt   3180
ttttatttat ctcttταatc ttttttταtt attaaaagca agtttctttg tattcctcac   3240
cctagatttg tataaatgcc ttttttgtcca tcccttttττ ctttgttgtt tttgttgaaa  3300
acaaactgga aacttgtttc tttttttgta taaatgagag attgcaaatg tagtgtatca   3360
ctgagtcatt tgcagtgttt tctgccacag accttτgggc tgccttatat tgtgtgtgtg   3420
tgtgggtgtg tgtgtgtttt gacacaaaaa caatgcaagc atgtgtcatc catatttctc    3480
tacatcttct cttggagtga gggaggctac ctggagggga tcagcccact gacagacctt   3540
aatcttaatt actgctgtgg ctagagagtt tgaggattgc tttttaaaaa agacagcaaa    3600
cttttttttt tatttaaaaa aagatatatt aacagtttta gaagtcagta gaataaaatc   3660
ttaaagcact cataatatgg catccttcaa tττctgtata aaagcagatc ttττtaaaaa   3720 gatacttctg taacttaaga aacctggcat ttaaatcata ttττgtcttt aggtaaaagc   3780 tttggtττgt gττcgtgτττ tgττtgτττc acττgτττcc ctcccagccc caaacctττt  3840 gττcτctccg τgaaacττac cτττcccτττ ττcτττcτcτ ττττττττττ τgτατατται    3900

τgτττacaaτ aaaτaτacaτ τgcaττaaaa agaaa                              3935

<210> SEQ ID NO 15
<211> LENGTH: 8034
<212> TYPE: DNA
<213> ORGANISM: Homo sapiens

<400> SEQUENCE: 15
cttgagtgtt agagctgagt agttttccca gaatctctaa gtccttttta tgctctttta     60
tgaatgaata gaattagtaa aagataaata aatttttttct tttggatttc ttaaccagtg   120
gaaaaaatgt tgacttτaaa agttcataaa atcaaatttt gcttaagaat atgttatttc   180
cacttgtgag gccagcctgg tagacctctg ggatccttττ ctgττcactc acacaccact   240 gagataagga gtgaagtgtg ggctaaatag ggctgaggct tgggcaaggg catttctgcc   300
agagcaccag agacgtcagc atctcaaggg cactgtggta tggaaaagga cgccacatga  360 gtaaattttα aaaatataaa tattttaaag ggtaaaaatg agggtccctg tatttgagga   420
tataaaagat gaaactgaag aagaaaagat aggggaagaa gaaatgaag aagaccaggt    480 cttctataag cctgttattg aagcttaag catggaattg ccagaaaat gcacggaact    540 cattagcgat atccgttata agaagagtt taaaaagtcc aaggataagt gtacatttgt    600
gactgacagt cctatgctaa accatgtaaa aaatatcggt gctttτaτττ ctgaggcaaa   660 atacaaaggc accattaaag ctgaccttτc taattctctt tataagcgga tgccagccac   720
aattgacagt gttttτgcag gagaagττac acagcτccag agτgaggτgg cctacaagca   780 gaaacatgat gctgccaaag gattctcaga ttatgcccac atgaaggagc ccctgaggt    840 taaacatgcc atggaggtca ataaacacca gagtaatatt τcτtατagga aagacgτgca    900 ggacacccac acgtacagtg cagaacττga ccgaccagac atcaagatgg caacccagaτ   960
```

```
ctctaagatc ataagcaatg cagaatacaa gaaaggacaa ggaataatga ataaagagcc      1020
cgctgtaatt ggaagaccag attttgaaca tgccgtggaa gcttctaaac tttctagtca      1080
aattaaatac aaagaaaaat tcgataatga aatgaaggat aagaaacatc attacaatcc      1140
tcttgaaagt gcttctttta ggcagaatca gcttgctgct acactggcga gcaatgtgaa      1200
gtacaagaaa gacattcaaa atatgcatga tccagtttca gatctcccaa atttgttgtt      1260
tttagaccat gttttgaaag ccagcaaaat gctcagcggc cgagaatata aaaagctctt      1320
tgaggaaaac aaaggaatgt atcattttga tgcagatgct gtggaacatc tgcaccataa      1380
aggcaatgcc gtcctccaaa gtcaggtgaa atataaagaa gaatatgaga aaaataaggg      1440
aaagccaatg cttgaatttg ttgagacacc atcatatcaa gcttcaaagg aggctcaaaa      1500
gatgcaaagt gaaaaagttt acaaagagga ttttgagaag gagattaaag gaaggtcatc      1560
actggattta gacaagactc cagaattttt acatgtaaag tacatcacca accttctgag      1620
ggagaaagaa tataaaaaag atttggaaaa tgagataaaa gggaaaggaa tggaacttaa      1680
ttcagaagtt cttgatatcc aaagagcaaa gcgggcctct gaaatggcaa gtgagaaaga      1740
atacaagaaa gacctggagt caataattaa agggaaagga atgcaagctg gcactgacac      1800
ccttgaaatg cagcatgcca agaaggctgc agagatagcg agtgagaaag actataaaag      1860
agatctggag actgaaatta aagggaaagg gatgcaggtg agcacagaca ctcttgatgt      1920
ccagagagct aagaaagcat ccgagatggc cagccagaaa caatacaaga aggacttaga      1980
aaatgaaatt aaagggaaag gaatgcaagt gagcatggat atcccagata tccttcgagc      2040
caagaggaca tctgaaatct atagccagag aaagtataaa gatgaagcag agaagatgct      2100
ttctaactat tctaccatag cagatactcc tgaaattcag agaattaaga caactcaaca      2160
aaacattagt gcggtatttt ataagaaaga agtgggagct ggcactgcag tgaaagatag      2220
cccagagatc gaacgagtga agaaaaatca gcagaatatt agttcagtga aatacaaaga      2280
agagattaaa catgcaacag ccatttctga tcctccagaa ctaaagagag ttaaagaaaa      2340
ccagaagaac atcagcaatc tccagtataa agagcaaaac tacaaggcca ctccggtaag      2400
catgaccccg gagatagaga gagtgaggcg aaaccaggag cagctgagtg cggtaaaata      2460
taagggagaa cttcaacggg gaactgcaat ttctgatcca ccagagctga gagggcaaa      2520 agaaaaccag aaaaacatca gcaatgttta ttacagaggt cagctgggaa gagctaccac      2580
tttaagtgta actcctgaaa tggaaagagt gaagaagaat caagaaaata ttagctcggt      2640
aaaatatacc caggaccata acagatgaa aggtagacca agtctgattt tagatacacc      2700
tgctatgaga catgttaaag aagcacaaaa tcatatttca atggtaaaat accatgaaga      2760
ttttgaaaaa acaaagggga gaggctttac tcccgtcgtg gacgatcctg tgacagagag      2820
agtgaggaag aacacccagg tggtcagcga tgctgcctat aaaggggtcc accctcacat      2880
cgtggagatg gacaggagac ctggaatcat tgttgacctc aaagtttggc gcacagatcc      2940
tggctccatc ttcgaccttg atcccctgga agacaatatt cagtctagaa gtctccatat      3000
gctctctgaa aaggcgagtc actataggcg acactggtct cgatcccatt ccagcagtac      3060
tttcggtaca ggtctcggag acgacaggtc agaaatctcc gagatttacc ctagcttttc      3120
atgctgcagt gaggtaacaa gaccgtctga tgaaggagca cctgttcttc ccggagccta      3180
tcagcaaagc cattcccaag gctatggcta catgcaccag accagtgtgt catccatgag      3240
atcaatgcag cattcaccaa atctaaggac ctaccgagcc atgtacgatt acagtgccca      3300
ggatgaagac gaggtctcct ttagagacgg cgactacatc gtcaacgtgc agcctattga      3360
```

```
cgatggctgg atgtacggca cagtgcagag aacagggaga acaggaatgc tcccagcgaa    3420
ttacattgag tttgttaatt aattatttct ccctgcccct tgagctttat tctaatgtat    3480
cccaaaccta atcttttaa aagatagaag atacttttaa gacaacttgg ccattatttt     3540
acaatgatgt atccttcctt tgacaattag acacacaggt accaggaaga aggaatgacc    3600
tctgggctga aaacagcagc attttcagta attcctacaa acaaaaatct tgtgtctgg     3660 acgcctggtg ctgctaattg tgttcatggt ttcctttgat tggctattga acccttctgg    3720
gaaatgtatt tttgtagact ttaatagaga agttgattgt cccttaaatg tagcgtgtgt    3780
ttgaaacttc ttagctgtca ctttggaatc accccaagcc aattctctta actctgtaat    3840
gcagccaata atacaaaccc gttttgcttt tgagtcatga ggcaatttcc aatattagtg    3900
aaaattgccc aatataataa gtgtaaacag tggcagaagg acagtctggt taaaattata    3960
ttgactggtg gccttaggga tctagaaact tctactaaac agagaaattt ccttgttccc    4020
taggctgact ggtatctatt tatttctcat ttgtaccaag gcatctccta ctctccattt    4080
atattctatg acccaagtc tatgctcagt tccacagaat gtcaggacca ataacttca     4140 cagctactct gcaaagggca aattataatg tcattgatat aatttcccta gtagcattta    4200
ccctgttgca tgtcatgtag attcaagctt ctgtaacata ggcagctgca ctgcgcgttc    4260
ctattattga agcaaaaagg gtgactgata cctaaaagcc ctttcttcct ctagtcgcca    4320
gctcatcaga aaacatact tgaaaagat gcttgagatt ttcctgctgc atcgcactct     4380
agtttggaag gatttacatc ttaggaaata acatgtatac tctagtaaat aagcgattta    4440
ggtgttccat tgaacagctt tgattaactt aatgccacca ttgatttcaa agtgaagaaa    4500
atgtaacaga agccagtgaa gcaatggaag ctggagtgtg actggaaaaa tactcagcaa    4560
acaaagttac caattccata cagagatgat ctggtgtctt cttttggaaa atggtattca    4620
aattctggaa tggaaatcta gccaccaaaa cgggttaatc aaaagacgtc cttttccgtt    4680 tttttgctt ttattttcta aatcatttt aagggaatga acaggaatg tcatcagaga       4740 tttttagta caggcccaag agcctgtact ctaagaaaga aatttttgcc atgtatgaat     4800
tttcgaataa gtgactttgc aggcttttgc tagcccttgc tggtgggtct ggaaattaca    4860
tccagagtct gcagtccagg tcaccaagcc agcggcaccc gtcggcaacc ctgtgtttaa    4920
cggattgtgc cgtttactgt gacctgcaac ggggtggcat tcacttaggg tctgacttca    4980
cagctatgac aaaaccgaaa aagcaaaact gcgaggaagt gctaagatgt acgggtcttg    5040
gggatatctg cctatatgt tatattcaag gaaattaacg aaacatcctg tgaaacatcg      5100
tttaaggaaa cgtttactag tccaaaggcc aaagctaatt tatttccact ttagaaaagt    5160
tagcacatgc ttttgaaaat ctgtgatttc attttattag gctaaagggg taaataggct    5220
ttattacact gaagctgcat ctatatgtca ctgacataaa gttgaaaaaa taaatgcagg    5280
caaataacta gagacttctt ttaagggggt ttggctggtt tctctcactg aaatggccag    5340
tcgtgattaa agtgataaaa ccccatatct gttttggtat attgtacaca aacctacaaa    5400
aataaactga acttgcaata tttttgcaat aaaatctgtc gttaaaactg aggataaaat    5460
acctgctcaa ttttatttta ctaagtatat atttacattt cacccaggca ggccatttc     5520 ttttgtgatt ataagaaaga gtagttgttg attaaatttt cagactaaat ataggacagg    5580
tacaattttg gataaatagc agatttataa gaaccgcaat gaaaactgac ttgaaataat    5640
gcttgtaatc aggaaagtaa tttcatccac cgatttcaaa accagattca ctgagcataa    5700
aagtcaatac atatttgagg aataagtctc ctaaaattt aagcttcacg taataatgtt     5760
```

```
tgcatagcaa aatatttctg cttcaagcct ttaggaatta agatctgatc agaatttaac    5820
taaagggtag ttgttttaca atgaagacta aaactgaaca agatgttgca tgcgcttagg    5880
ccataatttg gtagtgttgg cagttgttaa taaagcttgt caggatgtta agcatctcag    5940
gagaaatatt ggaaaattat atgtataaaa ccaaagtgct gttttaaaa gcatcattta     6000
aaaaaaaatg acatgcctga acaacttttc cactttccac gtgcttccct cccacctttg    6060
gtttggcaac aggtatctcg tgcatgaagc tgacagctaa agaagatttt aaaaattgag    6120
ttaaagatga ctgtgtaaat gtccaagcac agagagcatg cacctgactt tctaaagttt    6180
gatgtgttct caagcctgac agaagcacaa ggaacagttt gatacacttt taaaaggttc    6240
tgaaaacaaa gctgtatagg gatcctctct ctcttgagca aagtatagca acagaatata    6300
ttgcttttgt tgtaagcttt tgtagtacat gttttactaa ataattcttg ttctctagaa    6360
agctttctat ttctaaccta tggcaaaatg aatccttcat gtcttcttgt tattgtttac    6420
acacttgcag tgtagcccag tttgaaatat ttatttggtt atcaactgcc catggaggag    6480
gctcttgatg atcccaggtc tcctcgacct ccatacacca cacaggcatt tgtaagcaca    6540
gtttccacaa gcaccttgta ggaatatgga taagattaga ccagcccctc tctgtccact    6600
gggtttattt cttgaagaag atgcagatct ggttttttcca atgtgccaca gtcttccttt   6660
atcctctcca tgctgagctt gacaacactc tgggaatgag gaacaagact tttctaaaa    6720
agatagtgga agttcaaggg atgtacctcg ttttcaggtt catccatctc cagtggaatg    6780
ttttcaataa aagatgaaga aaatgtgtgt gatctttaat aacacatccc tatagaaagt    6840
ggataaaaga tataccaaaa ctgtaataca gatatataca aatataggtg ccttttttgat   6900
tactcttgtt tgtctagtat gctcttggaa agaaaaccaa gcaagcaagt tgctgcctat    6960
tctatagtaa tatttttatta cacatgattg atattttttgt ggtagggaag tgggatgctc   7020
ctcagatatt aaaggtgtta gctgattgta ttttatctct aaagatttag aactttagaa    7080
aatgccgact tcttccatct atttctgaaa ggttctttgt ggatttatat agagttgagc    7140
tatataaaca ttaactttag atttgggatt taaaatgcct attgtaagat agaataattg    7200
tgaggctgga ttcactacac aagatgaact tcacttcata aattaattat accttagcga    7260
tttgcttctg ataatctaaa agtggctaga ttgtggttgt tttggttaag gtgatatgga    7320
ggtgggagag cttttagtta agtaagaagc tatgtaaact gacaaggatg ctaaaataaa    7380
agtctctgaa gtattccatg cctttttggac cctttcctcg caactaactg tcaactgttg    7440
atcaaaaaag tcaaggcatt gtatgttgct tctgtggtta ttattctgtg atgcttagac    7500
tacttgaacc cataaacttg gaagaatctt tgagcaaatt ttctcagttg tctgtatgac    7560
ttcagtatat tcctgggaat gccataggat tttttgtgct tgatacatgg tatccagttt    7620
gcatagtatc acttctttgt aatccagttg ctgttaagaa tgatgtactt taaaggaaaa    7680
gagaaaactg catcacagtc ccattctcca gtgtccatgc aatgaattgc tgagcattta    7740
ggaagcagca ccaagtctat tacaggcatg gtgtgaaact tgatgtttga cctgtgatca    7800
aaattgaacc attgtacagt ttggcttctg tttgcttcaa aatatgtaga attgtggttg    7860
atgattaatt tgcgagacta actttgagag tgtaacagtt ttgaagaaaa cattgaatgt    7920
tttacaaatg aagggcttc acggaatgtt acaatgttac taatataatt tggcttttgt     7980
tatgcaaatt gttaacacca gctattaaaa tatatttttag tagaaaaaaa aaaa         8034
```

<210> SEQ ID NO 16
<211> LENGTH: 28
<212> TYPE: DNA

```
<213> ORGANISM: Artificial
<220> FEATURE:
<223> OTHER INFORMATION: HAPLN1 forward primer

<400> SEQUENCE: 16
tgaaggatta gaagatgata ctgttgtg                                        28

<210> SEQ ID NO 17
<211> LENGTH: 20
<212> TYPE: DNA
<213> ORGANISM: Artificial
<220> FEATURE:
<223> OTHER INFORMATION: HAPLN1 reverse primer

<400> SEQUENCE: 17
gccccagtcg tggaaagtaa                                                 20

<210> SEQ ID NO 18
<211> LENGTH: 18
<212> TYPE: DNA
<213> ORGANISM: Artificial
<220> FEATURE:
<223> OTHER INFORMATION: HAPLN1 probe sequence

<400> SEQUENCE: 18
tacaaggtgt ggtattcc                                                   18

<210> SEQ ID NO 19
<211> LENGTH: 22
<212> TYPE: DNA
<213> ORGANISM: Artificial
<220> FEATURE:
<223> OTHER INFORMATION: MFAP5 forward primer sequence

<400> SEQUENCE: 19
cgaggagacg atgtgactca ag                                              22

<210> SEQ ID NO 20
<211> LENGTH: 20
<212> TYPE: DNA
<213> ORGANISM: Artificial
<220> FEATURE:
<223> OTHER INFORMATION: MFAP5 reverse primer sequence

<400> SEQUENCE: 20
agcgggatca ttcaccagat                                                 20

<210> SEQ ID NO 21
<211> LENGTH: 17
<212> TYPE: DNA
<213> ORGANISM: Artificial
<220> FEATURE:
<223> OTHER INFORMATION: MFAP5 probe sequence

<400> SEQUENCE: 21
acattcacag aagatcc                                                    17

<210> SEQ ID NO 22
<211> LENGTH: 20
<212> TYPE: DNA
<213> ORGANISM: artificial
<220> FEATURE:
<223> OTHER INFORMATION: Primer sequence

<400> SEQUENCE: 22
gccaaggtgt tttcacacag                                                 20
```

```
<210> SEQ ID NO 23
<211> LENGTH: 40
<212> TYPE: DNA
<213> ORGANISM: Artificial
<220> FEATURE:
<223> OTHER INFORMATION: Primer sequence

<400> SEQUENCE: 23
taatacgact cactataggg gccaaggtgt tttcacacag                              40

<210> SEQ ID NO 24
<211> LENGTH: 20
<212> TYPE: DNA
<213> ORGANISM: Artificial
<220> FEATURE:
<223> OTHER INFORMATION: Primer sequence

<400> SEQUENCE: 24
ctctgaagca gtagacacca                                                    20

<210> SEQ ID NO 25
<211> LENGTH: 21
<212> TYPE: DNA
<213> ORGANISM: Artificial
<220> FEATURE:
<223> OTHER INFORMATION: Primer sequence

<400> SEQUENCE: 25
cctagcctgg ctttcttgct c                                                  21

<210> SEQ ID NO 26
<211> LENGTH: 41
<212> TYPE: DNA
<213> ORGANISM: Artificial
<220> FEATURE:
<223> OTHER INFORMATION: Primer sequence

<400> SEQUENCE: 26
taatacgact cactataggg cctagcctgg ctttcttgct c                            41

<210> SEQ ID NO 27
<211> LENGTH: 21
<212> TYPE: DNA
<213> ORGANISM: Artificial
<220> FEATURE:
<223> OTHER INFORMATION: Primer sequence

<400> SEQUENCE: 27
ccattgggtc tctgcaaatc c                                                  21
```

METHODS OF EVALUATING CELLS AND CELL CULTURES

This application claims the benefit of provisional application 60/910,574 filed Apr. 6, 2007, which is incorporated by reference in its entirety.

This invention relates to methods of determining the composition of a cell culture, more particularly, to methods of distinguishing between chondrocytes and fibroblasts.

Injuries to articular cartilage have poor rates of repair, in part due to the lack of blood supply in cartilage tissue (Basad et al., In: Hendrich et al., Cartilage Surgery and Future Perspectives, Thieme Verlag, 49-56 (2003)). Trauma to knee joints can result in, for example, chondral and osteochondral lesions, and such injuries may progress to osteoarthritis (Brittberg et al., New England Journal of Medicine, 331(14): 889-895 (1994)). In severe cases of osteoarthritis, a total knee replacement may be needed. However, the artificial prostheses used in knee replacements have limited lifetimes, thus knee replacements are not optimal remedies, particularly for non-elderly patients (Brittberg et al., supra).

In some cases, articular cartilage injuries may be repaired by autologous chondrocyte implantation (Brittberg et al., Clin. Orthopaed. Rel. Res., 367S: S147-S155 (1999)). In this procedure, chondrocytes are harvested from a patient, expanded in cell culture to increase the number of chondrocytes, and then implanted back into the injury site of the patient. The chondrocytes are covered with a flap of periosteal tissue to seal the chondrocytes into the injury site. Although the cultured chondrocytes have a tendency to de-differentiate in culture, in a successful implant, de-differentiated chondrocytes preserve their re-differentiation potential and will re-differentiate into chondrocytes that produce a hyaline cartilaginous tissue upon implantation.

In a modified technique known as matrix-induced autologous chondrocyte implantation (MACI® implantation procedure), cultured chondrocytes are loaded onto a collagen matrix before they are implanted into the patient (Basad et al., supra). In addition, the collagen matrix can be fixed with fibrin glue rather than suturing, making it a simpler surgical technique.

Different techniques and media can be used to culture chondrocytes. Examples of serum-free media for chondrocyte culture and methods for isolation and propagation of chondrocytes are described, for example, in U.S. Pat. Nos. 6,150,163 and 7,169,610, and in U.S. Provisional Patent Application No. 60/805,307, which are incorporated herein by reference.

Fibroblasts or fibroblast-like cells (such as synoviocytes) may be co-isolated with chondrocytes and, thus, co-propagated in a cell culture in the course of preparing chondrocyte implants. Chondrocytes are known to take on a fibroblastic appearance when they de-differentiate in culture (Benya and Shaffer, Cell, 30: 215-224 (1982)). Nevertheless, they maintain their differentiation potential, i.e., they are able to re-express a chondrocytic phenotype upon implantation. As a result, it can be difficult to distinguish cultured de-differentiated chondrocytes from co-cultured fibroblasts or fibroblast-like cells based on appearance.

In addition, gene expression patterns in cultured, de-differentiated chondrocytes are different from those of native cartilage chondrocytes. For example, many markers that are highly expressed in native cartilage chondrocytes are expressed at reduced levels in cultured chondrocytes (Binette et al., J. Orthopaed. Res., 16: 207-216 (1998)). Accordingly, expression of such a chondrocyte marker may not necessarily distinguish a de-differentiated chondrocyte from cells of other types that may be present in the cell culture. Furthermore, many known fibroblast markers are expressed in both de-differentiated chondrocytes and native cartilage chondrocytes, albeit at different levels. Accordingly, the expression level of such a fibroblast marker may not necessarily indicate whether cells present in the sample are de-differentiated chondrocytes, fibroblasts, or fibroblast-like cells.

There is a need for methods of identifying chondrocytes, fibroblasts and fibroblast-like cells, particularly, methods applicable to cell culture.

In certain aspects, the methods of the invention provide methods of evaluating the composition of a cell culture (e.g., to distinguish chondrocytes from fibroblasts) and methods for evaluating the phenotype of an individual cell (e.g., as a chondrocyte). The methods of the invention may be used, for example, for assessing chondrocyte cultures used for the treatment of cartilage defects. In some embodiments, the invention involves identifying cell culture composition or the identity of a cell based on expression level of a fibroblast marker. In other embodiments, the invention involves comparing expression levels of at least one chondrocyte marker and at least one fibroblast marker in a cell culture sample or in an individual cell. In illustrative embodiments, the chondrocyte marker is hyaluronan and proteoglycan link protein 1 (HAPLN1), and the fibroblast marker is microfibrillar associated protein 5 (MFAP5).

The invention is based, at least in part, on the identification of MFAP5 as a cell phenotype marker that is highly expressed in certain non-chondrocytic cell types, such as fibroblasts and synoviocytes, while being expressed at significantly lower levels in chondrocytes. The invention is further based, at least in part, on the finding that the expression level ratios of MFAP5 and a chondrocyte marker, such as HAPLN1, is a reliable indicator of the cell phenotype in cultures derived from cartilage biopsies. While under some conditions it may be preferable to use both types of markers (i.e., fibroblast and chondrocyte markers) in order to confirm the composition of cell culture or the phenotype of an individual cell, the invention also provides embodiments in which determining the normalized expression level of the MFAP5 marker alone may be sufficient for that purpose.

In some embodiments, the fibroblast marker is other than MFAP5 and is such that its normalized expression levels are lower in chondrocytes than in fibroblasts. In some embodiments, the fibroblast marker is such that its normalized expression levels are lower in chondrocytes (e.g., primary and/or passaged chondrocytes) than in fibroblasts and/or synoviocytes. In some embodiments, the fibroblast marker is expressed at least 2-, 5-, 8-, 10-fold lower, or less, in chondrocytes than in fibroblasts and/or synoviocytes.

Thus, in one aspect, the invention provides a method of evaluating the composition of a cell culture (Method 1), e.g., cell culture that tentatively contains chondrocytes; and a method of evaluating the phenotype of an individual cell (Method 2). In the embodiments of Method 1, the expression level of a respective marker is determined as the average expression level of that marker in a plurality of cells (e.g., culture sample). In the embodiments of Method 1, the composition of a cell culture may be evaluated as a whole to determine whether it contains chondrocytes. In the embodiments of Method 2, the expression level of a marker is determined as the expression level of that marker in the individual cell being evaluated. Thus, while Method 1 identifies the composition of the cell culture, Method 2 identifies the phenotype of an individual cell, e.g., whether or not the cell is a chondrocyte.

In some embodiments, Method 1 comprises:
a) obtaining a plurality of cells from a cell culture;
b) determining the average expression level of a fibroblast marker of the invention in a plurality of cells from the cell culture; and
c) determining the composition of the culture based on the expression level;

wherein the expression level below a predetermined threshold indicates that the cell culture contains chondrocytes. Alternatively, the expression level above a predetermined threshold indicates that the cell culture does not contain chondrocytes (e.g., the culture does not comprise at least 50%, 55%, 60%, 65%, 75%, 80%, 85%, 90%, 95%, 98%, 99% or more chondrocytes).

In some embodiments, Method 1 involves comparing expression levels of a fibroblast marker (MFAP5 or another fibroblast marker) and a chondrocyte marker (e.g., HAPLN1) to a control or to each other. In some embodiments, the fibroblast marker and the chondrocyte marker are such that the ratio of their expression levels (chondrocyte marker to fibroblast marker) in primary and/or passaged chondrocytes is equal to, or greater than, 5, 10, 20, 30, 50, 75, 100 or more times the expression ratio in cultured fibroblasts.

In particular, in some embodiments, Method 1 comprises:
a) obtaining a plurality of cells from a cell culture;
b) determining the average expression level of a chondrocyte marker in the plurality of cells;
c) determining the average expression level of a fibroblast marker in the plurality of cells; and
d) determining the composition of the culture based on the average expression level of the chondrocyte marker and the average expression level of the fibroblast marker.

In some embodiments, the culture is identified as containing chondrocytes if the expression level of the chondrocyte marker is above a predetermined threshold, while the expression level of the fibroblast marker is below a predetermined threshold. Alternatively, the expression level of the fibroblast marker above a predetermined threshold indicates that the cell culture does not contain chondrocytes (e.g., the culture does not comprise at least 50%, 55%, 60%, 65%, 75%, 80%, 85%, 90%, 95%, 98%, 99% or more chondrocytes).

In some embodiments, the step of determining the culture composition includes comparing the average expression levels of the chondrocyte marker and the average expression level of the fibroblast marker. In some embodiments, the markers' expression levels are compared relative to each other (thus, the thresholds may be defined, e.g., as a given difference between the expression levels of two markers, or a ratio thereof). For example, in some embodiments, a ratio of a chondrocyte marker (e.g., HAPLN1) expression level to that of a fibroblast marker (e.g., MFAP5), which is greater than a predetermined threshold, e.g., 0.25, 0.55, 1, 2, 2.2, 5, 10, 25, 50 or more, indicates that the cell culture contains chondrocytes.

In some embodiments of Method 1, the expression levels of chondrocyte and fibroblast markers are determined at the RNA level, e.g., by a standard curve method of quantitative RT-PCR or by a comparative $C_T$ method of quantitative RT-PCR (which measures the difference in the number of threshold cycles required for the fibroblast marker and the chondrocyte markers).

In a related aspect, the invention provides a method of evaluating the phenotype of an individual cell (Method 2), e.g., using flow cytometry or single-cell RT-PCR. The method is useful for identifying individual cells from a cell culture, including a cell culture derived from cartilage or synovium, a chondrocyte culture, a fibroblast culture, synoviocyte culture, or any other appropriate culture. The method is also useful for identifying individual cells derived from any appropriate biological samples in which it is desirable to identify individual cells, including cartilage samples, synovium samples, fibroblast samples, etc. The fibroblast and chondrocyte markers in Method 2 may be chosen and evaluated as described for Method 1.

In some embodiments, Method 2 comprises
a) determining the expression level of a fibroblast marker of the invention in the cell; and
b) determining the phenotype of the cell based on the expression level of the fibroblast maker;

wherein the expression level below a predetermined threshold indicates that the cell is a chondrocyte. Alternatively, the expression level above a predetermined threshold indicates that the cell is not a chondrocyte (e.g., a fibroblast or a synoviocyte). In some embodiments, Method 2 comprises:
a) determining the expression level of a chondrocyte marker in the cell;
b) determining the expression level of a fibroblast marker in the cell; and
c) evaluating the phenotype of the cell based on the expression level of the chondrocyte marker and the expression level of the fibroblast marker.

In some embodiments, the cell is identified as a chondrocyte if the expression level of the chondrocyte marker is above a predetermined threshold level, while the expression level of the fibroblast marker is below a predetermined threshold level. Alternatively, the cell is not a chondrocyte if the expression level of the chondrocyte marker is below a predetermined threshold level, while the expression level of the fibroblast marker is above a predetermined threshold level. In some embodiments, step c) of evaluating the phenotype of the cell includes comparing the expression levels of the chondrocyte marker and the expression level of the fibroblast marker.

Additional aspects of the invention will be set forth in the description that follows.

BRIEF DESCRIPTION OF THE FIGURES

In FIGS. 14A and 14B, chondrocyte strains were sampled from cartilage (culture level 0) and then cultured from primary (culture level 1) through second passage (culture level 3), as shown in the figure. The expression levels were determined by a comparative $C_T$ method of RT-PCR using custom-designed primers and probes as described in the Example 5. The HAPLN1:MFAP5 ratio was calculated as $2^{\wedge}(C_{T,MFAP5}-C_{T,HAPLN1})$.

Figure 1:
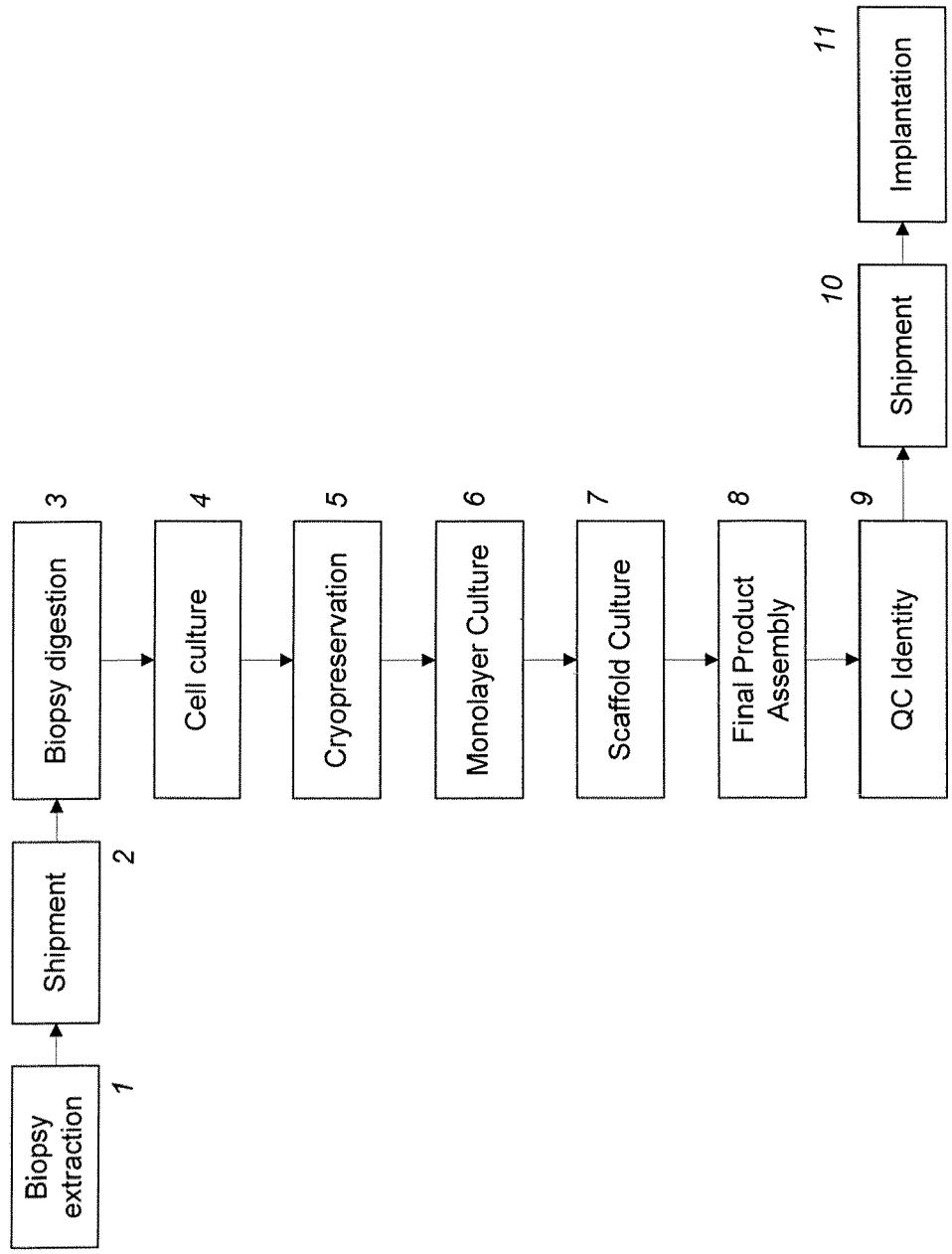
FIG. 1 is a flow diagram illustrating stages in an exemplary manufacturing process used for producing cultured chondrocytes from chondrocyte biopsies.

The invention is based, at least in part, on the identification of MFAP5 as a gene that is highly expressed in certain non-chondrocytic cell types, such as fibroblasts and synoviocytes, while being expressed at significantly lower levels in chondrocytes. Accordingly, in some embodiments the invention provides methods of using MFAP5 as a cell phenotype marker. MFAP5 is a serine-threonine-rich protein that binds to fibrillins and was reported to be involved in the stabilization of type I procollagen (Lemaire et al., Arthritis & Rheumatism, 52(6): 1812-1823 (2005)). The nucleotide and amino acid sequences of human MFAP5 can be found under GenBank® Accession No. NM_003480; its nucleotide sequence is also provided as SEQ ID NO:1. In addition to, or in place of MFAP5, other fibroblast markers can also be used in the methods of the invention, as described below.

Accordingly, in one aspect, the invention provides a method of evaluating the composition of a cell culture comprising chondrocytes (Method 1) and a method of evaluating the phenotype of an individual cell (Method 2).

In the embodiments concerning Method 1, the expression level of a respective marker is determined as the average expression level of that marker in a plurality of cells. In the embodiments of Method 1, the composition of a cell culture may be evaluated as a whole to determine whether it contains chondrocytes. In the embodiments of Method 2, the expression level of a marker is determined as the expression level of that marker in an individual cell being evaluated. Thus, while Method 1 identifies the composition of cell culture, Method 2 identifies the phenotype of an individual cell, e.g., whether or not the cell is a chondrocyte.

In some embodiments, the fibroblast marker is other than MFAP5 and is such that its normalized expression levels are lower in chondrocytes than in fibroblasts. In some embodiments, the fibroblast marker is such that its normalized expression levels are lower in chondrocytes (e.g., primary chondrocytes, cultured de-differentiated chondrocytes) than in fibroblasts (e.g. dermal fibroblasts) and/or synoviocytes. In some embodiments, the fibroblast marker is expressed at least 2-, 5-, 8-, 10-fold lower, or less, in chondrocytes than in fibroblasts and/or synoviocytes. Such additional markers can be identified using, e.g., gene array analysis, as described in, e.g., Leung et al., Trends in Genetics, 19(11): 649-659 (2003).

In some embodiments, Method 1 comprises determining the expression level of a fibroblast marker of the invention in a plurality of cells from a cell culture, wherein the expression level below a predetermined threshold indicates that the cell culture contains chondrocytes. Alternatively, the expression level above a predetermined threshold indicates that the cell culture does not contain chondrocytes (e.g., the culture does not comprise at least 50%, 55%, 60%, 65%, 75%, 80%, 85%, 90%, 95%, 98%, 99% or more chondrocytes).

In illustrative embodiments, the fibroblast marker is MFAP5, and a higher-than-threshold expression of MFAP5 by the cell culture indicates that the culture contains a substantial number of non-chondrocytes. In some embodiments, the predetermined threshold level is 1) equal to or less than that of MFAP5 expression in pure fibroblast cultures (e.g., 2-, 3-, 4-, or 5-fold lower) or 2) equal to or greater than (e.g., 2-, 3-, 4-, or 5-fold greater) the level of MFAP5 expression in pure chondrocyte cultures (e.g., primary chondrocytes obtained from cartilage biopsies). For fibroblast markers other than MFAP5, the predetermined threshold can be analogously selected based on the expression levels of the respective marker in pure fibroblasts and/or chondrocytes. The "predetermined" level does not need to be chosen prior to determining marker expression levels and may be chosen after expression levels are determined, based for example, on the statistical analysis of the expression results.

In some embodiments, Method 1 and Method 2 involve comparing expression levels of a fibroblast marker (MFAP5 or another fibroblast marker) and a chondrocyte marker (e.g., HAPLN1 or another chondrocyte marker) to a control or to each other. The order in which the expression levels of either marker are determined can vary. For example, one can first determine the expression level of a chondrocyte marker and then determine the expression level of a fibroblast marker, or vice versa. In some embodiments, the expression levels of both types of markers can be determined simultaneously.

Examples of some chondrocyte markers useful in the methods of the invention, including their GenBank™ accession numbers and SEQ ID NOs, are provided in Table 1. Thus, in some embodiments, the chondrocyte marker is chosen from HAPLN1, MGP, EDIL3, WISP3, AGC1, COMP, COL2A1, COL9A1, COL11A1, LECT1, S100B, CRTAC1, SOX9, and NEBL.

TABLE 1

Examples of chondrocyte markers

| Marker Name | GenBank ™ Accession No. | SEQ ID NO | Reference |
|---|---|---|---|
| hyaluronan and proteoglycan link protein 1 (HAPLN1) | NM_001884 | SEQ ID NO: 2 | Buckwalter et al., J. Biol. Chem., 259(9): 5361-5363 (1984) |
| matrix Gla protein (MGP) | NM_000900 | SEQ ID NO: 3 | Monroe et al., Nat Genet., 21(1): 142-4 (1999) |
| GF-like repeats and discoidin I-like domains 3 (EDIL3) | NM_005711 | SEQ ID NO: 4 | Genes Dev., 12(1): 21-33 (1998) |
| WNT1 inducible signaling pathway protein 3 (WISP3) | NM_003880 | SEQ ID NO: 5 | Kutz et al., Mol. Cell. Biol., 25(1): 414-21 (2005) |
| aggrecan 1 (AGC1) | NM_001135 | SEQ ID NO: 6 | Roughley et al., Eur. Cell Mater., 11: 1-7 (2006) |
| cartilage oligomeric matrix protein (COMP) | NM_000095 | SEQ ID NO: 7 | Song et al., J. Hum. Genet., 48(5): 222-5 (2003) |
| type II collagen (COL2A1) | NM_001844 | SEQ ID NO: 8 | Nishimura et al., Hum. Mutat., 26(1): 36-43 (2005) |
| type IX collagen (COL9A1) | NM_001851 | SEQ ID NO: 9 | Czarny-Ratajczak et al., Am. J. Hum. Genet., 69(5): 969-80 (2001)) |
| type XI collagen (COL11A1) | NM_001854 | SEQ ID NO: 10 | Poulson et al., J. Med. Genet., 41(8): e107 (2004) |
| leukocyte cell derived chemotaxin 1 protein (LECT1) | NM_007015 | SEQ ID NO: 11 | Hiraki et al., Eur. J. Biochem., 260(3): 869-78 (1999) |
| S100 calcium binding protein beta (S100B) | NM_006272 | SEQ ID NO: 12 | Steffansson et al., Nature, 295(5844): 63-4 (1982) |
| cartilage acidic protein 1 (CRTAC1) | NM_018058 | SEQ ID NO: 13 | Steck et al., Biochem. J., 353: 169-174 (2001) |
| SRY-box 9 protein (SOX9) | NM_000346 | SEQ ID NO: 14 | Kou and Ikegawa, J. Biol. Chem., 279(49): 50942-8 (2004) |
| nebulette (NEBL) | NM_006393 | SEQ ID NO: 15 | Grogan et al., Arth. & Rheum., 56(2): 586-95 (2007) |

The plurality of cells from the culture under evaluation may be represented by a sample or an aliquot obtained from that culture. For example, in case of cultures grown on collagen matrices, punch sampling can be used as described in the Examples. The plurality of cells, typically, will contain at least the number of cells sufficient to conduct a given method of expression analysis, or more. For example, for PCR as few as 10-1,000 cells are usually sufficient, but a lower number can also be used.

Additional chondrocyte markers can be identified using, e.g., gene array analysis, as described in, e.g., Leung et al., Trends in Genetics, 19(11): 649-659 (2003). Generally, a chondrocyte marker is a gene or protein whose normalized expression levels are higher in chondrocytes (e.g., primary chondrocytes, cultured de-differentiated chondrocytes) than in fibroblasts (e.g. dermal fibroblasts) and/or synoviocytes. In some embodiments, the chondrocyte marker is expressed at least 2, 4, 5, 8, 10, 50, 75, 100 times or greater in chondrocytes than in fibroblasts and/or synoviocytes.

In some embodiments, the fibroblast marker and the chondrocyte marker are chosen in such a way that the ratio of their expression levels in primary chondrocytes and/or in passaged chondrocytes is equal to or greater than 5, 10, 20, 30, 50, 75, 100 or more times that in dermal fibroblasts and/or synoviocytes.

In particular, in some embodiments, Method 1 comprises:
a) obtaining a plurality of cells from a cell culture;
b) determining the average expression level of a chondrocyte marker in the plurality of cells;
c) determining the average expression level of a fibroblast marker in the plurality of cells; and
d) determining the composition of the culture based on the average expression level of the chondrocyte marker and the average expression level of the fibroblast marker.

In some embodiments, the culture is identified as containing chondrocytes if the expression level of the chondrocyte marker is above a predetermined threshold, while the expression level of the fibroblast marker is below a predetermined threshold. Alternatively, the culture does not contain chondrocytes (e.g., the culture does not comprise at least 50%, 55%, 60%, 65%, 75%, 80%, 85%, 90%, 95%, 98%, 99% or more chondrocytes) if the expression level of the chondrocyte marker is below a predetermined threshold, while the expression level of the fibroblast marker is above a predetermined threshold level.

In further embodiments of Method 1, the invention comprises a method of evaluating the composition of a cell culture, said method comprising:
a) obtaining a cartilage biopsy from a mammal;
b) isolating cells from the biopsy;
c) culturing cells isolated in step b) in a cell culture;
d) obtaining a sample of the cell culture;
e) determining the expression levels of MFAP5 and HAPLN1 in one or more cells from the sample; and
f) determining the composition of the culture based on the expression levels of MFAP5 and HAPLN1.

In some embodiments, the step of determining the culture composition comprises comparing the average expression levels of the chondrocyte marker and the average expression level of the fibroblast marker. In some such embodiments, the cell culture is evaluated as containing chondrocytes when the ratio of HAPLN1 expression to that of MFAP5 is greater than 0.25. In particular embodiments, this ratio indicates that the cell culture contains at least 50% chondrocytes.

In some embodiments, the markers' expression levels are compared relative to each other (thus, the thresholds may be defined, e.g., as a given difference between the expression levels of two markers or a ratio thereof). For example, in some embodiments, a ratio of a chondrocyte marker (e.g., HAPLN1) expression level to that of a fibroblast marker (e.g., MFAP5), which is greater than a predetermined threshold, e.g., 0.25, 0.55, 1, 2, 2.2, 5, 10, 25, 50 or more, indicates that the cell culture contains chondrocytes.

In some embodiments of Method 1, the expression levels of chondrocyte and fibroblast markers are determined at the RNA level, e.g., by a standard curve method of quantitative RT-PCR or by a comparative $C_T$ method of quantitative RT-PCR (which measures the difference in the number of threshold cycles required for the fibroblast marker and the chondrocyte markers).

In a related aspect, the invention provides a method of evaluating the phenotype of an individual cell (Method 2), e.g., using flow cytometry. The method is useful for identifying individual cells from a cell culture, including a cell culture derived from cartilage or synovium, a chondrocyte culture, a fibroblast culture, synoviocyte culture, or any other appropriate culture. The method is also useful for identifying individual cells derived from any appropriate biological samples in which it is desirable to identify individual cells, including cartilage samples, synovium samples, fibroblast samples, etc. In some embodiments, Method 2 comprises determining the expression level of a fibroblast marker of the invention in the cell, wherein the expression level below a predetermined threshold indicates that the cell is a chondrocyte. Alternatively, the expression level above a predetermined threshold indicates that the cell is not a chondrocyte (e.g., the cell is a fibroblast or a synoviocyte). In some embodiments, Method 2 comprises:
a) determining the expression level of a chondrocyte marker in the cell;
b) determining the expression level of a fibroblast marker in the cell; and
c) evaluating the phenotype of the cell based on the expression level of the chondrocyte marker and the expression level of the fibroblast marker.

In some embodiments, the cell is identified as a chondrocyte if the expression level of the chondrocyte marker is above a predetermined threshold level, while the expression level of the fibroblast marker is below a predetermined threshold level. The fibroblast and chondrocyte markers in the embodiments of Method 2 may be chosen and evaluated as described for Method 1 above.

Flow cytometry can be performed using commercially available antibodies or such antibodies may be prepared as described in, e.g., Linsenmeyer et al., Biochem. Biophys. Res. Com., 92(2): 440-6 (1980).

Cells and cultures being evaluated by the methods of this invention may be obtained from any biological sample, including any tissue, cell culture, or other material, that may or may not contain chondrocytes. In some embodiments, the cells or cultures being evaluated are of mammalian, particularly human, origin. In some embodiments, the cell culture is grown from cells released from a cartilage biopsy. For example, in autologous chondrocyte implantation, cartilage cells for the procedure are normally cultured from a cartilage biopsy of the patient receiving the implant. Carticel® autologous chondrocyte product (Genzyme Corporation, Cambridge, Mass.) is an example of a cultured chondrocyte product. In some embodiments of the invention, the cell culture comprises a collagen matrix loaded with chondrocytes. Such chondrocytes may be obtained from a cartilage biopsy and cultured prior to being loaded on the matrix, e.g., as used in the MACI® implant product. The method of the invention is useful for identifying, and/or confirming identify of cells loaded onto the collagen support prior to implanting the matrix.

To illustrate an example of the utility of the cell culture determination method, reference is made to FIG. 1. This figure illustrates the steps involved in producing a cultured chondrocyte product for autologous chondrocyte implantation, such as using Carticel® autologous chondrocytes, or for producing a cultured chondrocyte product for the MACI® implantation procedure. In step 1, a cartilage biopsy from a patient undergoing autologous chondrocyte implantation is shipped for processing (step 2). The biopsy material is digested at step 3 to release and harvest chondrocytes from the cartilage. The released cells are plated in tissue culture flasks and expanded in primary culture at step 4, and if necessary, subcultured. Once the cells reach an adequate number, they can be, optionally, cryopreserved at step 5 until the patient is ready to receive the implant. Once the patient is ready to receive the cells, they are thawed and plated into tissue culture flasks and grown to prepare an assembly culture (step 6).

For use in an autologous chondrocyte implant, if a sufficient number of cells are obtained in the assembly culture, the cells are centrifuged to a cell pellet and resuspended in shipping medium, which is the "final product" such as the Carticel® autologous chondrocyte product (step 8). This "final product" is subjected to a number of QC tests, including for example, a sterility test, a cell viability test, an endotoxin test, a mycoplasma test, and a culture composition test (step 9 "QC identity" as described herein) to ensure that the cultured cells contain a sufficient number of chondrocytes. If the cultured cells pass all QC tests, they are shipped (step 10) to the patient for implantation (step 11).

Alternatively, when the assembly culture from step 6 is to be used in a MACI® implant, the cells are resuspended in culture medium, seeded onto a collagen scaffold, and cultured for 4 days (step 7). At the end of the culture period, the cells are rinsed with shipping medium to produce a final product for MACI® implants. This product is also subjected to the QC tests outlined above. Accordingly, whether the final product is a suspension of cultured chondrocytes, such as Carticel® autologous chondrocytes, or the final product is a scaffold-seeded product for MACI® implants, the method of the invention is useful as a lot identification assay or lot release assay, to confirm the composition of a cell culture as containing chondrocytes prior to shipment of the culture. For example, the "QC identity" (step 9) can be performed at any step prior to the final product assembly, e.g., before step 4, 5, 6, 7, or 8.

Many methods of determining gene or protein expression levels are known to persons skilled in the art, e.g., as described in Sambrook et al. (eds.) Cloning: A Laboratory Manual, 2nd ed., Cold Spring Harbor Laboratory Press, 1989; Current Protocols in Molecular Biology (Ausubel et al. (eds.) New York: John Wiley and Sons, 1998). Examples of such methods include polymerase chain reaction (including absolute quantitation by PCR, real time PCR (RT-PCR) and qRT-PCR, multiplex or singleplex PCR), single cell PCR, northern blot assays, nuclease protection assays, in situ hybridization assays, immunohistochemistry assays, immunocytochemistry assays, electrophoresis assays such as gel or capillary, Western blot assays, ELISAs, immunoprecipitation assays, chromatography based assays such as HPLC or gel chromatography, mass spectrometry assays, RNase protection assays, flow cytometry assays, DNA methylation assays, and histone modification analysis assays.

In all methods of the invention, expression levels, at the RNA or at the protein level, can be determined using any suitable method, including any one of conventional methods. RNA levels may be determined by, e.g., quantitative RT-PCR (e.g., TaqMan™ RT-PCR or RT-PCR), Northern blotting, or any other method for determining RNA levels, or as described in the Examples. Protein levels may be determined, e.g., by using Western blotting, ELISA, flow cytometry, enzymatic activity assays, or any other method for determining protein levels. Expression levels may be scaled and/or normalized per total amount of RNA or protein in the sample and/or a control, which may typically be a housekeeping gene such, as beta-actin or glyceraldehyde-3-phosphate dehydrogenase (GAPDH), or 18S ribosomal RNA, etc.). Normalization is typically done to account for variability in the amount of protein, DNA, or RNA input. For example, in the Examples, expression, levels are normalized to 18S ribosomal RNA using a standard curve.

In illustrative embodiments, the expression levels of the fibroblast and chondrocyte markers are determined using RT-PCR, either by a standard curve or by a comparative $C_T$ method for relative quantification. In some embodiments, absolute quantitation of marker copy numbers can be determined by preparing standard curves using known amounts of the markers. The general methods for conducting such assays are described, e.g., in Real-Time PCR Systems: Applied Biosystems 7900HT Fast Real-Time PCR System and 7300/7500 Real-Time PCR Systems, Chemistry Guide, Applied Biosystems, 2005, Part No. 4348358 Rev. E.

In the case of comparing two markers using the comparative $C_T$ method, the amount of the ratio of expression levels of a fibroblast marker to that of a chondrocyte marker can be calculated as $(1+E)^{\wedge}(C_{T,f} - C_{T,c})$, wherein $C_{T,f}$ is the number of the fibroblast marker threshold cycles, $C_{T,c}$ is the number of threshold cycles of the chondrocyte marker, assuming that efficiency of amplification (E) is the same for both markers and the starting amount of both markers is normalized to the same amount of endogenous control (e.g., as in two duplicate samples). In the case of E≈1, as illustrated in the Examples, the ratio can be approximated as $2^{\wedge}(C_{T,f} - C_{T,c})$. Otherwise, the calculations can be performed as described in Appendix A of Real-Time PCR Systems: Applied Biosystems 7900HT Fast Real-Time PCR System and 7300/7500 Real-Time PCR Systems, Chemistry Guide, Applied Biosystems, 2005, Part No. 4348358 Rev. E.

Further embodiments of the invention are illustrated in the following examples, which are intended to be exemplary and not intended to be limiting on the scope of the invention.

EXAMPLES

Example 1

Expression of HAPLN1 and MFAP5 in Chondrocytes, Synoviocytes and Fibroblasts

Cell Isolation and culture—Human chondrocyte cultures were isolated from cartilage using the method for producing Carticel® autologous chondrocytes or the Protease method for producing cultured chondrocytes. Using the method for producing Carticel® autologous chondrocytes, cartilage tissue was trimmed of bone and synovium and subjected to a first digestion where tissue was enzymatically treated in collagenase solution for 18 hours at 37° C. Cells released from the first digestion were plated in tissue culture flasks with fetal bovine serum (FBS) and gentamicin containing medium (EGHXX). The cells were then subjected to a second digestion where remaining tissue from the first digestion was treated with a collagenase/trypsin solution for 2.5 hours at 37° C. Cells released from the second digestion were plated in tissue culture flasks with EGHXX. Tissue pieces remaining after the second digestion were plated in tissue culture flasks with EGHXX. Using the Protease isolation method, cartilage tissue was trimmed of bone and synovium and subjected to a first digestion in Pronase E (Sigma-Aldrich Inc., St. Louis, Mo.) solution for 1.5 hours at 37° C. The Pronase solution was then removed and a second digestion of the cartilage was performed in collagenase solution for 18 hours at 37° C. The released cells were then plated in tissue culture flasks with EGHXX. After isolation, the cell culture methods were the same for cells obtained from either isolation method. Primary cell cultures were re-fed fresh EGHXX every 2 to 4 days. When the primary culture flasks reached 50% to 80% confluence, they were trypsinized to a single cell suspension, neutralized with EGHXX to inactivate trypsin, and a cell count was performed. The resulting cell suspension was then either sampled, further expanded by subculturing, or cryopreserved for long term storage. The subculture of the primary culture is referred to as the secondary culture, or first passage. Subsequent subcultures are referred to as the second passage, third passage, fourth passage, etc. Subculturing was performed by plating cells in tissue culture flasks with EGHXX and re-feeding with fresh EGHXX every 2 to 4 days. When the subcultures reached 80% to 100% confluence, they were trypsinized to a single cell suspension, neutralized with EGHXX to inactivate trypsin, and a cell count was performed. The resulting cell suspension was then either sampled, further expanded, or cryopreserved for long term storage.

Human synoviocyte cultures (synovium derived cell cultures, also known as synovial fibroblasts) S1 and S2 were obtained from Cell Applications Inc. (San Diego, Calif.) as cryopreserved primary cultured cells. The synoviocytes were plated in tissue culture flasks with EGHXX medium and cultured using the method for producing Carticel® autologous chondrocytes as described above. Human dermal fibroblast cultures were purchased from Cell Applications Inc. as cryopreserved-primary cultured cells. The dermal fibroblasts were cultured using the method for producing Carticel® autologous chondrocytes as described above.

The cell cultures used in this Example are listed in Table 2.

TABLE 2

Cell cultures used in RT-PCR Analysis (Example 1)

| Cell Culture | Cell Type | Type of Cell Culture |
|---|---|---|
| PC | Chondrocyte | Primary culture |
| C1 | Chondrocyte | Second Passage |
| C2 | Chondrocyte | Second Passage |
| S1 | Synoviocyte | Second Passage |
| S2 | Synoviocyte | Second Passage |
| F1 | Dermal Fibroblast | Second Passage |
| F2 | Dermal Fibroblast | Second Passage |

RNA and cDNA preparation—RNA was isolated from cell cultures using the TRI-spin procedure (Reno et al., Biotechniques 22: 1082-6 (1997)). Isolated RNA concentrations were determined spectrophotometrically. For the preparation of cDNA from samples PC, C1, C2, S1, S2, F1, and F2, the First Strand Synthesis Kit (Roche, Indianapolis, Ind.), using random hexamer primers was run according to the manufacturer's instructions. The resulting cDNA was stored at −20° C. or −80° C. until analysis.

Gene expression analysis—Gene expression analysis was performed using quantitative real time RT-PCR, using either a standard curve method or a comparative $C_T$ method. The real time PCR method was based on the 5' nuclease cleavage of a dual labeled oligo probe to report sequence specific primer amplification of the target sequence ("TaqMan™" assay). Expression of genes encoding cartilage link protein (HAPLN1) and microfibrillar associated protein 5 (MFAP5) were assayed using TaqMan™ Gene Expression Assays Hs00157103_ml and Hs00185803_ml (Applied Biosystems Inc.), respectively. The real time PCR was prepared with TaqMan™ Universal PCR Master Mix, no UNG (catalog number 432-4018, Applied Biosystems Inc.), appropriate TaqMan™ Gene Expression Assay (Applied Biosystems) and sample cDNA were used according to the Universal PCR Mix protocol. The amplifications were run on an ABI 7500 Real-Time PCR system (Applied Biosystems Inc.) using the standard TaqMan™ cycling and data collection program for this configuration. Duplicate 25 μL reactions were run with up to 5 ng of input cDNA per well. A threshold of 0.1 units was used for all assays.

Standard Curve Method—The standard curve method was performed using the Eukaryotic 18S rRNA Endogenous Control assay (catalog number 4319413E, Applied Biosystems Inc.), in which 18S rRNA is used as an internal control to normalize RT-PCR results to account for input variation. For quantitation of the relative levels of expression of each gene, dilutions of the primary chondrocyte (PC) cDNA were run to generate a standard curve with the 7500 system software. The level of each test sample's expression was determined from the standard curve, and the resulting mRNA ratios to the primary chondrocyte control (PC) were divided by the sample's 18S rRNA ratio to PC to normalize for cDNA loading.

Comparative $C_T$ Method—Comparative $C_T$ analysis was performed to determine the relative gene expression ratios of HAPLN1 to MFAP5 in the various samples from the real time quantitative RT-PCR gene expression analysis raw data generated as described above. The comparative Ct method provides a relative measure of the ratio of HAPLN1 to MFAP5 which allows for direct comparison between test samples without the need for standards, standard curve analysis, or actual calibrators. This method can be employed in the case of the HAPLN1 and MFAP5 assays used in this example because the following four conditions were met: 1) the assay performance was consistent from run to run; 2) equivalent amounts of RNA were run in HAPLN1, MFAP5, and endogenous control assays; 3) the $C_T$ value for the endogenous control gene, 18S rRNA, was always lower than either the HAPLN1 $C_T$ or MFAP5 $C_T$ when equivalent amounts of RNA were run in each assay, and thus 18S $C_T$ was always quantifiable when either HAPLN1 or MFAP5 were quantifiable; and 4) the method used an arbitrarily selected theoretical calibrator defined as a theoretical sample containing the ratio of HAPLN1/MFAP5 which yielded a HAPLN1 $C_T$ value equal to the MFAP5 $C_T$ value when the other three conditions listed above were met. The derivation of the equation used for this comparative $C_T$ method is as follows. Where the amount of target gene in a sample, normalized to an endogenous control gene and relative to a calibrator is given by:

$$(1+E)^{\wedge}(-\Delta\Delta C_{T, target\ gene})$$

wherein $E$=amplification efficiency wherein $$\Delta\Delta C_{T, target\ gene} = \text{sample } \Delta C_{T, target\ gene} - \text{calibrator } \Delta C_{T, target\ gene}$$

and wherein $$\Delta C_{T, target\ gene} = C_{T, target\ gene} - C_{T, endogenous\ control\ gene}$$

(See Liu, W. and Saint, D. A., Analytical Biochemistry, 302: 52-59 (2002); Livak, K. J, ABI Prism 7700 Sequence Detection System, User Bulletin 2, ABI publication 4303859, 1997). Then the ratio of HAPLN1 to MFAP5 can be described as:

$$(1+E)^{\wedge}(-\Delta\Delta C_{T, HAPLN1})/(1+E)^{\wedge}(-\Delta\Delta C_{T, MFAP5})$$

which equals:

$$(1+E)^{\wedge}(-\{[\text{sample } C_{T, HAPLN1} - \text{sample } C_{T, endogenous\ control\ gene}] - [\text{calibrator } C_{T, HAPLN1} - \text{calibrator } C_{T, endogenous\ control\ gene}]\})/(1+E)^{\wedge}(-\{[\text{sample } C_{T, MFAP5} - \text{sample } C_{T, endogenous\ control\ gene}] - [\text{calibrator } C_{T, MFAP5} - \text{calibrator } C_{T, endogenous\ control\ gene}]\})$$

If the same amount of sample is run in each assay, then the $C_T$ of the sample endogenous control gene can be represented by the term x. If the same amount of calibrator is run in each assay, then the $C_T$ of the calibrator endogenous control gene can be represented by the term y. Substituting these terms, the equation derives to:

$$(1+E)^{\wedge}(-\{[\text{sample } C_{T,HAPLN1}-x]-[\text{calibrator } C_{T,HAPLN1}-y]\})/(1+E)^{\wedge}(-\{[\text{sample } C_{T,MFAP5}-x]-[\text{calibrator } C_{T,MFAP5}-y]\})$$

which equals:

$$(1+E)^{\wedge}([x-\text{sample } C_{T,HAPLN1}]-[y-\text{calibrator } C_{T,HAPLN1}])/(1+E)^{\wedge}([x-\text{sample } C_{T,MFAP5}]-[y-\text{calibrator } C_{T,MFAP5}])$$

If the calibrator is defined as a theoretical sample containing the ratio of HAPLN1/MFAP5 which yields a $C_{T,HAPLN1}$ value equal to the $C_{T,MFAP5}$ value when equivalent amounts of calibrator are run in each assay, then the term z can be substituted for the calibrator $C_{T,HAPLN1}$ and the calibrator $C_{T,MFAP5}$. The equation then derives to:

$$(1+E)^{\wedge}([x-\text{sample } C_{T,HAPLN1}]-[y-z])/(1+E)^{\wedge}([x-\text{sample } C_{T,MFAP5}]-[y-z])$$

which equals:

$$(1+E)^{\wedge}([x-\text{sample } C_{T,HAPLN1}]-[y-z]-[x-\text{sample } C_{T,MFAP5}]+[y-z])$$

which equals:

$$(1+E)^{\wedge}([x-\text{sample } C_{T,HAPLN1}]-[x-\text{sample } C_{T,MFAP5}])$$

which equals:

$$(1+E)^{\wedge}(\text{sample } C_{T,MFAP5}-\text{sample } C_{T,HAPLN1})$$

And if E=1 (100% efficiency), then the relative ratio of HAPLN1 to MFAP5 equals:

$$2^{\wedge}(\text{sample } C_{T,MFAP5}-\text{sample } C_{T,HAPLN1})$$

The above equations derive to a final formula leaving only two variables, the sample HAPLN1 $C_T$ and sample MFAP5 $C_T$, as unknowns. This formula applies when samples are assayed under the conditions described above, and the theoretical calibrator employed is set as described above.

Figure 2:
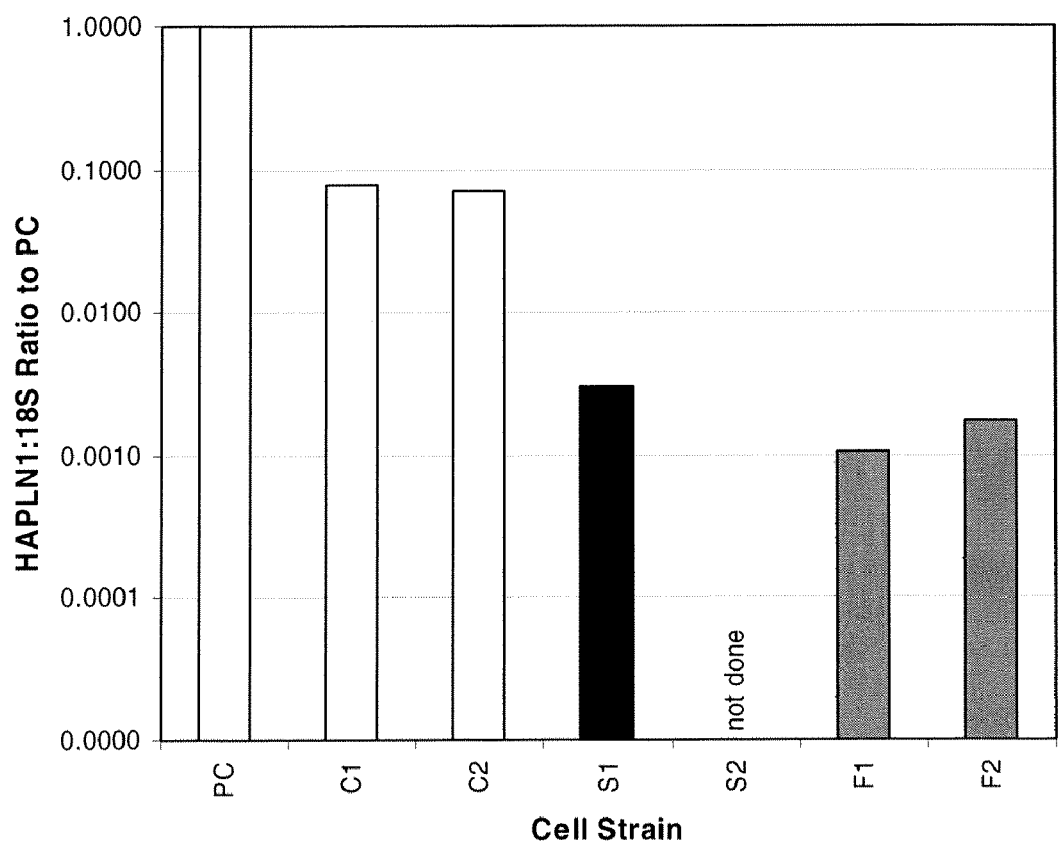
FIG. 2 depicts HAPLN1 expression levels in several cell strains as determined by a standard curve method of RT-PCR. Expression levels were normalized to 18S ribosomal RNA. The expression level in primary chondrocytes (PC) was scaled to 1; other ratios were scaled accordingly. Cell strains used are listed in Table 2.
Figure 3:
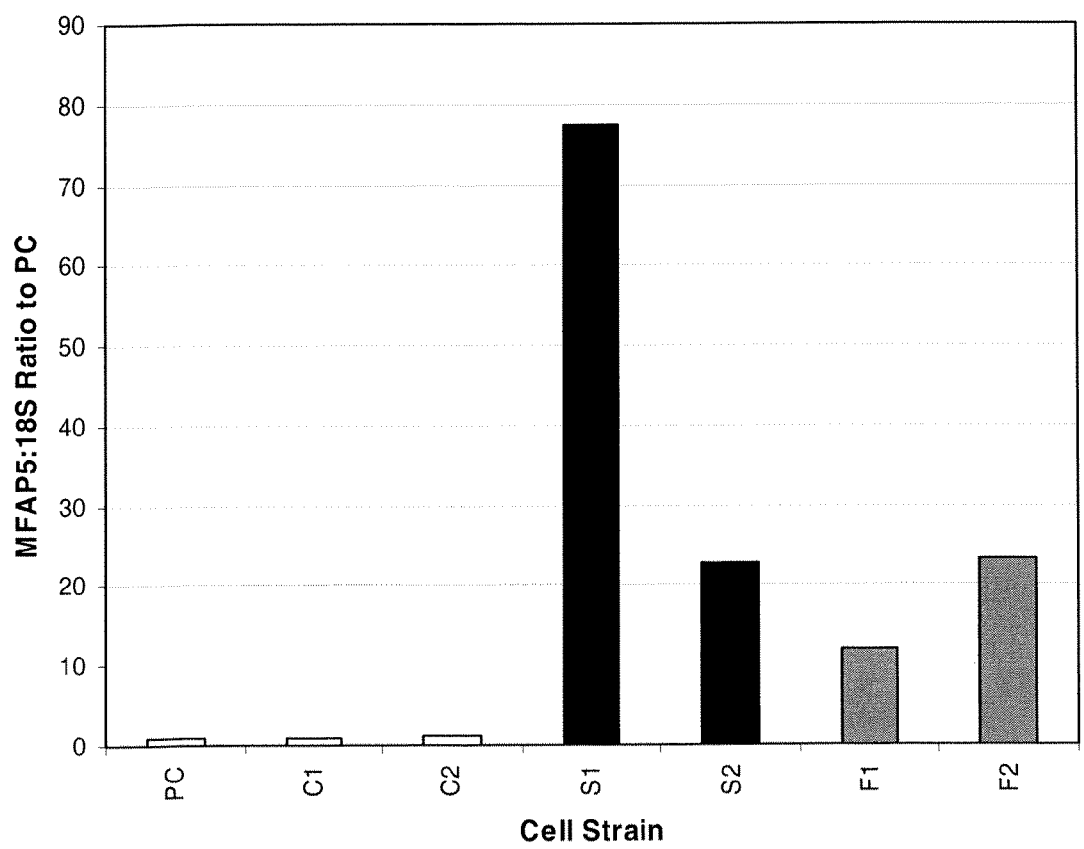
FIG. 3 depicts expression levels of MFAP5 in the same cell strains as shown in FIG. 2, as determined by a standard curve method of RT-PCR. Expression levels were normalized to 18S ribosomal RNA. The expression level in primary chondrocytes (PC) was scaled to 1; other ratios were scaled accordingly.

FIG. 2 depicts HAPLN1 expression levels in several cell strains as determined by a standard curve method of RT-PCR. FIG. 3 depicts expression levels of MFAP5 in the same cell samples as shown in FIG. 2, as determined by a standard curve method of RT-PCR. HAPLN1 was expressed at higher levels in the chondrocyte cell cultures than in the synoviocyte and fibroblast cell cultures. MFAP5 was expressed at higher levels in synoviocyte and fibroblast cell cultures than in the chondrocyte cell cultures.

Figure 4:
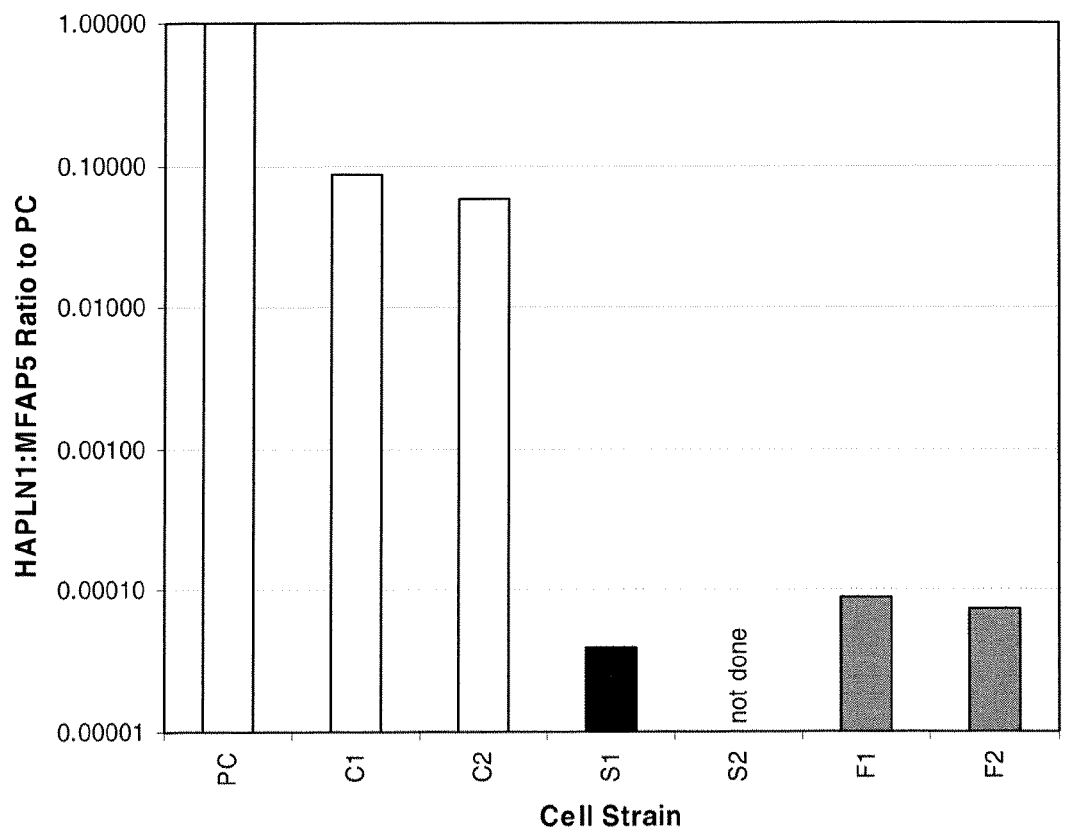
FIG. 4 depicts the ratios of HAPLN1 and MFAP5 expression levels from FIGS. 2 and 3. The ratio in primary chondrocytes (PC) was scaled to 1; other ratios were scaled accordingly.

FIG. 4 depicts the ratios of HAPLN1 and MFAP5 expression levels from FIGS. 2 and 3. The ratio in primary chondrocytes (PC) was scaled to 1; other ratios were scaled accordingly.

Figure 5:
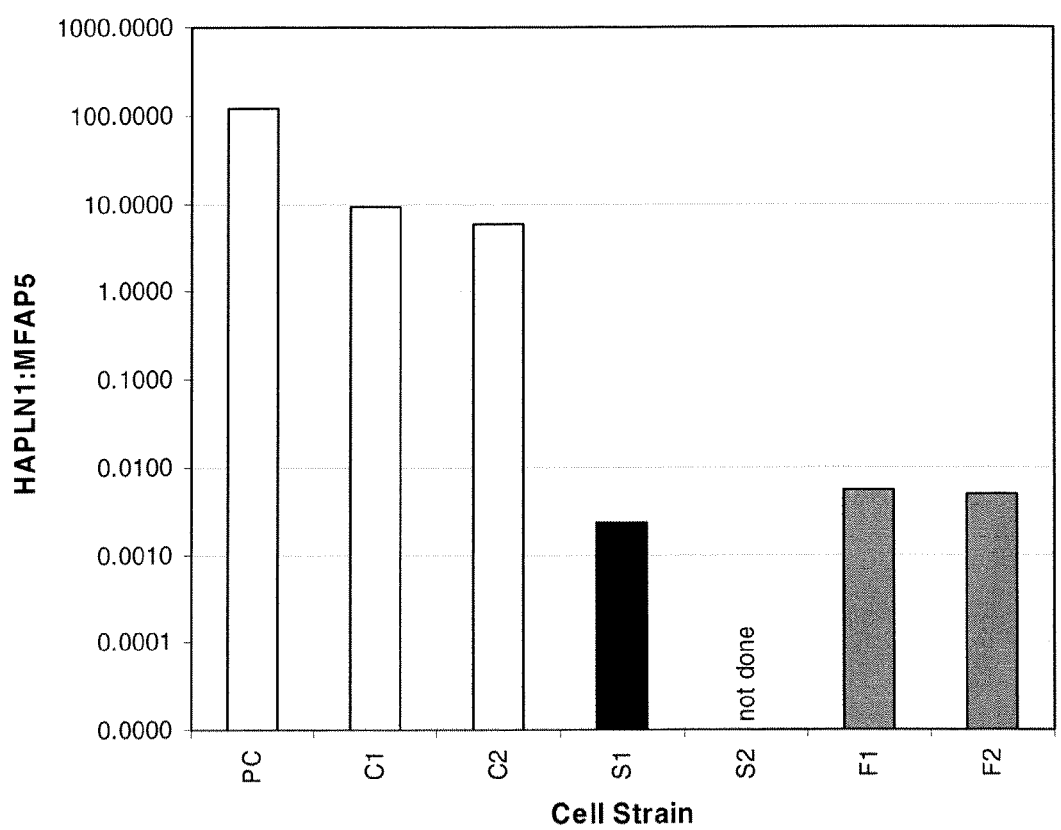
FIG. 5 depicts the ratios of HAPLN1 and MFAP5 expression levels in the same strains as shown in FIG. 2. The expression levels were determined by a comparative $C_T$ method of RT-PCR, and the ratios were calculated as $2^{\wedge}(C_{T,MFAP5}-C_{T,HAPLN1})$.

FIG. 5 depicts the ratios of HAPLN1 and MFAP5 expression levels in the same strains as shown in FIG. 2, however, the expression levels were determined by a comparative $C_T$ method of RT-PCR. The results of the $C_T$ method were similar to the results obtained by the standard curve method.

Example 2

Expression of HAPLN1 and MFAP5 in Additional Strains of Chondrocytes, Synoviocytes and Fibroblasts Expression levels of HAPLN1 and MFAP5 were determined in additional cell cultures to confirm fidelity of the method for differentiating between chondrocyte and synoviocyte cultures. The cultures used in this Example are listed in Table 3.

TABLE 3

Cell cultures used in RT-PCR Analysis (Example 2)

| Cell Culture | Cell Type | Type of Cell Culture |
| --- | --- | --- |
| PC | Chondrocyte | Primary culture |
| C3 | Chondrocyte | Second passage |
| C4 | Chondrocyte | Second passage |
| C5 | Chondrocyte | Second passage |
| C6 | Chondrocyte | Second passage |
| C7 | Chondrocyte | Second passage |
| S3 | Synoviocyte | Second passage |
| S4 | Synoviocyte | Second passage |
| S5 | Synoviocyte | Second passage |
| S6 | Synoviocyte | Second passage |
| S7 | Synoviocyte | Second passage |

Cell isolation and culture—Human chondrocyte cell cultures C3, C4, C5, C6, and C7 were isolated and cultured using the method for producing Carticel® autologous chondrocytes as described in Example 1. Human synoviocyte cultures (synovium derived cell cultures, also known as synovial fibroblasts) were either isolated at Genzyme or obtained from Cell Applications Inc. (San Diego, Calif.). Strains S4, S6, and S7 were isolated at Genzyme using various procedures. S4 was isolated by subjecting minced synovium tissue to digestion in collagenase solution for 3.5 hours at 37° C., followed by a second digestion in trypsin solution for 1 hour at 37° C. Strain S6 was isolated by subjecting minced synovium tissue to digestion in a solution containing collagenase and DNase for 2 hours at 37° C. Strain S7 was isolated by subjecting minced synovium to the method for producing Carticel® autologous chondrocytes. After isolation, the synovium derived cells were plated in tissue culture flasks with EGHXX medium and cultured using the method for producing Carticel® autologous chondrocytes as described in Example 1. Strains S3 and S5 were obtained from Cell Applications Inc. as cryopreserved first passage cells. After thawing, the cells from strains S3 and S5 were plated in tissue culture flasks with EGHXX medium and cultured using the method for producing Carticel® autologous chondrocytes as described in Example 1.

RNA isolation and cDNA preparation—RNA preparations for chondrocyte cell cultures C3, C4, C5, C6, C7 and synoviocyte cultures S3, S4, S5, S6, S7 were performed as described in Example 1. The RNA from these samples was reverse transcribed into cDNA using the High Capacity cDNA Reverse Transcription Kit (Applied Biosystems, Inc., Foster City, Calif.) according to the manufacturer's instructions. The PC cDNA from Example 1 was used in this Example. The cDNA was stored at −20° C. or −80° C. until analysis.

Gene expression analysis—Gene expression analysis was performed using RT-PCR as described in Example 1.

Figure 6:
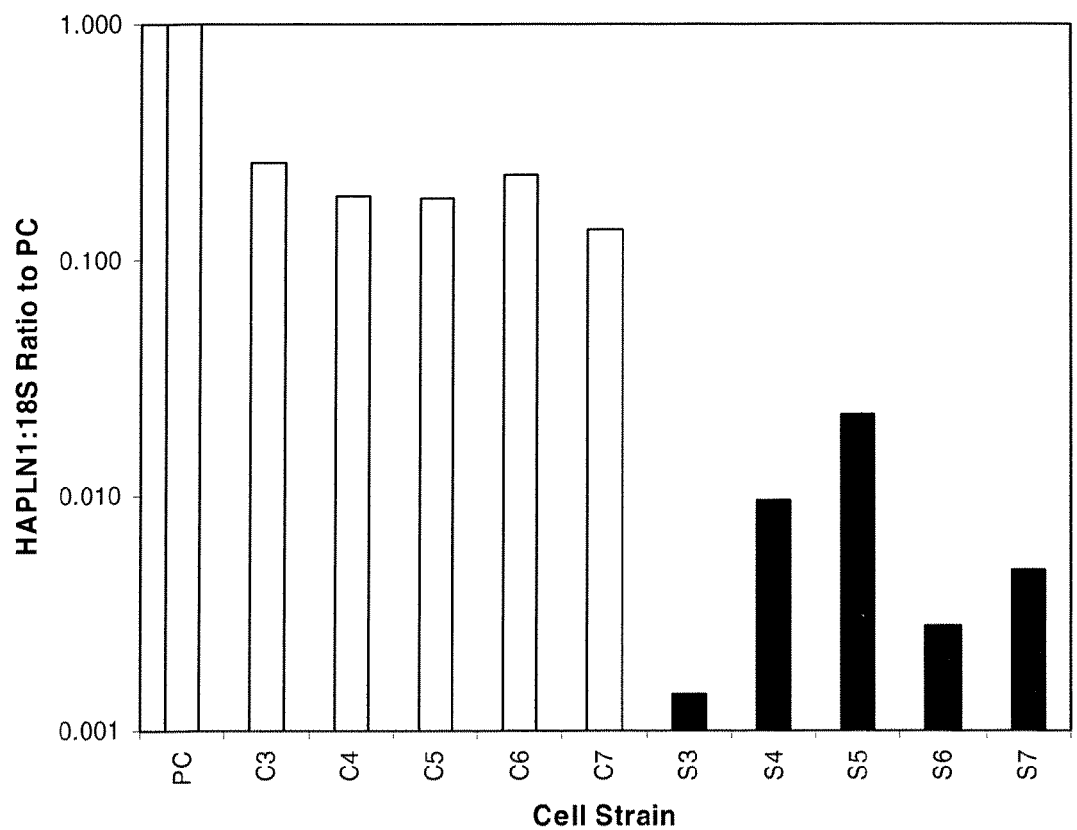
FIG. 6 depicts HAPLN1 expression levels in a number of additional chondrocyte and synoviocyte strains. The expression levels were determined by a standard curve method of RT-PCR and normalized to 18S ribosomal RNA. The expression level in primary chondrocytes (PC) was scaled to 1; other ratios were scaled accordingly. Cell strains used are listed in Table 3.

FIG. 6 depicts HAPLN1 expression levels in a number of additional chondrocyte and synoviocyte strains. The expression levels were determined by a standard curve method of RT-PCR and normalized to 18S ribosomal RNA.

Figure 7:
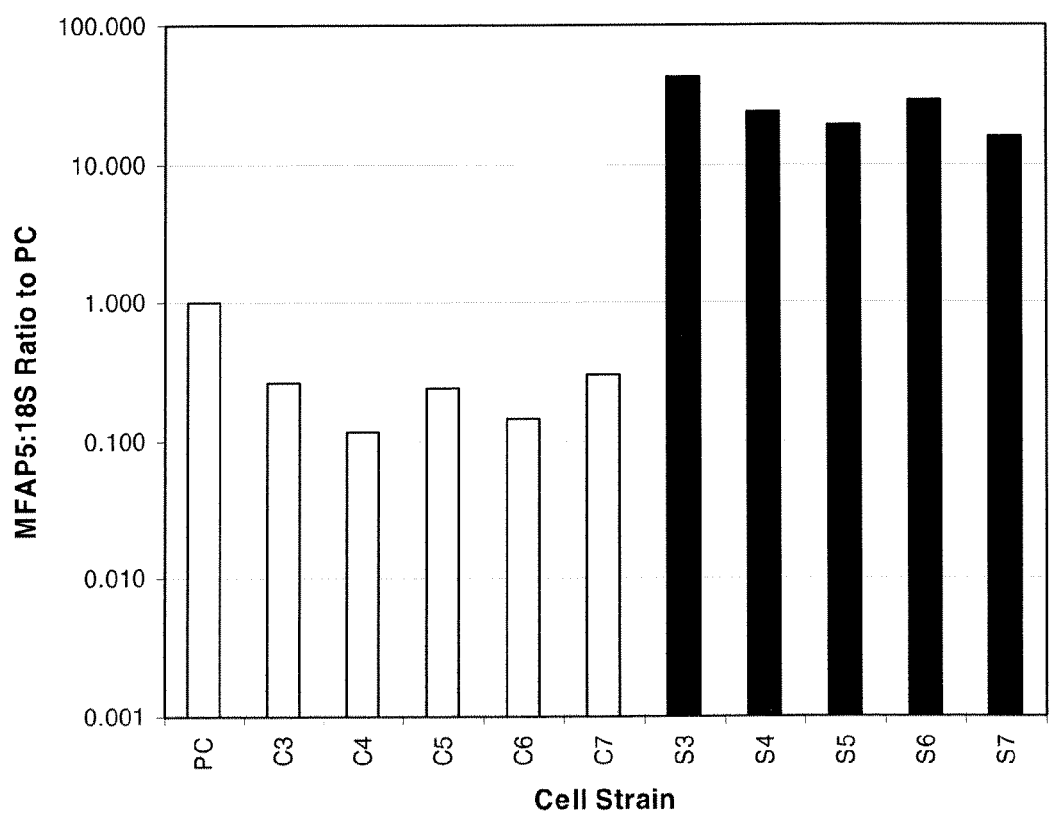
FIG. 7 depicts MFAP5 expression levels in the same strains as shown in FIG. 6. The expression levels were determined by a standard curve method of RT-PCR and normalized to 18S ribosomal RNA. The expression level in primary chondrocytes (PC) was scaled to 1; other ratios were scaled accordingly.

FIG. 7 depicts MFAP5 expression levels in the same strains as shown in FIG. 6. The expression levels were determined by a standard curve method of RT-PCR and normalized to 18S ribosomal RNA.

Figure 8:
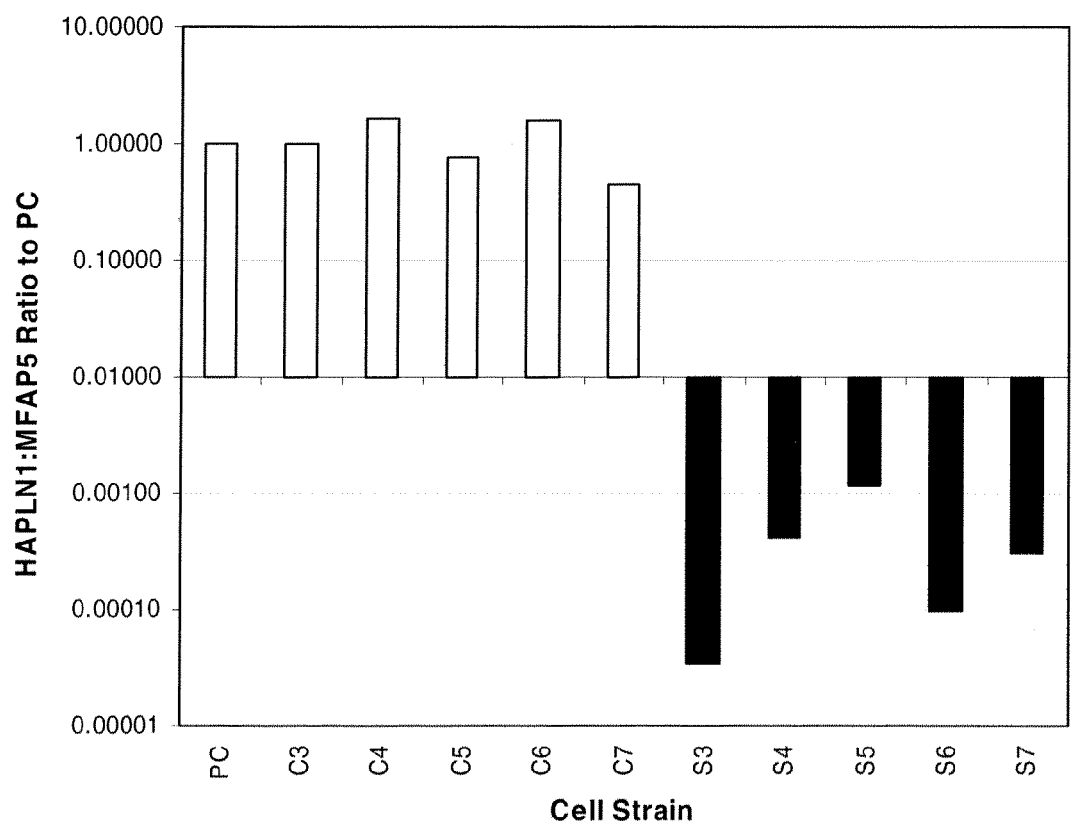
FIG. 8 depicts the ratios of HAPLN1 and MFAP5 expression levels from FIGS. 6 and 7. The ratio in primary chondrocytes (PC) was scaled to 1; other ratios were scaled accordingly.

FIG. 8 depicts the ratios of HAPLN1 and MFAP5 expression levels from FIGS. 6 and 7. The ratio in primary chondrocytes (PC) was scaled to 1; other ratios were scaled accordingly.

Figure 9:
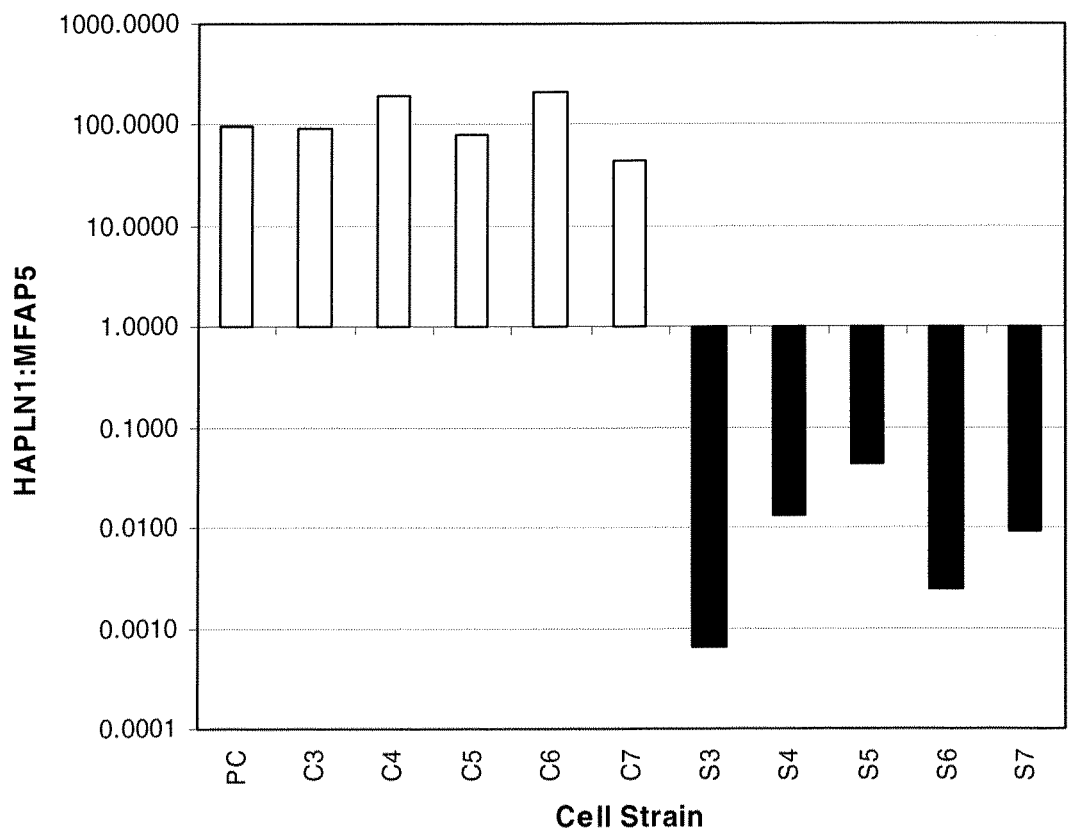
FIG. 9 depicts the ratios of HAPLN1 and MFAP5 expression levels in the same strains as shown in FIG. 6. The expression levels were determined by a comparative $C_T$ method of RT-PCR, and the ratios were calculated as $2^{\wedge}(C_{T,MFAP5}-C_{T,HAPLN1})$.

FIG. 9 depicts the ratios of HAPLN1 and MFAP5 expression levels in the same strains as shown in FIG. 6. The expression levels were determined by a comparative $C_T$ method of RT-PCR, and the ratios were calculated as $2^\wedge(C_{T,MFAP5}-C_{T,HAPLN1})$.

The RT-PCR results in the additional cell strains were consistent with the results obtained in Example 1.

Example 3

Expression of HAPLN1 and MFAP5 in Chondrocytes, Synoviocytes and Fibroblasts Using Custom-Designed Primers and Probes Testing of various chondrocyte, synoviocyte, and dermal fibroblast cultures was performed with primers and probes of known oligonucleotide sequences.

Cell isolation and culture—The cell strains used in this Example are listed in Tables 4 and 5 below. Human chondrocyte cell cultures C1, C2, C3, C4, C5, C6, C7, C8, C26, C28, C30, and C34 were isolated and cultured using the method for producing Carticel® autologous chondrocytes as described in Example 1. Human chondrocyte cell cultures C21, C22, C23, C24, C25, C27, C29, C31, C32, and C33 were isolated (using the Protease method) and cultured as described in Example 1. Cell isolation and culture methods for human synoviocyte cultures S1, S2, S3, S4, S5, S6, and S7 were described in Examples 1 and 2. Synoviocyte culture S9 was isolated by subjecting minced synovium tissue to digestion in a solution containing collagenase and DNase for 2 hours at 37° C. Synoviocyte culture S10 was isolated by subjecting minced synovium tissue to digestion in collagenase solution for 3.5 hours at 37° C., followed by a second digestion in trypsin solution for 1 hour at 37° C. Synoviocyte strains S11, S12, S13, S14, S15, S16, S17, and S18 were obtained from Cell Applications Inc. as cryopreserved first passage cells. Dermal fibroblast strains F1, F2, F3, F4, F5, F6, F8, F9, F10, and F11 were obtained from Cell Applications Inc. as cryopreserved primary cultured cells. All cell cultures were cultured using the method for producing Carticel® autologous chondrocytes as described in Example 1.

TABLE 4

First Set of Cell Cultures used in RT-PCR Analysis (Example 3)

| Cell Culture | Cell Type | Type of Cell Culture |
| --- | --- | --- |
| C1 | Chondrocyte | Second passage |
| C2 | Chondrocyte | Second passage |
| C3 | Chondrocyte | Second passage |
| C4 | Chondrocyte | Second passage |
| C5 | Chondrocyte | Second passage |
| C6 | Chondrocyte | Second passage |
| C7 | Chondrocyte | Second passage |
| C8 | Chondrocyte | Second passage |
| S1 | Synoviocyte | Second passage |
| S2 | Synoviocyte | Second passage |
| S3 | Synoviocyte | Second passage |
| S4 | Synoviocyte | Second passage |
| S5 | Synoviocyte | Second passage |
| S6 | Synoviocyte | Second passage |
| S7 | Synoviocyte | Second passage |
| S9 | Synoviocyte | First passage |
| S10 | Synoviocyte | Third passage |
| S11 | Synoviocyte | Third passage |
| S12 | Synoviocyte | Third passage |
| S13 | Synoviocyte | Third passage |
| F1 | Dermal fibroblast | Second passage |
| F2 | Dermal fibroblast | Second passage |
| F3 | Dermal fibroblast | Second passage |
| F4 | Dermal fibroblast | Second passage |
| F5 | Dermal fibroblast | Second passage |
| F6 | Dermal fibroblast | Second passage |

TABLE 5

Second Set of Cell Cultures used in RT-PCR Analysis (Example 3)

| Cell Culture | Cell Type | Type of Cell Culture |
| --- | --- | --- |
| C21 | Chondrocyte | Second Passage |
| C22 | Chondrocyte | Second Passage |
| C23 | Chondrocyte | Second Passage |
| C24 | Chondrocyte | Second Passage |
| C25 | Chondrocyte | Second Passage |
| C26 | Chondrocyte | Second Passage |
| C27 | Chondrocyte | Second Passage |
| C28 | Chondrocyte | Second Passage |
| C29 | Chondrocyte | Second Passage |
| C30 | Chondrocyte | Second Passage |
| C31 | Chondrocyte | Second Passage |
| C32 | Chondrocyte | Second Passage |
| C33 | Chondrocyte | Second Passage |
| C34 | Chondrocyte | Second Passage |
| S14 | Synoviocyte | Third Passage |
| S15 | Synoviocyte | Third Passage |
| S16 | Synoviocyte | Third Passage |
| S17 | Synoviocyte | Second Passage |
| S18 | Synoviocyte | Second Passage |
| F8 | Dermal fibroblast | Second Passage |
| F9 | Dermal fibroblast | Second Passage |
| F10 | Dermal fibroblast | Second Passage |
| F11 | Dermal fibroblast | Second Passage |

RNA isolation and cDNA preparation—RNA preparations from chondrocyte strains C1, C2, C3, C4, C5, C6, C7, synoviocyte strains S1, S2, S3, S4, S5, S6, S7, and dermal fibroblast strains F1, and F2 were described in Examples 1 and 2. For preparation of RNA from chondrocyte strain C8, synoviocyte strains S9, S10, S11, S12, S13, S14, dermal fibroblast strains F3, F4, F5, and F6, and all strains listed in Table 5, the RNeasy™ Mini Kit (Qiagen, Valencia, Calif.) RNA isolation method was used. For the RNeasy™ isolation, 360 μL of lysis solution was added to cell pellets containing up to one million cells. The samples were immediately vortexed at full speed for 30 seconds, then placed at 37° C. for 5 minutes. After incubation, the samples were shaken by hand for 10 seconds, followed by another 30 second vortex at full speed. The contents of each tube were collected, and the lysate was run through a Qiashredder™ column (Qiagen). Three hundred and fifty μL of the Qiashredded lysate was used in the RNeasy™ procedure following the manufacturer's protocol for the isolation of RNA from animal cells. The columns were eluted with a single elution consisting of 30 μL of water. The RNA was reverse transcribed into cDNA using the High Capacity cDNA Reverse Transcription Kit (Applied Biosystems, Inc., Foster City, Calif.) according to the manufacturer's instructions. The resulting cDNA was stored at −20° C. or −80° C. until analysis.

Gene expression analysis—RT-PCR assays were performed with custom-designed primers and probes specific for regions of HAPLN1 and MFAP5 mRNAs. The sequence information for the custom primers and probes is shown in Table 6. Abbreviations: 6FAM=6-Carboxyfluorescein, VIC™ is a trademark of Applied Biosystems Inc. and is a fluorophore, MGBNFQ=minor groove binder non-fluorescent quencher. Primers were obtained from Invitrogen Corp. (Carlsbad, Calif.). Probes were obtained from Applied Biosystems Inc. For HAPLN1, the target of the forward primer is nucleotides 543 to 570 of the HAPLN1 sequence deposited in a gene sequence database under GENBANK™ Accession No. NM_001884.2 (SEQ ID NO:2), the target of the reverse primer is nucleotides 603 to 622, and the target of the probe is nucleotides 584 through 601 of the same sequence. For MFAP5, the target of the forward primer is nucleotides 301 through 322 of the MFAP5 sequence deposited under GENBANK™ Accession No. NM_003480.2 (SEQ ID NO:1); the target of the reverse primer is nucleotides 353 through 372, and the target of the probe is nucleotides 334 through 350 of the same sequence. Real time PCR was performed with TAQ-MAN™ Fast Universal PCR Master Mix, no UNG (catalog number 4352042, Applied Biosystems Inc.), 900 nM primers, 250 nM probes, and up to 5 ng of sample cDNA, according to the TAQMAN™ Fast Universal PCR Mix protocol. The reaction volume was 13 µL and the amplifications were run on an ABI 7500 Real-Time PCR system (Applied Biosystems Inc.) using the default Fast TAQMAN™ cycling and data collection program for this configuration. A threshold of 0.1 units was used for all assays. The expression levels were determined by a comparative $C_T$ method of RT-PCR described in Example 1.

TABLE 6

Custom Primer and Probe Sequences

| Marker | Forward primer | Reverse Primer | Probe |
|---|---|---|---|
| HAPLN1 | 5' TGAAGGATTAG AAGATGATACTGTT GTG 3' (SEQ ID NO:16) | 5' GCCCCAGTCG TGGAAAGTAA 3' (SEQ ID NO:17) | 5' VIC/ TACAAGGTGTGGTA TTCC/MGBNFQ 3' (SEQ ID NO:18) |
| MFAP5 | 5' CGAGGAGACGA TGTGACTCAAG 3' (SEQ ID NO:19) | 5' AGCGGGATCA TTCACCAGAT 3' (SEQ ID NO:20) | 5' 6FAM/ ACATTCACAGAAGA TCC/MGBNFQ 3' (SEQ ID NO:21) |

Figure 10A:
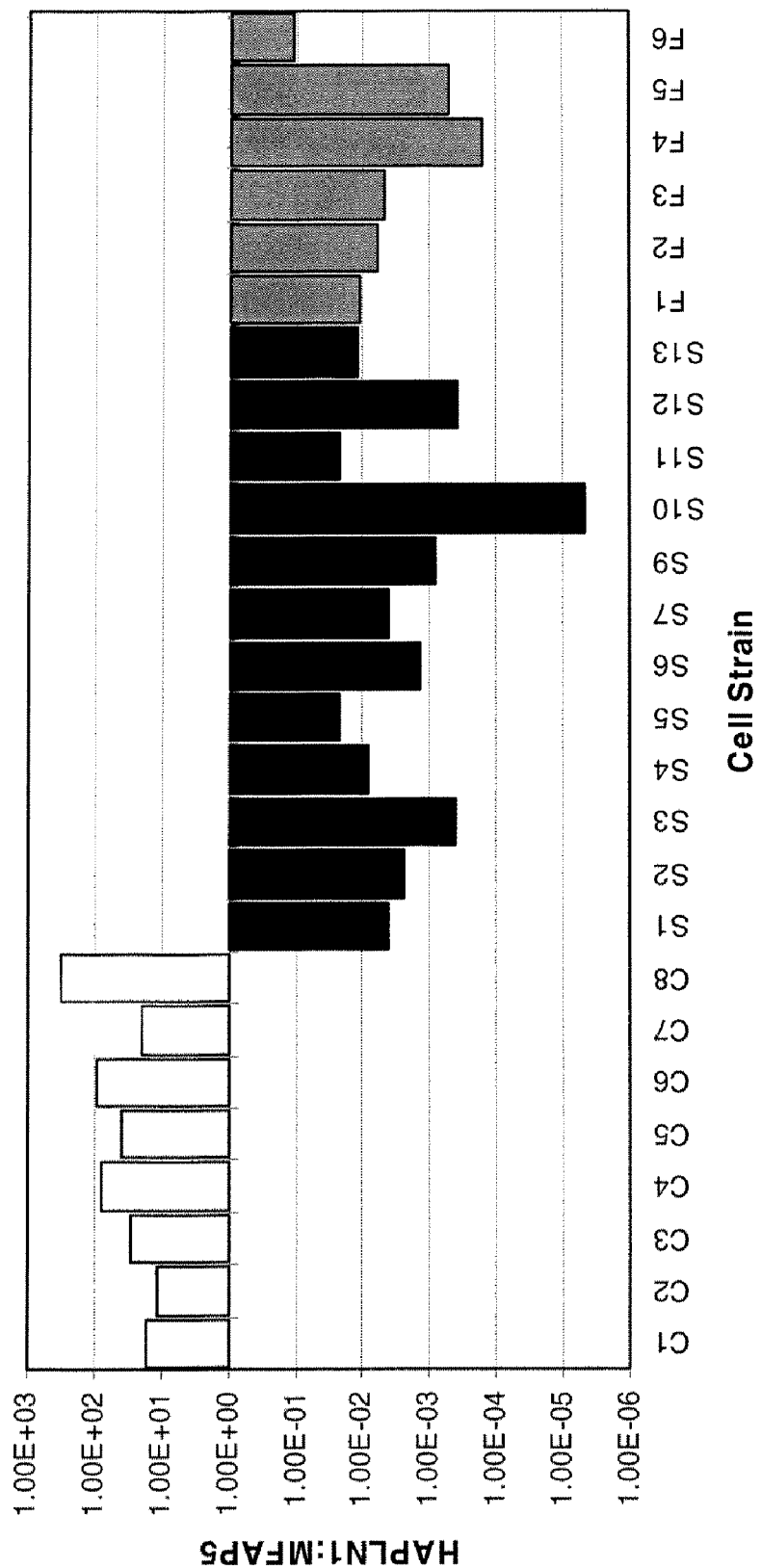
FIG. 10A depicts the ratios of HAPLN1 and MFAP5 expression levels in the same strains as shown in FIGS. 2 and 6, as well as additional chondrocyte, synoviocyte, and dermal fibroblast strains identified in Table 4. The expression levels were determined by a comparative $C_T$ method of RT-PCR using custom-designed primers and probes as described in Example 3. The HAPLN1:MFAP5 ratios were calculated as $2^{\wedge}(C_{T,MFAP5}-C_{T,HAPLN1})$.
Figure 10B:
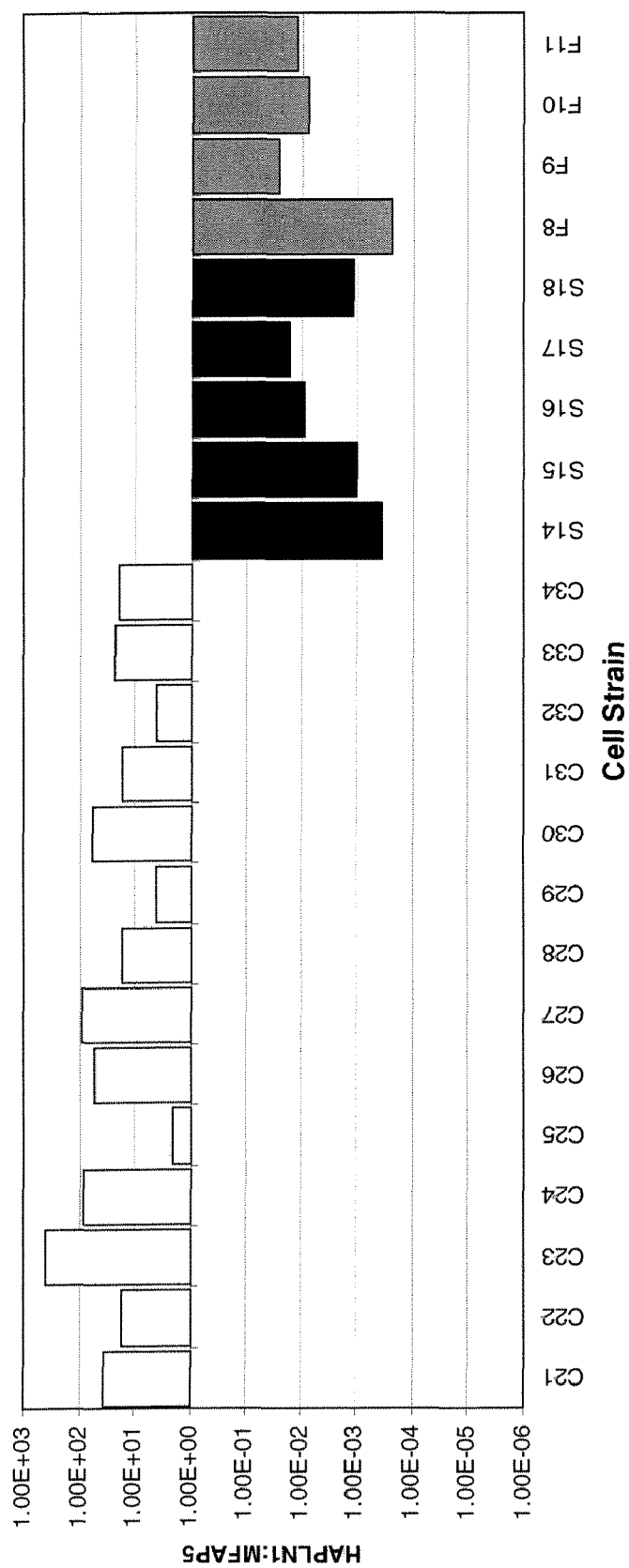
FIG. 10B depicts the ratios of HAPLN1 and MFAP5 expression levels in additional cell strains identified in Table 5. The expression levels were determined using the same methods as described for FIG. 10A.

FIG. 10A depicts the ratios of HAPLN1 and MFAP5 expression levels in the same strains as shown in FIGS. 2 and 6, as well as additional chondrocyte, synoviocyte, and dermal fibroblast strains from Table 4. FIG. 10B depicts the ratios of HAPLN1 and MFAP5 expression levels in strains from Table 5. The results obtained with the custom-designed primers and probes were similar to the results described in Examples 1 and 2.

Example 4

Comparison of HAPLN1 and MFAP5 Expression Levels in Chondrocyte, Synoviocyte and Fibroblast Cultures in Monolayers and Collagen Scaffolds Expression levels of HAPLN1 and MFAP5 were compared in various types of cultures in monolayers and collagen scaffolds.

Cell isolation and culture—Chondrocyte cultures C9, C10, C11, C12, C13, C14, C15, C16, C17, and C18 were isolated using the Protease method as described in Example 1, and cultured as described in Example 1. Synoviocyte culture S7 was isolated and cultured as described in Examples 1 and 2. Dermal fibroblast cultures F2 and F7 were obtained from Cell Applications Inc. as cryopreserved primary cultured cells and cultured as described in Example 1. Upon completion of second passage culture (third passage for culture S7), a sample was taken for RNA isolation (the "Day 0" or monolayer sample), and then the cells were resuspended in EGHXX medium and seeded onto a 20 cm² MAIX™ scaffold (ACI-MAIX™ collagen membrane, CE, Matricel GmbH, D-52134 Herzogenrath, Germany). The cells were allowed to attach for 1 hour at 37° C., then the scaffold was fed additional EGHXX and cultured for 4 days. Scaffold cultures containing synoviocytes and dermal fibroblasts were also prepared in the same manner. After 4 days of scaffold culture, the cultures were sampled using an 8 mm biopsy punch (the "Day 4" or scaffold sample), and RNA isolation was performed.

RNA Isolation and cDNA preparation—RNA was isolated using the RNA isolation kit RNEASY™ Mini Kit (Qiagen, Valencia, Calif.). For the RNEASY™ isolation, 360 µL of lysis solution was added to MACI® implant samples (up to two 8 mm MACI® implant punches per preparation). The samples were immediately vortexed at full speed for 30 seconds, then placed at 37° C. for 5 minutes. After incubation, the samples were shaken by hand for 10 seconds to unfold the membrane followed by another 30 second vortex at full speed. The contents of each tube were collected, and the lysate was run through a biopolymer-shredding system, QIASHREDDER™ column (Qiagen). Three hundred and fifty µL of the Qiashredded lysate was used in the RNEASY™ procedure following the manufacturer's protocol for the isolation of RNA from animal cells. The columns were eluted with a single elution consisting of 30 µL of water. Preparation of cDNA from the sample RNA was performed using the High Capacity cDNA Reverse Transcription Kit (Applied Biosystems, Inc., Foster City, Calif.) according to the manufacturer's instructions. The cDNA was stored at −20° C. or −80° C.

Table 7 lists the cell cultures used and configurations used in this Example.

TABLE 7

Cell cultures used in RT-PCR Analysis (Example 4)

| Culture Code | Cell Type | Culture Type | Configuration |
|---|---|---|---|
| C9 day 0 | Chondrocyte | Second passage | 5 × 10⁵ cell pellet |
| C10 day 0 | Chondrocyte | Second passage | 5 × 10⁵ cell pellet |
| C11 day 0 | Chondrocyte | Second passage | 5 × 10⁵ cell pellet |
| C12 day 0 | Chondrocyte | Second passage | 5 × 10⁵ cell pellet |
| C13 day 0 | Chondrocyte | Second passage | 5 × 10⁵ cell pellet |
| C14 day 0 | Chondrocyte | Second passage | 5 × 10⁵ cell pellet |
| C15 day 0 | Chondrocyte | Second passage | 5 × 10⁵ cell pellet |
| C16 day 0 | Chondrocyte | Second passage | 5 × 10⁵ cell pellet |
| C17 day 0 | Chondrocyte | Second passage | 5 × 10⁵ cell pellet |
| C18 day 0 | Chondrocyte | Second passage | 5 × 10⁵ cell pellet |
| S7 day 0 | Synoviocyte | Third passage | 5 × 10⁵ cell pellet |
| F7 day 0 | Dermal fibroblast | Second passage | 5 × 10⁵ cell pellet |
| F2 day 0 | Dermal fibroblast | Second passage | 5 × 10⁵ cell pellet |
| C9 day 4 | Chondrocyte | MACI ® implant | 8 mm punch |
| C10 day 4 | Chondrocyte | MACI ® implant | 8 mm punch |
| C11 day 4 | Chondrocyte | MACI ® implant | 8 mm punch |
| C12 day 4 | Chondrocyte | MACI ® implant | 8 mm punch |
| C13 day 4 | Chondrocyte | MACI ® implant | 8 mm punch |
| C14 day 4 | Chondrocyte | MACI ® implant | 8 mm punch |
| C15 day 4 | Chondrocyte | MACI ® implant | 8 mm punch |
| C16 day 4 | Chondrocyte | MACI ® implant | 8 mm punch |
| C17 day 4 | Chondrocyte | MACI ® implant | 8 mm punch |
| C18 day 4 | Chondrocyte | MACI ® implant | 8 mm punch |
| S7 day 4 | Synoviocyte | MACI ® implant | 8 mm punch |
| F7 day 4 | Dermal fibroblast | MACI ® implant | 8 mm punch |
| F2 day 4 | Dermal fibroblast | MACI ® implant | 8 mm punch |

Gene expression analysis—Gene expression analysis of the monolayer and MACI® implant cDNA was performed in the manner outlined above in Example 1.

Figure 11:
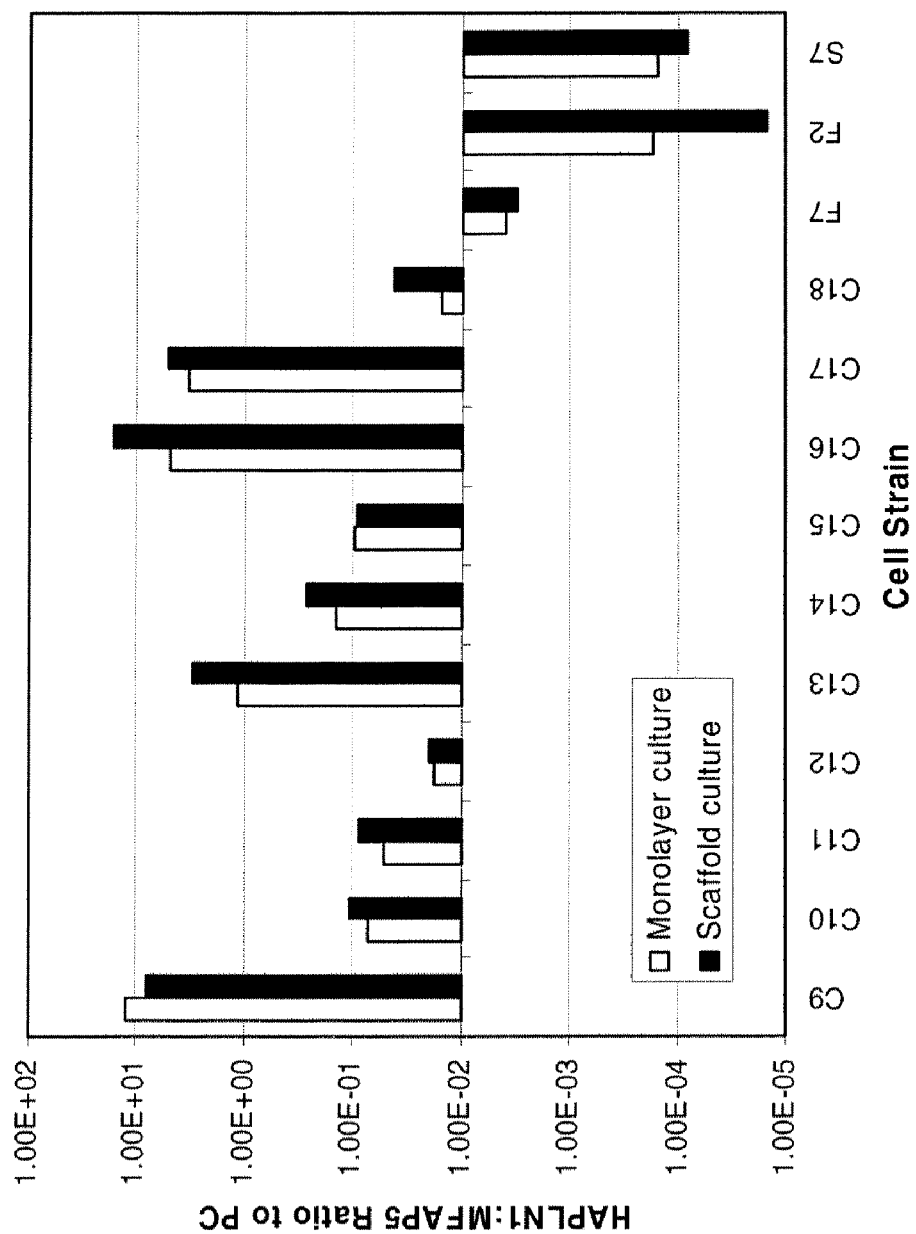
FIG. 11 shows a comparison between expression level ratios for HAPLN1 and MFAP5 in monolayer and collagen-scaffold cultures. Cell strains used are listed in Table 7. HAPLN1 and MFAP5 expression levels were determined by a standard curve method of RT-PCR. Expression levels were normalized to 18S ribosomal RNA. The ratio in monolayer culture of primary chondrocytes (PC) was scaled to 1; other ratios were scaled accordingly.

FIG. 11 shows a comparison between expression level ratios for HAPLN1 and MFAP5 in monolayer and collagen-scaffold cultures. HAPLN1 and MFAP5 expression levels were determined by a standard curve method of RT-PCR. Expression levels were normalized to 18S ribosomal RNA. The ratio in monolayer culture of primary chondrocytes (PC) was scaled to 1; other ratios were scaled accordingly.

Figure 12:
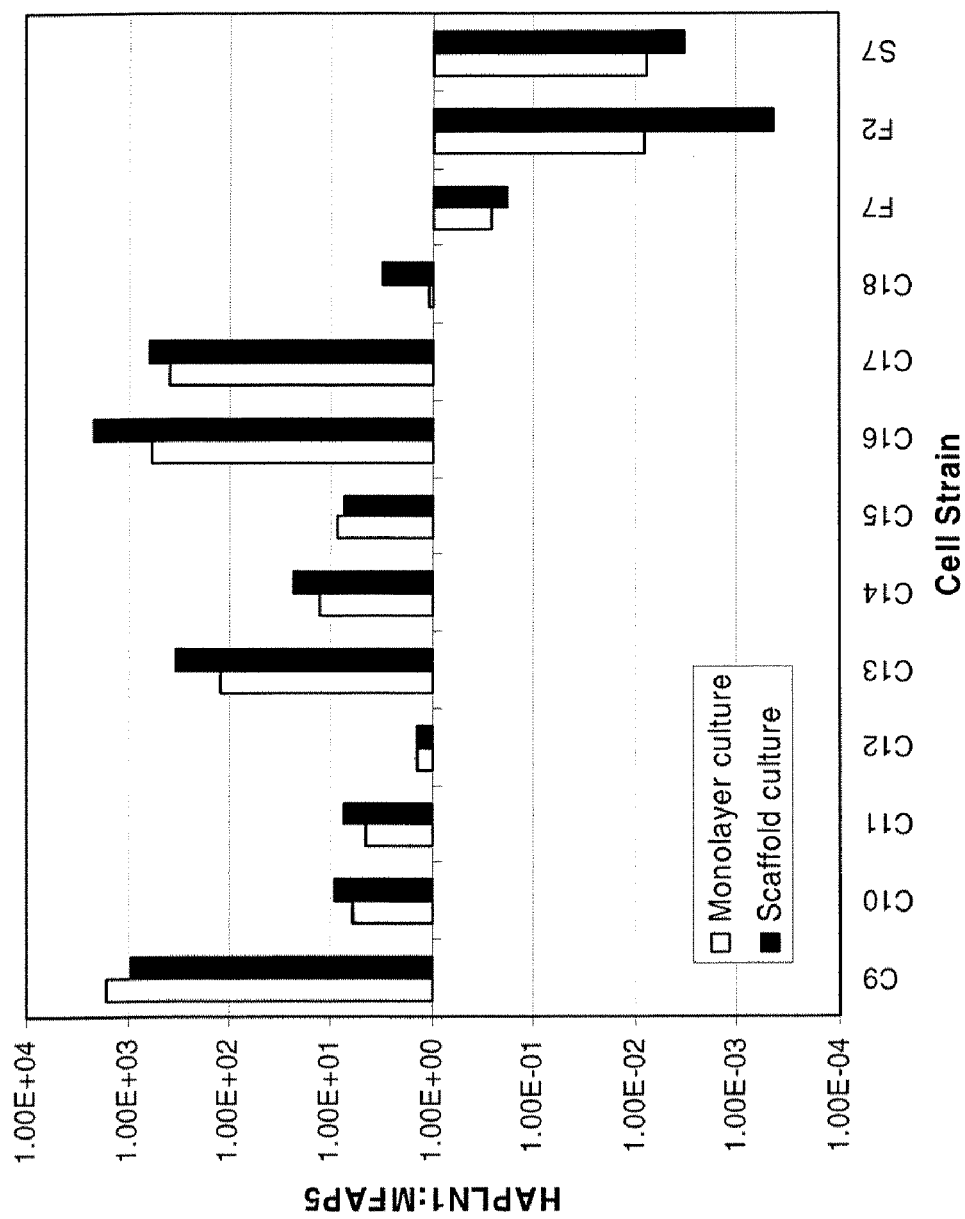
FIG. 12 shows a comparison between expression level ratios for HAPLN1 and MFAP5 in the monolayer and collagen-scaffold cultures using the same strains as shown in FIG. 11. The expression levels of HAPLN1 and MFAP5 were determined by a comparative $C_T$ method of RT-PCR, and the ratios were calculated as $2^{\wedge}(C_{T,MFAP5}-C_{T,HAPLN1})$.

FIG. 12 shows a comparison between expression level ratios for HAPLN1 and MFAP5 in the monolayer and collagen-scaffold cultures using the same strains as shown in FIG. 11. The expression levels of HAPLN1 and MFAP5 were determined by a comparative $C_T$ method of RT-PCR, and the ratios were calculated as $2^{\wedge}(C_{T,MFAP5}-C_{T,HAPLN1})$.

The results obtained in scaffold cultures were similar to those obtained in monolayer cultures.

Example 5

Expression of HAPLN1 and MFAP5 as a Function of the Passage Number

The ratio of HAPLN1 to MFAP5 at various culture levels was investigated.

Cell isolation and culture—Chondrocyte cultures C19, C20, C31, C32, and C33 were isolated using the Protease method as described in Example 1, and cultured as described in Example 1. Synoviocyte cultures S6 and S7 were isolated and cultured as described in Examples 1 and 2. Synoviocyte culture S8 was isolated by subjecting minced synovium tissue to digestion in a solution containing collagenase and DNase for 2 hours at 37° C. Cell culture of S8 was performed as described in Example 1. For chondrocyte cultures C19, C20, C31, C32, and C33, samples of cartilage derived cells (labeled "0" in FIGS. 14A and 14B), primary cultured cells (labeled "1" in FIGS. 14A and 14B), first passage cells (labeled "2" in FIGS. 14A and 14B), and second passage cells (labeled "3" in FIGS. 14A and 14B) were taken. For synoviocyte culture S7, samples of primary cultured (labeled "1" in FIG. 13), first passage (labeled "2" in FIG. 13), second passage (labeled "3" in FIG. 13), third passage (labeled "4" in FIG. 13), and fourth passage (labeled "5" in FIG. 13) cells were taken. For synoviocyte cultures S6 and S8, samples of first passage (labeled "2" on FIG. 13), second passage (labeled "3" on FIG. 13), third passage (labeled "4" on FIG. 13), and fourth passage (labeled "5" on FIG. 13) cells were taken.

RNA isolation and cDNA preparation—RNA and cDNA were prepared using the RNeasy™ Mini Kit (Qiagen) and the High Capacity cDNA Reverse Transcription Kit (Applied Biosystems Inc.) as described in Example 3.

Gene expression analysis—Gene expression analysis of the synoviocyte samples was performed as described in Example 1. Gene expression analysis of the chondrocyte samples was performed as described in Example 3.

Figure 13:
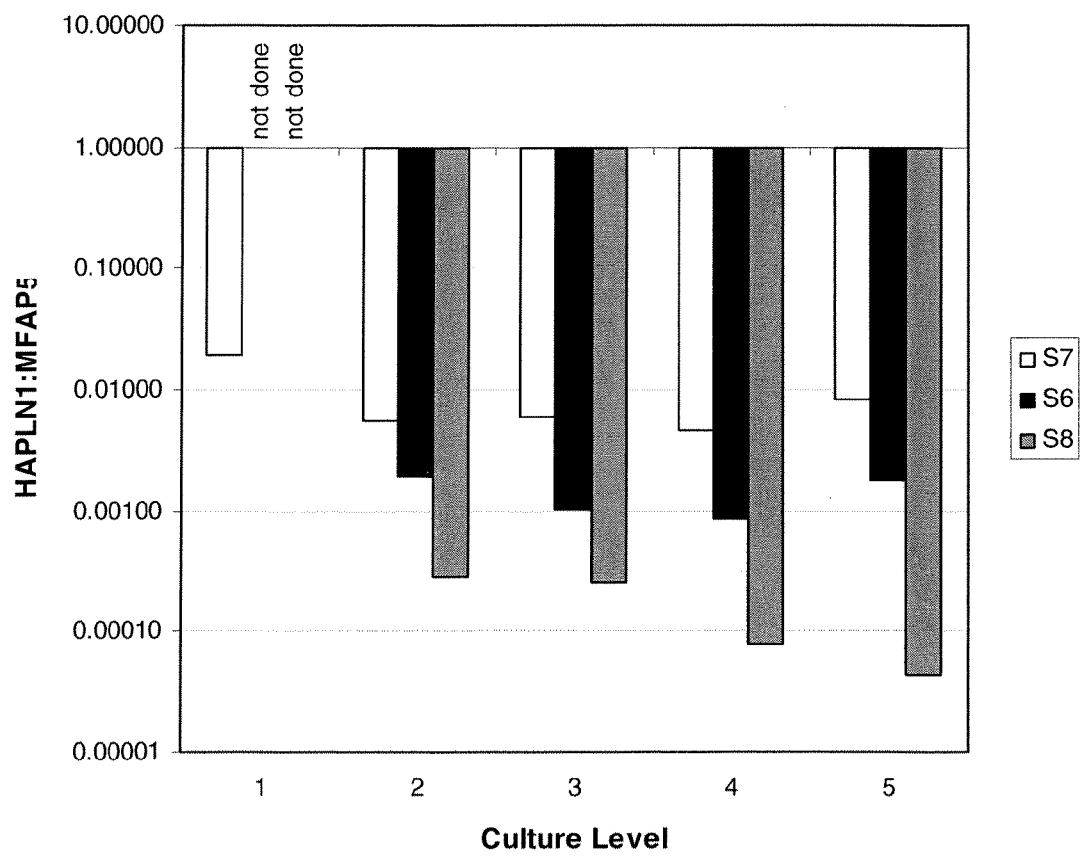
FIG. 13 depicts the change in the expression level ratios for HAPLN1 and MFAP5 as a function of culture level. Three synoviocyte strains were cultured from primary culture (culture level 1) through fourth passage (culture level 5), as shown in the figure. The expression levels of HAPLN1 and MFAP5 were determined by a comparative $C_T$ method of RT-PCR, and the ratios were calculated as $2^{\wedge}(C_{T,MFAP5}-C_{T,HAPLN1})$.
Figure 14A:
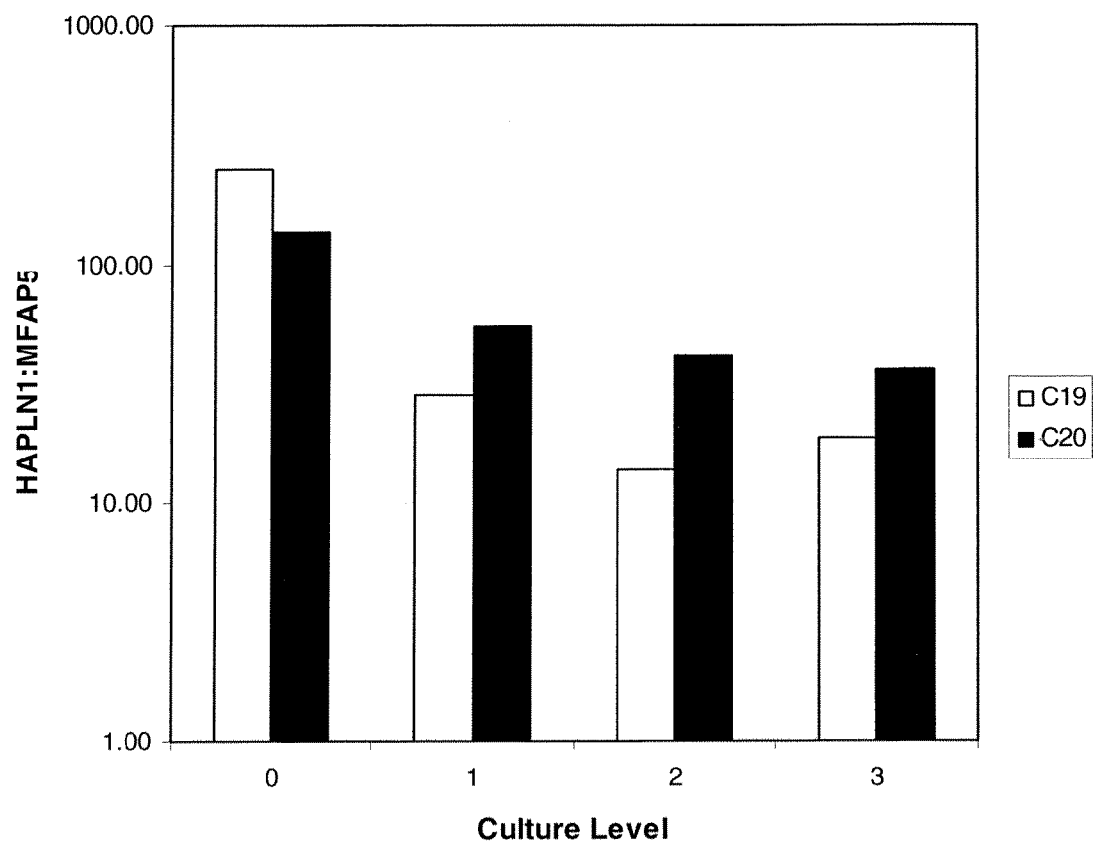
FIGS. 14A and 14B depict the change in the expression level ratios for HAPLN1 and MFAP5 as a function of culture level.
Figure 14B:
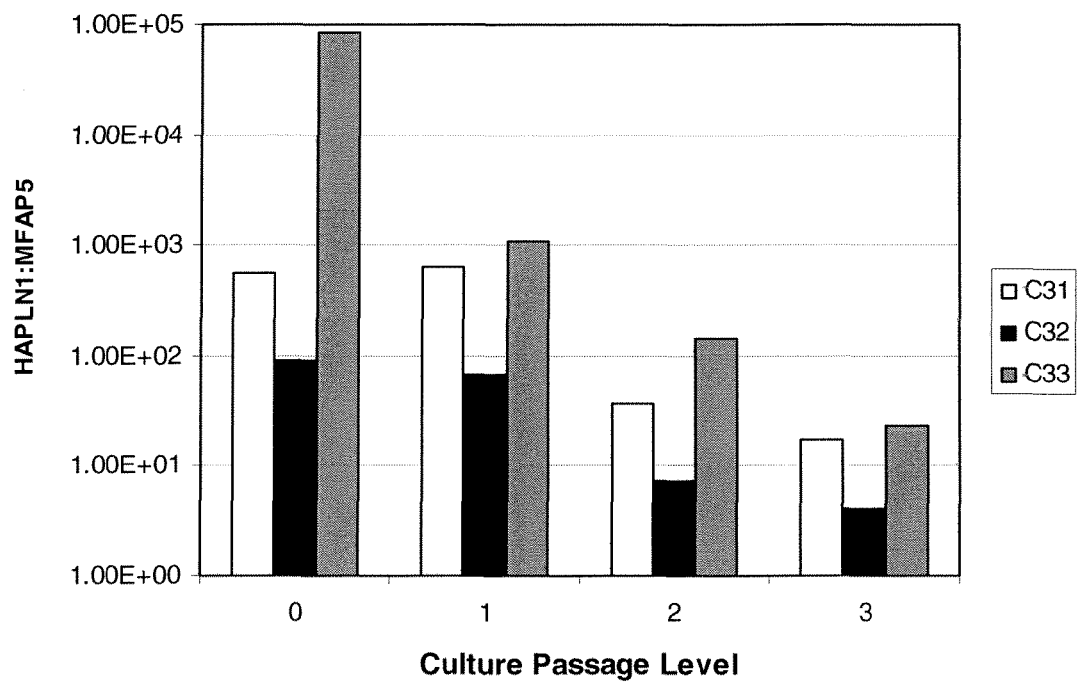

FIGS. 13, 14A, and 14B depict the change in the expression level ratios for HAPLN1 and MFAP5 as a function of the passage number. The expression levels were determined by a comparative $C_T$ method of RT-PCR. The HAPLN1:MFAP5 ratios were calculated as $2^{\wedge}(C_{T,MFAP5}-C_{T,HAPLN1})$.

The ratios of HAPLN1 to MFAP5 were consistently low at all culture levels for the synoviocyte samples relative to the chondrocyte samples. The ratios of HAPLN1 to MFAP5 were consistently high at all culture levels for the chondrocyte samples relative to the synoviocyte samples.

Example 6

Expression of HAPLN1 and MFAP5 in Mixed Cell Cultures

Gene expression analysis was applied to mixed cultures of chondrocyte and synoviocyte cells to evaluate sensitivity level of the method in mixed cultures. Cell cultures of human chondrocytes and human synoviocytes were used to prepare mixtures of the two cell types at the following proportions:
1) 0% chondrocytes/100% synoviocytes;
2) 25% chondrocytes/75% synoviocytes;
3) 50% chondrocytes/50% synoviocytes;
4) 75% chondrocytes/25% synoviocytes; and
5) 100% chondrocytes/0% synoviocytes.

Cell isolation and culture—Chondrocyte strains C5, C6, and C8 were isolated and cultured as described in Examples 1 and 2. Synoviocyte cultures S6, S7, and S9 were isolated and cultured as described in Examples 1, 2, and 3. For Mixing Experiment 1, second passage cultures of chondrocyte strain 6 (C6) and synoviocyte strain 6 (S6) were used. For Mixing Experiment 2, first passage cultures of chondrocyte strain 8 (C8) and synoviocyte strain 7 (S7) were used. For Mixing Experiment 3, first passage cultures of chondrocyte strain 5 (C5) and synoviocyte strain 9 (S9) were used.

RNA isolation and cDNA preparation—RNA and cDNA were prepared using the RNeasy™ Mini Kit (Qiagen) and the High Capacity cDNA Reverse Transcription Kit (Applied Biosystems Inc.) as described in Example 3.

Gene expression analysis—Gene expression analysis was performed as described in Example 3.

Figure 15:
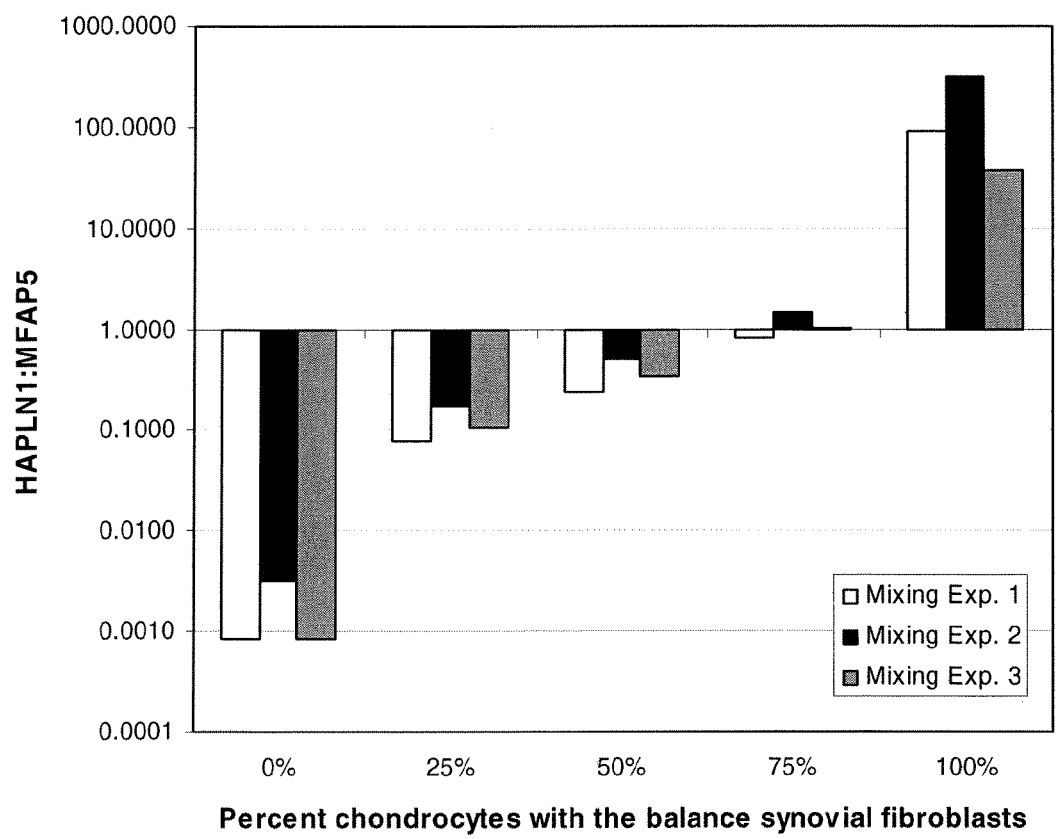
FIG. 15 depicts ratios of expression levels of HAPLN1 and MFAP5 in cultures of mixed populations of chondrocytes and synoviocytes. Three trials were conducted, each with varying proportions of the two cell types. The expression levels were determined by a comparative $C_T$ method of RT-PCR using custom-designed primers and probes as described in Example 6. The HAPLN1:MFAP5 ratios were calculated as $2^{\wedge}(C_{T,MFAP5}-C_{T,HAPLN1})$.

The expression levels were determined by a comparative $C_T$ method of RT-PCR. The HAPLN1:MFAP5 ratios were calculated as $2^{\wedge}(C_{T,MFAP5}-C_{T,HAPLN1})$. The results of the mixing experiments are provided in FIG. 15, which shows the ratios of expression levels of HAPLN1 and MFAP5 in samples consisting of mixed populations of chondrocytes and synoviocytes. In the cultures that contained 75% or less chondrocytes and 25% or more synoviocytes, the HAPLN1: MFAP5 expression level ratios were about 1 or lower. Higher ratios corresponded to higher proportions of chondrocytes in the tested samples. The ability of the assay to discern mixtures of cell cultures showed that, on average, samples composed of at least 67% chondrocytes with the balance consisting of synovial fibroblasts to produce a positive $C_{T,MFAP5}-C_{T,HAPLN1}$. Contamination by other cell types, such as dermal fibroblasts, can also be detected with this assay.

Example 7

Analysis of Relationship Between Assay Response and Molecular Ratio of Markers

Synthetic RNA transcripts of HAPLN1 and MFAP5 were employed to determine the relationship between the assay response and the molecular ratio of the markers in test samples. First, primary PCR (Platinum PCR Supermix, Invitrogen catalog number 11306-016) was performed on human cDNA using the primers listed in Table 8. For HAPLN1, these primers amplified nucleotides from positions 256 to 1171 of the HAPLN1 gene (Accession No. NM_001884.2). For MFAP5, these primers amplified nucleotides from positions 32 to 728 of the MFAP5 gene (Accession No. NM_003480.2). PCR products were analyzed on 1.5% trisacetate EDTA (TAE) agarose gels using a 100 base pair molecular size ladder (100 bp PCR Molecular Ruler, BioRad catalog number 170-8206) for reference and SYBR Green I (Invitrogen catalog number S-7563) gel staining. The resulting primary amplicons were gel purified with 4% native tris-borate EDTA (TBE) polyacrylamide (PAGE) gels and used as a template for secondary PCR with the primers listed in Table 8. Gel-purified primary amplicon template for the secondary MFAP5 amplification was loaded at 0.56 ng per 200 µL of secondary reaction. Gel-purified primary amplicon template for the secondary HAPLN1 amplification was loaded at 2.5 ng per 900 µL of secondary reaction. Secondary amplicons were purified from native TBE PAGE gels as described and used as templates for in vitro transcription with an Ambion Megascript T7 Kit. Up to 1.3 µg of secondary amplicon template was used per 20 µL transcription reaction. The resulting transcripts were gel purified with 6% TBE-Urea (TBU) polyacrylamide gels, resuspended in 0.1 mM EDTA, and quantified spectrophotometrically with readings performed in duplicate using a conversion factor of $1_{A260}$ unit corresponding to a concentration of 40 ng/µL RNA. The gel purified transcripts were analyzed on 6% TBU gels to assess purity. After determination of purity by PAGE analysis and quantitation by spectrophotometry, the number of transcript copies per µL was determined using the conversion factors listed in Table 9. These conversion factors assume an average base molecular weight of 343 Daltons. Avagadro's constant was considered to be $6.02 \times 10^{23}$/mole. It was also assumed that the first base transcribed was the +1 G from the T7 promoter, followed by the target sequence. The transcripts were diluted in yeast RNA carrier buffer (20 ng/µL solution of Yeast RNA (Ambion catalog number AM7120G) in nuclease free water) at concentrations ranging from 103 to 108 copies/µL. The dilutions were then tested using the RT-PCR procedure given in Example 3 of the patent application, except that 2 µL of cDNA was used per 13 µL PCR reaction. The ratio of HAPLN1:MFAP5 was then calculated for each dilution using the comparative Ct method as described in Example 4 of the patent application.

The assay response using the copy number standards was compared to the known molecular ratio. These results are shown in Table 10. With the relationship between the assay response and the molecular ratio determined, the exact molecular ratios at various assay responses were calculated. These results, shown in Table 11, indicate that when the comparative Ct determined acceptance boundary equals 1 (for example, where HAPLN1:MFAP5=1), this corresponds to an exact molecular ratio of HAPLN1:MFAP5 of 2.212.

TABLE 8

Primers Used for Amplification of Copy Number Standards

| Marker | Forward Primer (Primary PCR) | Forward Primer (Secondary PCR) | Reverse Primer (Primary and Secondary PCR) |
|---|---|---|---|
| HAPLN1 | 5' GCCAAGGTGTT TTCACACAG 3' (SEQ ID NO:22) | 5' TAATACGACTC ACTATAGGGCCAA GGTGTTTTCACACA G 3' (SEQ ID NO:23) | 5' CTCTGAAGGAG TAGACACCA 3' (SEQ ID NO:24) |
| MFAP5 | 5' CCTAGCCTGGC TTTCTTGCTC 3' (SEQ ID NO:25) | 5' TAATACGACTC ACTATAGGGCCTAG CCTGGCTTTCTTGC TC 3' (SEQ ID NO:26) | 5' CCATTGGGTCT CTGCAAATCC 3' (SEQ ID NO:27) |

TABLE 9

Expected Transcript Sizes and Conversion Factors

| Transcript | Expected transcript size (bases) | Molecular weight (Daltons) | Copies/ng |
|---|---|---|---|
| HAPLN1 | 917 | $3.145 \times 10^5$ g/mole | $1.914 \times 10^9$/ng |
| MFAP5 | 698 | $2.394 \times 10^5$ g/mole | $2.515 \times 10^9$/ng |

TABLE 10

Assay Response Versus Molecular Ratio of Markers

| Copies of HAPLN1 | Copies of MFAP5 | Exact molecular ratio of HAPLN1:MFAP5 | Assay response, HAPLN1:MFAP5 |
|---|---|---|---|
| $1 \times 10^8$ | $1 \times 10^8$ | 1 | 0.470 |
| $1 \times 10^7$ | $1 \times 10^7$ | 1 | 0.448 |
| $1 \times 10^6$ | $1 \times 10^6$ | 1 | 0.423 |
| $1 \times 10^5$ | $1 \times 10^5$ | 1 | 0.452 |
| $1 \times 10^4$ | $1 \times 10^4$ | 1 | 0.443 |
| $1 \times 10^3$ | $1 \times 10^3$ | 1 | 0.478 |
|  |  |  | Average = 0.452 |

TABLE 11

Exact Molecular Ratio of Markers at Various Assay Responses

| Assay Response, HAPLN1:MFAP5 | Exact molecular ratio of HAPLN1:MFAP5 |
|---|---|
| 500 | 1106 |
| 100 | 221.2 |
| 5 | 11.06 |
| 1 | 2.212 |
| 0.2 | 0.4425 |
| 0.01 | 0.02212 |
| 0.002 | 0.004425 |

Example 8

Absolute Quantitation Analysis of Chondrocyte and Fibroblast Markers

Figure 16:
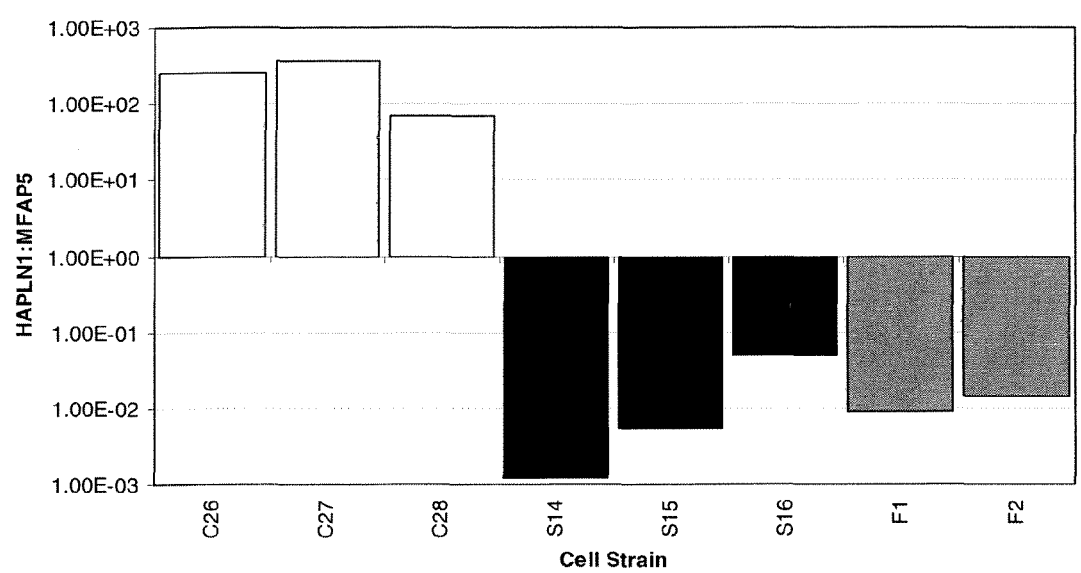
FIG. 16 depicts molar ratios of expression levels of HAPLN1 and MFAP5 in various cell strains, which are listed in Table 12, using absolute copy numbers of the markers as determined by an absolute quantitation method. RT-PCR was performed as described in Example 3, except that 2 μl of cDNA was used per 13 μL PCR reaction. Standard curves were prepared from synthetic HAPLN1 and MFAP5 RNA transcript standards run at $10^3$, $10^4$, and $10^5$ copies/reaction. The quantities of HAPLN1 and MFAP5 mRNA copies present in each test sample were determined from these standard curves.

Gene expression analysis using an absolute quantitation method was performed. Table 12 lists the cell cultures used in this Example. The various cultures were isolated and cultured as discussed in the Examples above. RNA from the cell cultures was isolated using the RNEASY™ Kit as discussed in Example 3. RT-PCR was performed on the cell cultures as described in Example 3, except that 2 µl of cDNA was used per 13 µL PCR reaction. In vitro transcribed RNA standards for HAPLN1 and MFAP5 (prepared as described in Example 7) were diluted to yield cDNA with final concentrations of $5 \times 10^2$, $5 \times 10^3$, and $5 \times 10^4$ copies per uL. Standard curves were generated by graphing the Ct results from the standards on the y-axis, versus the logarithm of the number of copies per reaction ($10^3$, $10^4$, and $10^5$) on the x-axis. A linear trendline was fitted to the data, and the quantities of HAPLN1 and MFAP5 mRNA copies present in each test sample were determined mathematically. This method of quantitation has been previously described, e.g., in Real-Time PCR Systems: Applied Biosystems 7900HT Fast Real-Time PCR System and 7300/7500 Real-Time PCR Systems, Chemistry Guide, Applied Biosystems, 2005, Part No. 4348358 Rev. E. The molar ratio of HAPLN1:MFAP5 was then calculated for each sample. FIG. 16 depicts molar ratios of HAPLN1:MFAP5 in various cell cultures. These results indicate that the molar ratio of HAPLN1:MFAP5 in chondrocytes is high relative to synoviocytes and dermal fibroblasts.

TABLE 12

Cell cultures used in Absolute Quantitation Analysis (Example 8)

| Cell Culture | Cell Type | Type of Cell Culture |
|---|---|---|
| C26 | Chondrocyte | Second Passage |
| C27 | Chondrocyte | Second Passage |
| C28 | Chondrocyte | Second Passage |
| S14 | Synoviocyte | Third Passage |
| S15 | Synoviocyte | Third Passage |

TABLE 12-continued

Cell cultures used in Absolute Quantitation Analysis (Example 8)

| Cell Culture | Cell Type | Type of Cell Culture |
|---|---|---|
| S16 | Synoviocyte | Third Passage |
| F1 | Dermal Fibroblast | Second Passage |
| F2 | Dermal Fibroblast | Second Passage |

All publications and patent documents cited herein are incorporated by reference in their entirety. To the extent the material incorporated by reference contradicts or is inconsistent with the present specification, the present specification will supersede any such material.

The invention claimed is:

1. A method of evaluating the composition of a cell culture, said method comprising:
    a) obtaining a culture of cells for expansion of chondrocytes;
    b) selecting a plurality of cells from the cell culture;
    c) determining the average expression level of microfibrillar associated protein 5 (MFAP5) in the plurality of cells; and
    d) determining the composition of the culture based on the average expression level of MFAP5;
wherein the average expression level of MFAP5 below a predetermined threshold indicates that the cell culture comprises chondrocytes.

2. The method of claim 1, further comprising determining the average expression level of a chondrocyte marker in the plurality of cells; and, in step d), determining the composition of the culture based on the average expression level of the chondrocyte marker and the average expression level of MFAP5.

3. The method of claim 2, wherein MFAP5 and the chondrocyte marker are such that the ratio of their expression levels (chondrocyte marker to MFAP5) in chondrocytes is equal to or greater than 5 times the ratio in dermal fibroblasts or synoviocytes.

4. The method of claim 2, wherein the chondrocyte marker is selected from the group consisting of hyaluronan and proteoglycan link protein 1 (HAPLN1), matrix Gla protein (MGP), GF-like repeats and discoidin I-like domains 3 (EDIL3), WNT1 inducible signaling pathway protein 3 (WISP3), aggrecan 1 (AGC1), cartilage oligomeric matrix protein (COMP), type II collagen, alpha 1 (COL2A1), type IX collagen, alpha 1 (COL9A1), type XI collagen, alpha 1 (COL11A1), leukocyte cell derived chemotaxin 1 protein (LECT1), S100 calcium binding protein beta (S100B), cartilage acidic protein 1 (CRTAC1), SRY-box9 protein (SOX9), and nebulette (NEBL).

5. The method of claim 2, wherein the chondrocyte marker is HAPLN1.

6. The method of claim 2, wherein the expression levels of MFAP5 and the chondrocyte marker are determined at the RNA level.

7. The method of claim 6, wherein the expression levels are determined using PCR.

8. The method of claim 7, wherein the expression levels are determined using comparative $C_T$ PCR method.

9. The method of claim 2, wherein an expression level ratio of the chondrocyte marker to MFAP5 of greater than 0.25, as determined using comparative $C_T$ PCR method, indicates that the cell culture contains chondrocytes.

10. The method of claim 2, wherein a molar ratio of the chondrocyte marker to MFAP5 of greater than 0.55 indicates that the cell culture contains chondrocytes.

11. The method of claim 1, wherein the cell culture comprises cells obtained from a cartilage biopsy.

12. The method of claim 11, wherein the cartilage biopsy is taken from a knee joint.

13. The method of claim 11, wherein, following the evaluation of the cell culture, the cells from the cell culture are administered to a patient in need thereof.

14. The method of claim 13, wherein the cells from the culture are used for autologous chondrocyte implantation.

15. A method of evaluating the composition of a cell culture, the method comprising:
   a) obtaining a culture of cells for expansion of chondrocytes;
   b) determining the expression level of MFAP5 in the cell culture; and
   c) determining the composition of the cell culture based on the expression level of MFAP5.

16. The method of claim 15, further comprising determining the expression level of a chondrocyte marker in the cell culture; and, in step c), determining the composition of the cell culture based on the expression levels of the chondrocyte marker and MFAP5.

17. The method of claim 16, wherein the chondrocyte marker is selected from the group consisting of hyaluronan and proteoglycan link protein 1 (HAPLN1), matrix Gla protein (MGP), GF-like repeats and discoidin I-like domains 3 (EDIL3), WNT1 inducible signaling pathway protein 3 (WISP3), aggrecan 1 (AGC1), cartilage oligomeric matrix protein (COMP), type II collagen, alpha 1 (COL2A1), type IX collagen, alpha 1 (COL9A1), type XI collagen, alpha 1 (COL11A1), leukocyte cell derived chemotaxin 1 protein (LECT1), S100 calcium binding protein beta (S100B), cartilage acidic protein 1 (CRTAC1), SRY-box9 protein (SOX9), and nebulette (NEBL).

18. The method of claim 16, wherein the chondrocyte marker is HAPLN1.

19. The method of claim 16, wherein the expression levels of the chondrocyte marker and MFAP5 are determined at the RNA level.

20. A method of evaluating the composition of a cell culture, said method comprising:
   a) obtaining a cartilage biopsy from a mammal;
   b) isolating cells from the biopsy;
   c) culturing the isolated cells in a cell culture to produce chondrocytes;
   d) determining the expression levels of MFAP5 and HAPLN1 in a plurality of cells obtained from the cell culture; and
   e) determining the composition of the culture based on the expression levels of MFAP5 and HAPLN1.

21. The method of claim 20, wherein the expression levels of MFAP5 and HAPLN1 are determined at the RNA level.

22. The method of claim 21, wherein the expression levels are determined using PCR.

23. The method of claim 22, wherein the expression levels are determined using comparative $C_T$ PCR method.

24. The method of claim 20, wherein an expression level ratio of HAPLN1 to MFAP5 greater than 0.25, as determined using comparative $C_T$ PCR method, indicates that the cell culture contains chondrocytes.

25. The method of claim 20, wherein a molar ratio of HAPLN1 to MFAP5 greater than 0.55 indicates that the cell culture contains chondrocytes.

26. A method of evaluating the composition of a cell culture comprising:
   a) obtaining a cartilage biopsy from a mammal;
   b) isolating cells from the biopsy;
   c) culturing the isolated cells in a cell culture to produce chondrocytes;
   d) determining the expression levels of MFAP5 and a chondrocyte marker in a plurality of cells obtained from the cell culture; and
   e) determining the presence of chondrocytes in the cell culture based on the expression levels of MFAP5 and the chondrocyte marker.

27. The method of claim 26, wherein the chondrocyte marker is selected from the group consisting of hyaluronan and proteoglycan link protein 1 (HAPLN1), matrix Gla protein (MGP), GF-like repeats and discoidin I-like domains 3 (EDIL3), WNT1 inducible signaling pathway protein 3 (WISP3), aggrecan 1 (AGC1), cartilage oligomeric matrix protein (COMP), type II collagen, alpha 1 (COL2A1), type IX collagen, alpha 1 (COL9A1), type XI collagen, alpha 1 (COL11A1), leukocyte cell derived chemotaxin 1 protein (LECT1), S100 calcium binding protein beta (S100B), cartilage acidic protein 1 (CRTAC1), SRY-box9 protein (SOX9), and nebulette (NEBL).

28. The method of claim 26, wherein the chondrocyte marker is HAPLN1.

29. A method of evaluating the composition of a cell culture to confirm the presence of chondrocytes comprising:
   a) obtaining a plurality of cells from a cell culture comprising cells derived from cartilage or synovium; and
   b) determining the average expression level of microfibrillar associated protein 5 (MFAP5) in the plurality of cells; wherein the average expression level of MFAP5 below a predetermined threshold indicates that the cell culture comprises chondrocytes.

30. A method of evaluating the composition of a chondrocyte cell culture to identify the presence of fibroblasts and/or synoviocytes comprising:
   a) obtaining a plurality of cells from a chondrocyte cell culture; and
   b) determining the average expression level of microfibrillar associated protein 5 (MFAP5) in the plurality of cells; wherein an average expression level of MFAP5 above a predetermined threshold indicates that the cell culture comprises fibroblasts and/or synoviocytes.

31. A method of evaluating the composition of a cell culture to determine the ratio of chondrocytes to fibroblasts and/or synoviocytes comprising:

a) performing a cell count of a chondrocyte cell culture
b) obtaining a plurality of cells from the cell culture; and
c) determining the average expression level of microfibrillar associated protein 5 (MFAP5) in the plurality of cells;

wherein an average expression level of MFAP5 above a predetermined threshold indicates that the cell culture comprises more fibroblasts and/or synoviocytes than chondrocytes and an average expression level of MFAP5 below a predetermined threshold indicates that the cell culture comprises more chondrocytes than fibroblasts and/or synoviocytes.

32. The method of claim 31, further comprising determining the expression level of a chondrocyte marker in the plurality of cells; and determining the ratio of chondrocytes to fibroblasts and/or synoviocytes based on the expression levels of the chondrocyte marker and MFAP5.

33. The method of claim 32, wherein the chondrocyte marker is selected from the group consisting of hyaluronan and proteoglycan link protein 1 (HAPLN1), matrix Gla protein (MGP), GF-like repeats and discoidin I-like domains 3 (EDIL3), WNT1 inducible signaling pathway protein 3 (WISP3), aggrecan 1 (AGC1), cartilage oliqomeric matrix protein (COMP), type II collagen, alpha 1 (COL2A1), type IX collagen, alpha 1 (COL9A1), type XI collagen, alpha 1 (COL11A1), leukocyte cell derived chemotaxin 1 protein (LECT1), S100 calcium binding protein beta (S100B), cartilage acidic protein 1 (CRTAC1), SRY-box9 protein (SOX9), and nebulette (NEBL).

34. The method of claim 32, wherein the chondrocyte marker is HAPLN1.

* * * * *

UNITED STATES PATENT AND TRADEMARK OFFICE
CERTIFICATE OF CORRECTION

| | | |
|---|---|---|
| PATENT NO. | : 8,029,992 B2 | Page 1 of 1 |
| APPLICATION NO. | : 12/098033 | |
| DATED | : October 4, 2011 | |
| INVENTOR(S) | : Stephen Rapko et al. | |

It is certified that error appears in the above-identified patent and that said Letters Patent is hereby corrected as shown below:

In claim 31, column 79, line 1, "culture" should read --culture;--.

In claim 33, column 80, line 6, "oliqomeric" should read --oligomeric--.

Signed and Sealed this
Third Day of January, 2012

David J. Kappos
*Director of the United States Patent and Trademark Office*